United States Patent
Song et al.

(10) Patent No.: US 11,685,778 B2
(45) Date of Patent: Jun. 27, 2023

(54) ANTI-HUMAN LAG-3 MONOCLONAL ANTIBODY AND USE THEREOF

(71) Applicant: JIANGSU HUAIYU PHARMACEUTICAL CO., LTD., Nantong (CN)

(72) Inventors: Ningning Song, Shanghai (CN); Qing Duan, Shanghai (CN); Xiaohui Shao, Shanghai (CN); Peng Wang, Shanghai (CN); Xiaojiao Bian, Shanghai (CN); Qian Wang, Shanghai (CN); Peipei Wei, Shanghai (CN); Yajun Huang, Shanghai (CN); Jian Wu, Shanghai (CN); Meiling Wang, Shanghai (CN); Yuandong Wang, Shanghai (CN); Lina Xu, Shanghai (CN); Tatchi Teddy Yang, Shanghai (CN); Lile Liu, Shanghai (CN)

(73) Assignee: JIANGSU HUAIYU PHARMACEUTICAL CO., LTD., Jiangsu (CN)

( * ) Notice: Subject to any disclaimer, the term of this patent is extended or adjusted under 35 U.S.C. 154(b) by 241 days.

(21) Appl. No.: 17/045,166

(22) PCT Filed: Apr. 2, 2019

(86) PCT No.: PCT/CN2019/081063
§ 371 (c)(1),
(2) Date: Oct. 3, 2020

(87) PCT Pub. No.: WO2019/192493
PCT Pub. Date: Oct. 10, 2019

(65) Prior Publication Data
US 2021/0155689 A1    May 27, 2021

(30) Foreign Application Priority Data
Apr. 3, 2018  (CN) .......................... 201810290569.4

(51) Int. Cl.
| C07K 16/00 | (2006.01) |
| C07K 16/46 | (2006.01) |
| C07H 21/04 | (2006.01) |
| C12N 1/20 | (2006.01) |
| C12N 15/00 | (2006.01) |
| C07K 16/28 | (2006.01) |
| G01N 33/68 | (2006.01) |

(52) U.S. Cl.
CPC ..... *C07K 16/2803* (2013.01); *G01N 33/6872* (2013.01); *C07K 2317/24* (2013.01); *C07K 2317/56* (2013.01); *C07K 2317/565* (2013.01); *C07K 2317/76* (2013.01); *C07K 2317/92* (2013.01); *G01N 2333/70503* (2013.01)

(58) Field of Classification Search
None
See application file for complete search history.

(56) References Cited

U.S. PATENT DOCUMENTS

| 4,816,397 A | 3/1989 | Boss et al. |
| 4,816,567 A | 3/1989 | Cabilly et al. |
| 5,585,089 A | 12/1996 | Queen et al. |

FOREIGN PATENT DOCUMENTS

| CN | 107474137 A | 12/2017 |
| WO | WO-2017/037203 A1 | 3/2017 |
| WO | WO-2017/149143 A1 | 9/2017 |

OTHER PUBLICATIONS

Brown et al. Tolerance of single, but not multiple, amino acid replacements in antibody VH CDR 2: a means of minimizing B cell wastage from somatic hypermutation? J. Immuno. May 1996, 3285-91. (Year: 1996).*
Vajdos et al. Comprehensive functional maps of the antigen-binding site of an anti-ErbB2 antibody obtained with shotgun scanning mutagenesis. J. Mol. Biol. Jul. 5, 2002, 320(2):415-28. (Year: 2002).*
Rabia et al. Understanding and overcoming trade-offs between antibody affinity, specificity, stability and solubility. Biochem Eng J. Sep. 15, 2018; 137: 365-374. (Year: 2018).*
Rudikoff et al Single amino acid substitution altering antigen-binding specificity. Proc Natl Acad Sci U S A. Mar. 1982;79(6):1979-83 (Year: 1982).*
Paul, Fundamental Immunology, 3rd Edition, 1993, pp. 292-295. (Year: 1993).*
International Search Report dated Jul. 4, 2019 for PCT/CN2019/081063.
Written Opinion dated Jul. 4, 2019 for PCT/CN2019/081063 [Non-English language].

* cited by examiner

*Primary Examiner* — Maher M Haddad
(74) *Attorney, Agent, or Firm* — Banner & Witcoff, LLP

(57) ABSTRACT

Disclosed in the present invention are an antibody targeting LAG-3, a preparation method therefor and the use thereof. In particular, disclosed in the present invention is a novel monoclonal antibody targeting LAG-3. Also disclosed in the present invention is a method for the preparation of the monoclonal antibody. The monoclonal antibody of the present invention is capable of binding LAG-3 antigens with high specificity, and has very high affinity and significant activities such as anti-tumor activity.

11 Claims, 12 Drawing Sheets
Specification includes a Sequence Listing.

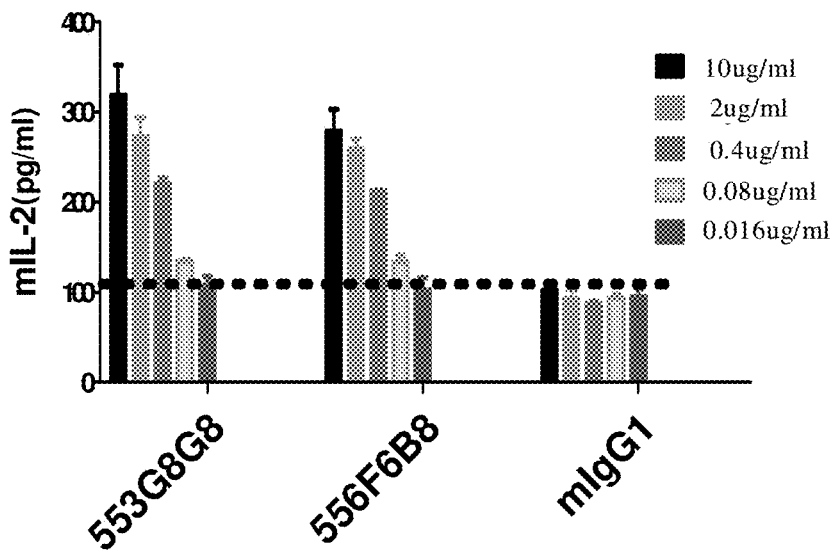

Figure 8b

```
  1 gaggtccagc tgcaacagtc tggacctgag ctggtgaagc ctggggcttc agtgaagatg tcctgcaggg cttctggata cacattcact gactt caaa
      e  v  q  l  q  q  s  g  p  e  l  v  k  p  g  a  s  v  k  m  s  c  r  a  s  g  y  t  f  t  d  f  k
                                                                                                    CDR-H1
101 tgcactggat gaagcagagc catggaaaga gccttgagtg gattggatat attgcccta acaatggtgg tactgcctac aatcagaaat tcaaggacaa
      c  t  w  m  k  q  s  h  g  k  s  l  e  w  i  g  y  i  a  p  n  n  g  t  a  y  n  q  k  f  k  g
                                                                                              CDR-H2
201 ggccacattg actgtaaacg agtcctccaa cacagcctac atggagctcc gcagcctgac atcggaagat tctgcagtct attactgtgt ggactggac
      a  t  l  t  v  n  e  s  s  n  t  a  y  m  e  l  r  s  l  t  s  e  d  s  a  v  y  y  c  v  d  w  d
301 gacgttgact actgggggca aggcaccact ctcacagtct cctca
      d  v  d  y  w  g  q  g  t  t  l  t  v  s  s
      CDR-H3
```

Figure 9a

```
  1 gacatcaaga tgacccagtc tccatcttcc atgtatgcat ctctaggaga gagagtcact atcacttgca aggcaagtca ggacattaat agctatttaa
      d  i  k  m  t  q  s  p  s  s  m  y  a  s  l  g  e  r  v  t  i  t  c  k  a  s  q  d  i  n  s  y  l
                                                                                        CDR-L1
101 gctggttcca gcagaaatca gggaaatctc taagaccct gatctatcgt gcaaatagat tggtagatgg ggtcccatca aggttcagtg gcagtggatc
      s  w  f  q  q  k  s  g  k  s  p  k  t  l  i  y  r  a  n  r  l  v  d  g  v  p  s  r  f  s  g  s  g
                                                    CDR-L2
201 tgggcaagat tattctctca ccatcagcag cctggagtat gaagatatgg gaatttatta ttgtctacag tatgttgagt ttcctctcac gttcggtgct
      s  g  q  d  y  s  l  t  i  s  s  l  e  y  e  d  m  g  i  y  y  c  l  q  y  v  e  f  p  l  t  f  g  a
                                                                          CDR-L3
301 gggaccaagc tggagctgaa a
      g  t  k  l  e  l  k
```

Figure 9b

```
  1 caggttcaac tgcagcagtc tggggctgag ctggtgaggc ctggggcttc agtgacgctg tcctgcaagg cttcgggcta cacattcact gactatgaa
      q  v  q  l  q  q  s  g  a  e  l  v  r  p  g  a  s  v  t  l  s  c  k  a  s  g  y  t  f  t  d  y  e
                                                                                                    CDR-H1
101 tgcactgggt gaagcagaca cctgtgcatg gctggaatg gattggagct actgatcctg aaaatggtaa tagtgcctac aatcagaagt tcaaggccaa
      m  h  w  v  k  q  t  p  v  h  g  l  e  w  i  g  a  t  d  p  e  n  g  n  s  a  y  n  q  k  f  k  g
                                                                                              CDR-H2
201 ggccataatg actgcagaca aatcctccag cacagcctac atggagctcc gcagcctgac atctgaggac tctgccgtct attactgtat atcaactggg
      k  a  i  m  t  a  d  k  s  s  s  t  a  y  m  e  l  r  s  l  t  s  e  d  s  a  v  y  y  c  i  s  t  g
301 tggaatgact ggggccaagg caccagtctc acagtctcct ca
      w  n  d  w  g  q  g  t  s  l  t  v  s  s
      CDR-H3
```

ANTI-HUMAN LAG-3 MONOCLONAL ANTIBODY AND USE THEREOF

CROSS REFERENCE TO RELATED APPLICATIONS

This application is a National Stage of International Application No. PCT/CN2019/081063 filed Apr. 2, 2019, which claims benefit of Chinese Patent Application No. 201810290569.4 filed Apr. 3, 2018, both of which are herein incorporated by reference in their entirety.

SEQUENCE LISTING

The instant application contains a sequence listing which has been submitted in ASCII format via EFS-Web and is hereby incorporated by reference in its entirety. Said ASCII copy, created on Dec. 20, 2022 is named 17045166_sub-SL_.txt and is 72,423 bytes in size.

TECHNICAL FIELD

The present invention relates to the field of biomedicine, in particular to an LAG-3 antibody and a preparation method and application thereof.

BACKGROUND

Cancer immunotherapy refers to a treatment that uses the immune system to fight cancer. Recently, cancer immunotherapy has attracted much attention. It has become a new method of cancer treatment besides surgery, chemotherapy and radiotherapy. Immune checkpoints refer to some inhibitory signal pathways in the immune system, which prevent tissue damage by regulating the persistence and intensity of immune responses in peripheral tissues, and participate in maintaining tolerance to self-antigens. The use of inhibitory signaling pathways of immune checkpoints to inhibit T cell activity is an important mechanism for tumors to escape immune killing. Blocking immune checkpoints is one of many effective strategies to activate anti-tumor immunity.

Inhibitors of immune checkpoint proteins have the potential to treat various tumor types (such as metastatic melanoma, lung cancer, breast cancer, renal cell carcinoma, etc.). Recent research on cancer immunotherapy has shown promising results, especially for metastatic cancer cases. In addition, cancer immunotherapy has great potential in the treatment of blood cancers, including Hodgkin's lymphoma, multiple myeloma, myelodysplastic syndrome, and non-Hodgkin's lymphoma. The side effects caused by immune checkpoint inhibitors are negligible, reversible and controllable, and effective immune checkpoint inhibitors can significantly improve the overall survival of cancer patients. Immune checkpoint inhibitors can also be used in combination with targeted therapy or conventional radiotherapy and chemotherapy, and this combination therapy can effectively treat many types of cancer, and may be the hope of treating or curing a variety of cancers.

Lymphocyte activating gene (LAG-3, CD223) is a type I membrane protein with 525 amino acids and is one of the major known immune checkpoints. Studies have shown that LAG-3−/− C57BL/6 mice exhibit a relatively normal phenotype over a period of time, indicating that LAG-3 has a subtle regulatory role in the immune system and may play a fine-tuned role in the immune response. In vivo animal model experiments have shown that using anti-LAG-3 antibodies or genetically knocking out the LAG-3 gene can enhance the activity of antigen-specific CD8+ T cells at the tumor site, thereby blocking tumor growth. Studies by Grosso J F and others have shown that LAG-3 and human programmed death receptor-1 (PD-1) are co-expressed on tolerant tumor infiltrating lymphocytes, and they work together to exert tumor-induced immunosuppressive effects. It has been proved that the combined application of anti-LAG-3 and anti-PD-1 antibodies in mouse MC38 colon adenocarcinoma and SalN fibrosarcoma models can cure most mice, and the therapeutic effect is better than that of single medication.

Based on the current small quantity of LAG-3 antibodies in research, there is an urgent need to develop LAG-3 antibodies with better activity, wide indications and high yields to further improve the therapeutic and detection effects.

SUMMARY OF THE INVENTION

In order to develop LAG-3 antibodies with good activity, wide indications and high yields, the present invention provides an LAG-3 antibody with high affinity and strong specificity and a preparation method thereof.

In a first aspect of the present invention, it provides a heavy chain variable region of an antibody, wherein the heavy chain variable region comprises the following three complementary determining regions or CDRs:
CDR1 shown in SEQ ID NO: $8n+2$,
CDR2 shown in SEQ ID NO: $8n+3$, and
CDR3 shown in SEQ ID NO: $8n+4$;
wherein, each n is independently 0, 1, 2, 3, 4 or 5;
wherein, any one of the above amino acid sequences also includes a derivative sequence that is optionally with at least one amino acid added, deleted, modified, and/or substituted, and is capable of retaining the binding affinity to LAG-3.

In another preferred embodiment, the heavy chain variable region has the amino acid sequence shown in SEQ ID NO: $8n+1$, wherein n is 0, 1, 2, 3, 4 or 5.

In another preferred embodiment, the heavy chain variable region has the amino acid sequence shown in SEQ ID NO: 64, SEQ ID NO: 66, SEQ ID NO: 68, SEQ ID NO: 70, or SEQ ID NO: 72.

In another preferred embodiment, the heavy chain variable region has the amino acid sequence shown in SEQ ID NO: 87, SEQ ID NO: 91, SEQ ID NO: 92, or SEQ ID NO: 93.

In a second aspect of the present invention, it provides a heavy chain of an antibody, wherein the heavy chain comprises the heavy chain variable region according to the first aspect of the present invention.

In a third aspect of the present invention, it provides a light chain variable region of an antibody, wherein the light chain variable region comprises the following three complementary determining regions or CDRs:
CDR1' shown in SEQ ID NO: $8n+6$,
CDR2' shown in SEQ ID NO: $8n+7$, and
CDR3' shown in SEQ ID NO: $8n+8$;
wherein, each n is independently 0, 1, 2, 3, 4 or 5;
wherein, any one of the above amino acid sequences also includes a derivative sequence that is optionally with at least one amino acid added, deleted, modified, and/or substituted, and is capable of retaining the binding affinity to LAG-3.

In another preferred embodiment, the VL-CDR2 of the light chain variable region has the amino acid sequence shown in SEQ ID NO: 84 (VL-CDR2 of 405B81-13-1 (D→E)).

In another preferred embodiment, the light chain variable region has the amino acid sequence shown in SEQ ID NO: 8n+5, wherein n is 0, 1, 2, 3, 4 or 5.

In another preferred embodiment, the light chain variable region has the amino acid sequence shown in SEQ ID NO: 74, SEQ ID NO: 76, SEQ ID NO: 78, SEQ ID NO: 80, or SEQ ID NO: 82.

In another preferred embodiment, the light chain variable region has the amino acid sequence shown in SEQ ID NO: 89 or SEQ ID NO: 95.

In a fourth aspect of the present invention, it provides a light chain of an antibody, wherein the light chain comprises the light chain variable region according to the third aspect of the present invention.

In a fifth aspect of the present invention, it provides an antibody, wherein the antibody comprises:

(1) the heavy chain variable region according to the first aspect of the present invention; and/or (2) the light chain variable region according to the third aspect of the present invention;

or the antibody comprises: the heavy chain according to the second aspect of the present invention; and/or the light chain according to the fourth aspect of the present invention, wherein, any one of the above amino acid sequences also includes a derivative sequence that is optionally with at least one amino acid added, deleted, modified, and/or substituted, and is capable of retaining the binding affinity to LAG-3.

In another preferred embodiment, the amino acid sequence of any of the above-mentioned CDRs includes a derivative CDR sequence with 1, 2 or 3 amino acids added, deleted, modified and/or substituted, and the derivative antibody comprising the VH and VL containing the derivative CDR sequence can retain the binding affinity to LAG-3.

In another preferred embodiment, the ratio (F1/F0) of the binding affinity F1 of the derivatized antibody to LAG-3 with the binding affinity F0 of the corresponding non-derivatized antibody to LAG-3 is 0.5-2, preferably 0.7-1.5, and more preferably 0.8-1.2.

In another preferred embodiment, the number of added, deleted, modified and/or substituted amino acids is 1-5 (such as 1-3, preferably 1-2, more preferably 1).

In another preferred embodiment, the derivative sequence with at least one amino acid added, deleted, modified, and/or substituted, which can retain the binding affinity to LAG-3, is an amino acid sequence having a homology of at least 96%.

In another preferred embodiment, the antibody further comprises a heavy chain constant region and/or a light chain constant region.

In another preferred embodiment, the heavy chain constant region is of murine origin, and/or the light chain constant region is of murine origin.

In another preferred embodiment, the heavy chain constant region is of human origin, and/or the light chain constant region is of human origin.

In another preferred embodiment, the heavy chain variable region of the antibody further comprises a human-derived framework region, and/or the light chain variable region of the antibody further comprises a human-derived framework region.

In another preferred embodiment, the heavy chain variable region of the antibody further comprises a murine-derived framework region, and/or the light chain variable region of the antibody further comprises a murine-derived framework region.

In another preferred embodiment, the antibody is selected from: chimeric antibodies, humanized antibodies, fully human antibodies, and a combination thereof.

In another preferred embodiment, the antibody is a mutant humanized antibody.

In another preferred embodiment, the antibody is a humanized antibody with a D→E mutation in the CDR region.

In another preferred embodiment, the antibody is a humanized antibody with a D→E mutation in VL-CDR2 or VH-CDR3.

In another preferred embodiment, the ratio (Z1/Z0) of the immunogenicity Z1 of the fully human antibody in human to the immunogenicity Z0 of the non-fully human antibody (such as murine-derived antibody) in human is 0-0.5, preferably 0-0.2, more preferably 0-0.05 (e.g. 0.001-0.05).

In another preferred embodiment, the antibody is a partially or fully humanized or fully human monoclonal antibody.

In another preferred embodiment, the antibody is a double-chain antibody or a single-chain antibody.

In another preferred embodiment, the antibody is a full-length antibody protein or an antigen-binding fragment.

In another preferred embodiment, the antibody is a bispecific antibody or a multispecific antibody.

In another preferred embodiment, the antibody has one or more properties selected from the following group:

(a) inhibiting tumor cell migration or metastasis;

(b) inhibiting tumor growth.

In another preferred embodiment, the antibody comprises the heavy chain variable region according to the first aspect of the present invention and the light chain variable region according to the third aspect of the present invention; wherein, the heavy chain variable region comprises the following three complementary determining regions or CDRs:

CDR1 shown in SEQ ID NO: 2,
CDR2 shown in SEQ ID NO: 3, and
CDR3 shown in SEQ ID NO: 4;
the light chain variable region comprises the following three complementary determining regions or CDRs:
CDR1' shown in SEQ ID NO: 6,
CDR2' shown in SEQ ID NO: 7 or SEQ ID NO: 84, and
CDR3' shown in SEQ ID NO: 8;
or
the heavy chain variable region comprises the following three complementary determining regions or CDRs:
CDR1 shown in SEQ ID NO: 10,
CDR2 shown in SEQ ID NO: 11, and
CDR3 shown in SEQ ID NO: 12;
the light chain variable region comprises the following three complementary determining regions or CDRs:
CDR1' shown in SEQ ID NO: 14,
CDR2' shown in SEQ ID NO: 15, and
CDR3' shown in SEQ ID NO: 16;
or
the heavy chain variable region comprises the following three complementary determining regions or CDRs:
CDR1 shown in SEQ ID NO: 18,
CDR2 shown in SEQ ID NO: 19, and
CDR3 shown in SEQ ID NO: 20;
the light chain variable region comprises the following three complementary determining regions or CDRs:
CDR1' shown in SEQ ID NO: 22,
CDR2' shown in SEQ ID NO: 23, and
CDR3' shown in SEQ ID NO: 24;

wherein, any one of the above amino acid sequences also includes a derivative sequence that is optionally with at least one amino acid added, deleted, modified, and/or substituted, and is capable of retaining the binding affinity to LAG-3.

In another preferred embodiment, the heavy chain variable region of the antibody comprises the amino acid sequence shown in SEQ ID NO: 8n+1; and/or the light chain variable region of the antibody comprises the amino acid sequence shown in SEQ ID NO: 8n+5, wherein each n is independently 0, 1, 2, 3, 4, or 5.

In another preferred embodiment, the heavy chain variable region of the antibody has the amino acid sequence shown in SEQ ID NO: 1.

In another preferred embodiment, the light chain variable region of the antibody has the amino acid sequence shown in SEQ ID NO: 5.

In another preferred embodiment, the heavy chain variable region of the antibody has the amino acid sequence shown in SEQ ID NO: 9.

In another preferred embodiment, the light chain variable region of the antibody has the amino acid sequence shown in SEQ ID NO: 13.

In another preferred embodiment, the heavy chain variable region of the antibody has the amino acid sequence shown in SEQ ID NO: 17.

In another preferred embodiment, the light chain variable region of the antibody has the amino acid sequence shown in SEQ ID NO: 21.

In another preferred embodiment, the heavy chain variable region of the antibody has the amino acid sequence shown in SEQ ID NO: 1, and the light chain variable region of the antibody has the amino acid sequence shown in SEQ ID NO: 5; or the heavy chain variable region of the antibody has the amino acid sequence shown in SEQ ID NO: 9, and the light chain variable region of the antibody has the amino acid sequence shown in SEQ ID NO: 13; or the heavy chain variable region of the antibody has the amino acid sequence shown in SEQ ID NO: 17, and the light chain variable region of the antibody has the amino acid sequence shown in SEQ ID NO: 21.

In another preferred embodiment, the heavy chain variable region of the antibody has the amino acid sequence shown in SEQ ID NO: 25, and the light chain variable region of the antibody has the amino acid sequence shown in SEQ ID NO: 29.

In another preferred embodiment, the heavy chain variable region of the antibody has the amino acid sequence shown in SEQ ID NO: 33, and the light chain variable region of the antibody has the amino acid sequence shown in SEQ ID NO: 37.

In another preferred embodiment, the heavy chain variable region of the antibody has the amino acid sequence shown in SEQ ID NO: 41, and the light chain variable region of the antibody has the amino acid sequence shown in SEQ ID NO: 45.

In another preferred embodiment, the heavy chain variable region of the antibody has the amino acid sequence shown in SEQ ID NO: 64, and the light chain variable region of the antibody has the amino acid sequence shown in SEQ ID NO: 74.

In another preferred embodiment, the heavy chain variable region of the antibody has the amino acid sequence shown in SEQ ID NO: 64, and the light chain variable region of the antibody has the amino acid sequence shown in SEQ ID NO: 76.

In another preferred embodiment, the heavy chain variable region of the antibody has the amino acid sequence shown in SEQ ID NO: 66, and the light chain variable region of the antibody has the amino acid sequence shown in SEQ ID NO: 76.

In another preferred embodiment, the heavy chain variable region of the antibody has the amino acid sequence shown in SEQ ID NO: 66, and the light chain variable region of the antibody has the amino acid sequence shown in SEQ ID NO: 78.

In another preferred embodiment, the heavy chain variable region of the antibody has the amino acid sequence shown in SEQ ID NO: 68, and the light chain variable region of the antibody has the amino acid sequence shown in SEQ ID NO: 78.

In another preferred embodiment, the heavy chain variable region of the antibody has the amino acid sequence shown in SEQ ID NO: 70, and the light chain variable region of the antibody has the amino acid sequence shown in SEQ ID NO: 80.

In another preferred embodiment, the heavy chain variable region of the antibody has the amino acid sequence shown in SEQ ID NO: 72, and the light chain variable region of the antibody has the amino acid sequence shown in SEQ ID NO: 80.

In another preferred embodiment, the heavy chain variable region of the antibody has the amino acid sequence shown in SEQ ID NO: 72, and the light chain variable region of the antibody has the amino acid sequence shown in SEQ ID NO: 82.

In another preferred embodiment, the antibody is selected from the group consisting of: 405B81-13, 556F6B8, 105F1E10, 409B11E12, 409D4E10, and 553G8G8.

In another preferred embodiment, the antibody is selected from the group consisting of: 405B81-13-1 (D→E), 405B81-13-1, 405B8113-2, 405B813-6, 405B81-13-7, 556F6B8-3, 556F6B8-7, and 556F6B8-3 (D→E).

In another preferred embodiment, the amino acid sequence of the heavy chain variable region has a sequence homology or identity of at least 80%, 85%, 90%, 91%, 92%, 93%, 94%, 95%, 96%, 97%, 98% or 99% with the amino acid sequence shown in SEQ ID NO: 1, SEQ ID NO: 9, SEQ ID NO: 17, SEQ ID NO: 25, SEQ ID NO: 33, SEQ ID NO: 41, SEQ ID NO: 64, SEQ ID NO: 66, SEQ ID NO: 68, SEQ ID NO: 70 or SEQ ID NO: 72 in the sequence listing.

In another preferred embodiment, the amino acid sequence of the light chain variable region has a sequence homology or identity of at least 80%, 85%, 90%, 91%, 92%, 93%, 94%, 95%, 96%, 97%, 98% or 99% with the amino acid sequence shown in SEQ ID NO: 5, SEQ ID NO: 13, SEQ ID NO: 21, SEQ ID NO: 29, SEQ ID NO: 37, SEQ ID NO: 45, SEQ ID NO: 74, SEQ ID NO: 76, SEQ ID NO: 78, SEQ ID NO: 80 or SEQ ID NO: 82 in the sequence listing.

In a sixth aspect of the present invention, it provides a recombinant protein, wherein the recombinant protein comprises:

(i) the heavy chain variable region according to the first aspect of the present invention, the heavy chain according to the second aspect of the present invention, the light chain variable region according to the third aspect of the present invention, the light chain according to the fourth aspect of the present invention, or the antibody according to any one of the fifth aspect of the present invention; and (ii) an optional tag sequence to assist expression and/or purification.

In another preferred embodiment, the tag sequence includes a 6His tag.

In another preferred embodiment, the recombinant protein (or polypeptide) includes a fusion protein.

In another preferred embodiment, the recombinant protein is a monomer, dimer, or multimer.

In another preferred embodiment, the recombinant protein comprises:

(i) the antibody according to the fifth aspect of the present invention, and (ii) an optional tag sequence to assist expression and/or purification.

In a seventh aspect of the present invention, it provides a polynucleotide, which encodes a polypeptide selected from the group consisting of:

(1) the heavy chain variable region according to the first aspect of the present invention, the heavy chain according to the second aspect of the present invention, the light chain variable region according to the third aspect of the present invention, the light chain according to the fourth aspect of the present invention, or the antibody according to any one of the fifth aspect of the present invention; and (2) the recombinant protein according to the sixth aspect of the present invention.

In another preferred embodiment, the polynucleotide encoding the heavy chain variable region is shown in SEQ ID NO: 49, 51, 53, 55, 57, 59, 65, 67, 69, 71 or 73; and/or, the polynucleotide encoding the light chain variable region is shown in 50, 52, 54, 56, 58, 60, 75, 77, 79, 81 or 83.

In another preferred embodiment, the polynucleotide encoding the heavy chain variable region sequence is shown in SEQ ID NO: 49; and the polynucleotide encoding the light chain variable region sequence is shown in 50; or the polynucleotide encoding the heavy chain variable region is shown in SEQ ID NO: 51; and the polynucleotide encoding the light chain variable region is shown in 52; or the polynucleotide encoding the heavy chain variable region is shown in SEQ ID NO: 53; and the polynucleotide encoding the light chain variable region is shown in 54.

In another preferred embodiment, the polynucleotide encoding the heavy chain variable region is shown in SEQ ID NO: 55; and the polynucleotide encoding the light chain variable region is shown in 56.

In another preferred embodiment, the polynucleotide encoding the heavy chain variable region is shown in SEQ ID NO: 57; and the polynucleotide encoding the light chain variable region is shown in 58.

In another preferred embodiment, the polynucleotide encoding the heavy chain variable region is shown in SEQ ID NO: 59; and the polynucleotide encoding the light chain variable region is shown in 60.

In an eighth aspect of the present invention, it provides a vector, which contains the polynucleotide according to any one of the seventh aspect of the present invention.

In another preferred embodiment, the vector includes: bacterial plasmid, phage, yeast plasmid, plant cell virus, mammalian cell virus such as adenovirus, retrovirus, or other vectors.

In a ninth aspect of the present invention, it provides a genetically engineered host cell, wherein the host cell contains the vector according to the eighth aspect of the present invention or the genome thereof is integrated with the polynucleotide according to any one of the seventh aspect of the present invention.

In a tenth aspect of the present invention, it provides a pharmaceutical composition, wherein the pharmaceutical composition comprises:

(i) an active ingredient, wherein the active ingredient is selected from the group consisting of: the heavy chain variable region according to the first aspect of the present invention, the heavy chain according to the second aspect of the present invention, the light chain variable region according to the third aspect of the present invention, the light chain according to the fourth aspect of the present invention, and the antibody according to any one of the fifth aspect of the present invention, the recombinant protein according to the sixth aspect of the present invention, and combinations thereof; and (ii) a pharmaceutically acceptable carrier.

In another preferred embodiment, the pharmaceutical composition is a liquid preparation.

In another preferred embodiment, the pharmaceutical composition is an injection.

In another preferred embodiment, the pharmaceutical composition comprises 0.01-99.99% of the antibody according to any one of the fifth aspect of the present invention, the recombinant protein according to the sixth aspect of the present invention, or a combination thereof, and 0.01-99.99% of the pharmaceutically acceptable carrier, wherein the percentage is the mass percentage of the pharmaceutical composition.

In an eleventh aspect of the present invention, it provides use of an active ingredient, wherein the active ingredient is selected from the group consisting of: the heavy chain variable region according to the first aspect of the present invention, the heavy chain according to the second aspect of the present invention, the light chain variable region according to the third aspect of the present invention, the light chain according to the fourth aspect of the present invention, and the antibody according to any one of the fifth aspect of the present invention, the recombinant protein according to the sixth aspect of the present invention, and combinations thereof, wherein the active ingredient is used for preparation of a medicine for preventing and/or treating LAG-3 related diseases.

In another preferred embodiment, the LAG-3 related diseases include, but are not limited to the following group: melanoma (such as metastatic malignant melanoma), kidney cancer, prostate cancer, breast cancer, colon cancer, lung cancer (such as non-small cell lung cancer), uterine cancer, ovarian cancer, rectal cancer, stomach cancer, esophageal cancer, small intestine cancer, liver cancer, bladder cancer, oral cancer, brain cancer, testicular cancer, skin cancer, endocrine system cancer, fallopian tube cancer, chronic or acute leukemia (including acute or chronic myeloid leukemia, acute or chronic lymphocytic leukemia), lymphocytic lymphoma, primary CNS lymphoma, T cell lymphoma, and advanced solid tumors.

In a twelfth aspect of the present invention, it provides a composition for detecting LAG-3 protein in a sample in vitro, which comprises the antibody according to any one of the fifth aspect of the present invention, and the recombinant protein according to the sixth aspect of the present invention, or a combination thereof, used as an active ingredient.

In a thirteenth aspect of the present invention, it provides a method for preparing a recombinant polypeptide, wherein the method comprises:

(a) culturing the host cell according to the ninth aspect of the present invention under conditions suitable for expression;

(b) isolating a recombinant polypeptide from the culture, wherein the recombinant polypeptide is the antibody according to any one of the fifth aspect of the present invention or the recombinant protein according to the sixth aspect of the present invention.

In a fourteenth aspect of the present invention, it provides a method for treating LAG-3 related diseases, comprising: using the antibody according to any one of the fifth aspect of the present invention, the recombinant protein according to the sixth aspect of the present invention, the pharmaceutical composition according to the tenth aspect of the present invention, or a combination thereof.

In another preferred embodiment, the LAG-3 related disease is cancer.

In another preferred embodiment, a second antibody is also used.

In another preferred embodiment, the second antibody is selected from the group consisting of PD-1 antibody, CTLA-4 antibody, and PDL-1 antibody.

In a fifteenth aspect of the present invention, it provides a drug combination, including:
  (i) a first active ingredient, which is the antibody according to any one of the fifth aspect of the present invention;
  (ii) a second active ingredient, which includes a second antibody.

In a sixteenth aspect of the present invention, it provides use of a combination of the antibody according to any one of the fifth aspect of the present invention, or the recombinant protein according to the sixth aspect of the present invention, or the pharmaceutical composition according to the tenth aspect of the present invention, and a second antibody, for the preparation of a medicine for treating LAG-3 related diseases.

It should be understood that within the scope of the present invention, the various technical features of the present invention above and the various technical features specifically described hereinafter (as in the embodiments) may be combined with each other to constitute a new or preferred technical solution. Due to space limitations, it is not repeated here.

DESCRIPTION OF THE FIGURES

FIG. 8b shows the effect of LAG-3 antibodies on IL-2 secretion in the antigen-specific T lymphocyte stimulation test.

FIG. 9a shows protein and gene sequences of LAG-3 antibody 105F1E10 heavy chain variable region (SEQ ID NO: 17 is the amino acid sequence, and SEQ ID NO: 53 is the nucleotide sequence).

FIG. 9b shows protein and gene sequences of LAG-3 antibody 105F1E10 light chain variable region (SEQ ID NO: 21 is the amino acid sequence, and SEQ ID NO: 54 is the nucleotide sequence).

Figures 10B, 11A, 11B, 12A, 12B:
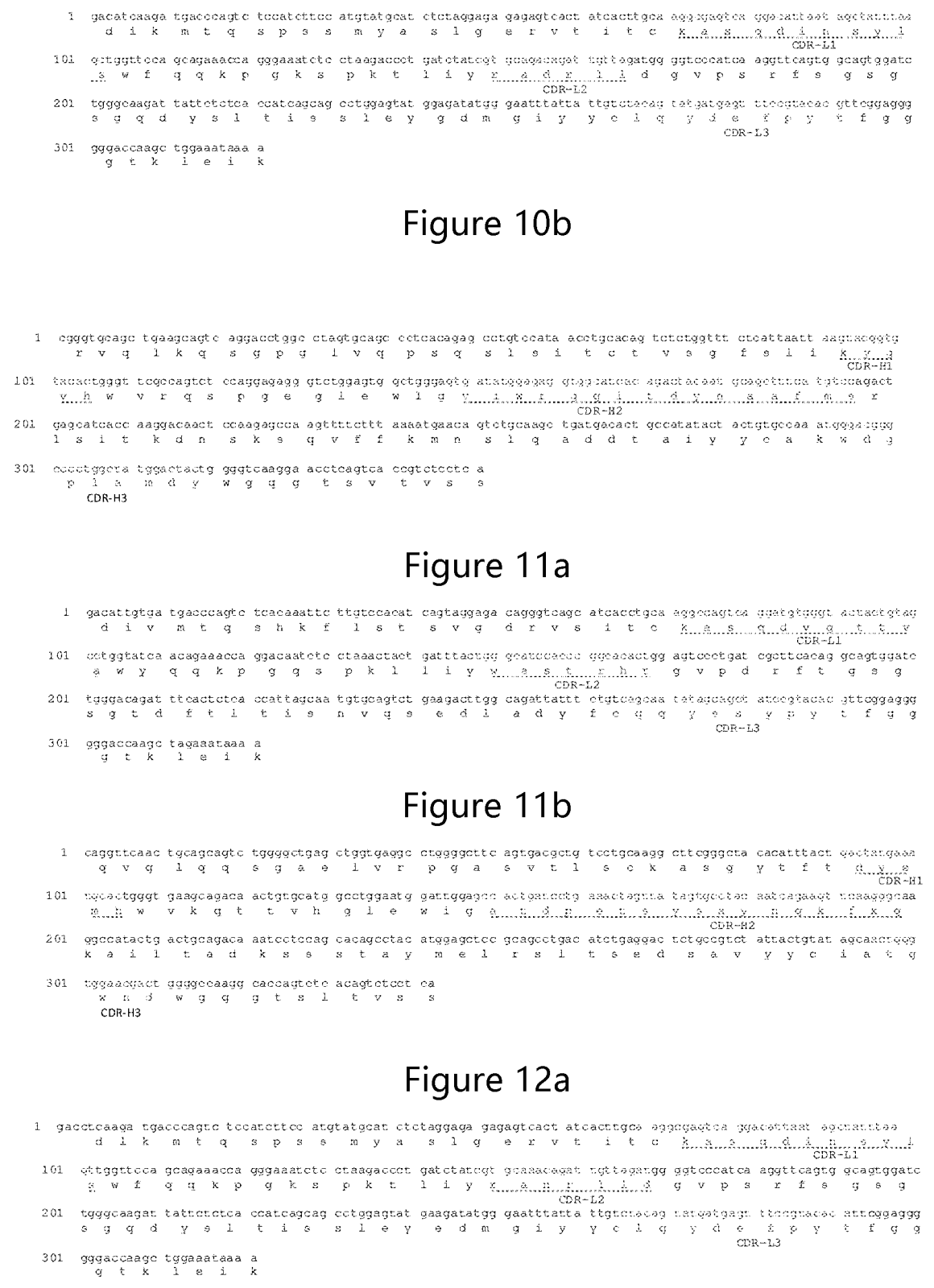

FIG. 10a shows protein and gene sequences of LAG-3 antibody 405B8H3 heavy chain variable region (SEQ ID NO: 1 is the amino acid sequence, and SEQ ID NO: 49 is the nucleotide sequence).

FIG. 10b shows protein and gene sequences of LAG-3 antibody 405B8H3 light chain variable region (SEQ ID NO: 5 is the amino acid sequence, and SEQ ID NO: 50 is the nucleotide sequence).

FIG. 11a shows protein and gene sequences of LAG-3 antibody 556F6B8 heavy chain variable region (SEQ ID NO: 9 is the amino acid sequence, and SEQ ID NO: 51 is the nucleotide sequence).

FIG. 11b shows protein and gene sequences of LAG-3 antibody 556F6B8 light chain variable region (SEQ ID NO: 13 is the amino acid sequence, and SEQ ID NO: 52 is the nucleotide sequence).

FIG. 12a shows protein and gene sequences of LAG-3 antibody 409B11E12 heavy chain variable region (SEQ ID NO: 25 is the amino acid sequence, and SEQ ID NO: 55 is the nucleotide sequence).

FIG. 12b shows protein and gene sequences of LAG-3 antibody 409B11E12 light chain variable region (SEQ ID NO: 29 is the amino acid sequence, and SEQ ID NO: 56 is the nucleotide sequence).

DETAILED DESCRIPTION

Figure 1:
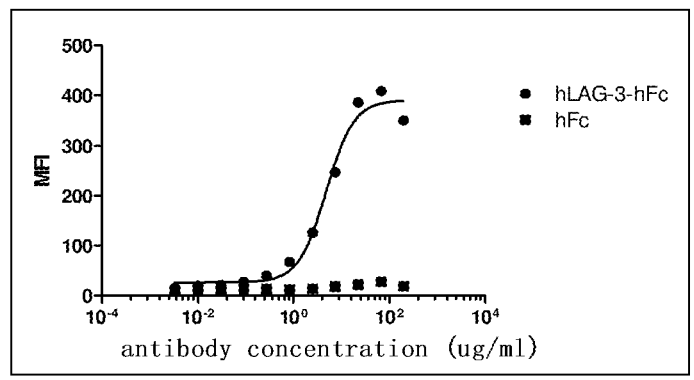
FIG. 1 shows the binding activity of LAG-3-hFc protein and its ligand MHCII.

By extensively and intensively studies, using immune mouse/hybridoma technology, the inventors unexpectedly obtained a highly active specific monoclonal antibody (mouse antibody) that binds to human lymphocyte activation gene (LAG-3). Experimental results show that the antibodies of the present invention (mouse-human chimeric antibody) has a high affinity with the antigen protein (for example, 405B8H3 has a $K_D$ of 1.96E-09M), and they can bind the extracellular region of LAG-3 receptor and can effectively block the binding of LAG-3 to the ligand MHC class II and LSECtin at the protein and cell levels. The antigen-specific T lymphocyte stimulation experiment proves that the LAG-3 antibodies obtained has good biological activity. Use of the antibody of the present invention includes but is not limited to inhibiting the negative regulation of LAG-3/MHC II and/or LAG-3/LSECtin mediated signaling pathways, activating tumor-specific immune responses, used in tumor immunotherapy alone or in combination with anti-PD-1, CTLA-4 monoclonal antibody or other anti-tumor drugs.

The variable region of the antibody of the present invention and the constant region of a human antibody are combined into a mouse-human chimeric antibody molecule, or converted into a humanized antibody molecule through humanization technology, or constructed into other molecular forms such as bispecific antibodies, multispecific antibodies, single chain antibodies, single fragment antibodies, etc. according to specific purposes.

The antibody in the present invention can be a full-length protein (such as IgG1, IgG2a, IgG2b or IgG2c), or a protein fragment containing an antigen-antibody binding domain (such as Fab, F(ab'), sdAb, ScFv fragments). The antibody in the present invention can be a wild-type protein, or a mutant protein that has achieved a certain effect through specific mutations, for example, using mutations to eliminate the effector function of the antibody.

On this basis, the present invention has been completed.

The Terms

LAG-3

Lymphocyte activating gene (LAG-3, CD223) is a type I membrane protein with 525 amino acids and is one of the major known immune checkpoints. LAG-3 is mainly expressed in activated T lymphocytes, NK cells and dendritic cells. LAG-3 belongs to the immunoglobulin superfamily in structure. It has 4 IgG-like domains outside the cell. Similar to CD4, it needs to interact with the ligand, major histocompatibility complex class II (MHC class II), to exert its biological activity, but its binding ability to MHC II is stronger than that of CD4. The binding of LAG-3 and its ligand MHC class II can inhibit the activation and proliferation of CD4+T lymphocytes, and then down-regulate related cellular immune responses in vivo. In the study of antigen-specific T cell response in vitro, adding the anti-LAG-3 antibody to block the negative regulation of the LAG-3/MHC II signaling pathway can lead to T cell proliferation and promote the secretion of cytokines, and activate the immune system. In addition, LAG-3 is also expressed on regulatory T cells (Treg), promoting the Treg cell activity. In turn, it negatively regulates the activation and proliferation of T cells and the maturation of dendritic cells (DC cells) (Workman et al, 2005, Immunol, 174:688-695).

Antibody

As used herein, the term "antibody" or "immunoglobulin" is a heterotetrameric glycoprotein of about 150,000 daltons with the same structural characteristics, which consists of two identical light chains (L) and two identical heavy chains (H). Each light chain is connected to the heavy chain through a covalent disulfide bond, and the numbers of disulfide bonds between heavy chains of different immunoglobulin isotypes are different. Each heavy and light chain also has regularly spaced intrachain disulfide bonds. Each heavy chain has a variable region (VH) at one end, followed by multiple constant regions. Each light chain has a variable region (VL) at one end and a constant region at the other end; the constant region of the light chain is opposite to the first constant region of the heavy chain, and the variable region of the light chain is opposite to the variable region of the heavy chain. Special amino acid residues form an interface between the variable regions of the light and heavy chains.

As used herein, the term "variable" means that certain parts of the variable region of an antibody differ in sequence, which forms the binding and specificity of various specific antibodies for their specific antigens. However, the variability is not evenly distributed throughout the variable region of the antibody. It is concentrated in three segments called complementary determining regions (CDRs) or hypervariable regions in the light chain and heavy chain variable regions. The more conserved part of the variable region is called the framework region (FR). The variable regions of the natural heavy and light chains each contain four FR regions, which are roughly in the 3-folded configuration, connected by the three CDRs that form the connecting loop, and in some cases may form a partly folded structure.β The CDRs in each chain get close through the FR regions and together with the CDRs of the other chain form the antigen-binding site of the antibody (see Kabat et al., NIH Publ. No.

91-3242, Volume I, pages 647-669 (1991)). The constant regions are not directly involved in the binding of antibodies to antigens, but they exhibit different effector functions, such as involved in the antibody-dependent cytotoxicity of antibodies.

The light chains of vertebrate antibodies (immunoglobulins) can be classified into one of two distinct classes (referred to as x and X) based on the amino acid sequence of their constant regions. Immunoglobulins can be divided into different types, according to the amino acid sequence of the constant region of the heavy chain. There are five main classes of immunoglobulins: IgA, IgD, IgE, IgG, and IgM, some of which can be further divided into subclasses (isotypes), such as IgG1, IgG2, IgG3, IgG4, IgA, and IgA2. The heavy chain constant regions corresponding to different classes of immunoglobulins are called δ, ε, γ, α, and μ, respectively. The subunit structures and three-dimensional configurations of different classes of immunoglobulins are well known to those skilled in the art.

In general, the antigen-binding properties of an antibody can be described by the three specific regions located in the variable regions of the heavy and light chains, called complementary determining regions (CDR), which divide this segment into 4 framework regions (FR). The amino acid sequences of the four FRs are relatively conservative and do not directly participate in the binding reaction. These CDRs form a circular structure, and get close in space structure through the R sheets formed by the FRs in between. The CDRs on the heavy chain and the CDRs on the corresponding light chain constitute the antigen binding site of the antibody. The amino acid sequences of antibodies of the same type can be compared to determine which amino acids constitute the FR or CDR regions.

The present invention includes not only intact antibodies, but also immunologically active fragments of antibody fragments or fusion proteins formed by antibodies and other sequences. Therefore, the present invention also includes fragments, derivatives and analogs of the antibodies.

In the present invention, antibodies include murine, chimeric, humanized, or fully human antibodies prepared by techniques well known to those skilled in the art. Recombinant antibodies, such as chimeric and humanized monoclonal antibodies, including human and non-human parts, can be obtained by standard DNA recombination techniques, and they are all useful antibodies. A chimeric antibody is a molecule in which different parts come from different animal species, such as a chimeric antibody with a variable region of a monoclonal antibody from a mouse and a constant region from a human immunoglobulin (see, for example, U.S. Pat. Nos. 4,816,567 and 4,816,397, hereby incorporated by reference in its entirety). Humanized antibodies refer to antibody molecules derived from non-human species, having one or more complementary determining regions (CDRs) derived from non-human species and framework regions derived from human immunoglobulin molecules (see U.S. Pat. No. 5,585,089, hereby incorporated by reference in its entirety). These chimeric and humanized monoclonal antibodies can be prepared using recombinant DNA techniques well known in the art.

In the present invention, the antibody may be monospecific, bispecific, trispecific, or more multispecific.

In the present invention, the antibody of the present invention also includes conservative variants thereof, which means that compared with the amino acid sequence of the antibody of the present invention, there are at most 10, preferably at most 8, more preferably at most 5, most preferably at most 3 amino acids replaced by amino acids with the same or similar properties to form a polypeptide. These conservatively variant polypeptides are preferably produced by amino acid substitution according to Table A.

TABLE A

| Initial residue | Representative substitution | Preferred substitution |
|---|---|---|
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

Anti-LAG-3 Antibody

The present invention provides an antibody with high specificity and high affinity against LAG-3, which comprises a heavy chain and a light chain, wherein the heavy chain contains a heavy chain variable region (VH) amino acid sequence, and the light chain contains a light chain variable region (VL) amino acid sequence.

Preferably, the heavy chain variable region (VH) comprises the following three complementary determining regions or CDRs:
CDR1 shown in SEQ ID NO: 2,
CDR2 shown in SEQ ID NO: 3, and
CDR3 shown in SEQ ID NO: 4;
the light chain variable region (VL) comprises the following three complementary determining regions or CDRs:
CDR1' shown in SEQ ID NO: 6,
CDR2' shown in SEQ ID NO: 7 or SEQ ID NO: 84, and
CDR3' shown in SEQ ID NO: 8;
wherein, any one of the above amino acid sequences also includes a derivative sequence that is optionally with at least one amino acid added, deleted, modified, and/or substituted, and is capable of retaining the binding affinity to LAG-3.

In another preferred embodiment, the sequence with at least one amino acid added, deleted, modified and/or substituted in any of the above amino acid sequences is preferably an amino acid sequence having a homology or sequence identity of at least 80%, more preferably at least 85%, more preferably at least 90%, most preferably at least 95% to the above amino acid sequence.

Methods known to those of ordinary skill in the art for determining sequence homology or identity include, but are not limited to: Computational Molecular Biology, Lesk, A. M., Oxford University Press, New York, 1988; Biocomputing: Informatics and Genome Projects, edited by Smith, D. W., Academic Press, New York, 1993; Computer Analysis of Sequence Data, Part I, edited by Griffin, A. M. and Griffin, H. G., Humana Press, New Jersey, 1994; Sequence Analysis in Molecular Biology, von Heinje, G., Academic Press, 1987, and Sequence Analysis Primer, edited by Gribskov, M. and Devereux, J., Stockton Press, New York, 1991, and Carillo, H. and Lipman, D., SIAM J. Applied Math., 48:1073 (1988). The preferred method of determining identity is to obtain the greatest match between the sequences tested. The method of determining identity is compiled in a publicly available computer program. Preferred computer program methods for determining the identity between two sequences include, but are not limited to: GCG package (Devereux, J. et al., 1984), BLASTP, BLASTN, and FASTA (Altschul, S, F. et al., 1990). The BLASTX program is available to the public from NCBI and other sources (BLAST Manual, Altschul, S. et al., NCBI NLM NIH Bethesda, Md. 20894; Altschul, S. et al., 1990). The well-known Smith Waterman algorithm can also be used to determine identity.

The antibody of the present invention may be a double-chain or single-chain antibody, and may be selected from animal-derived antibodies, chimeric antibodies and humanized antibodies, more preferably be selected from humanized antibodies and human-animal chimeric antibodies, more preferably a fully humanized antibody.

The antibody derivatives of the present invention may be single chain antibodies, and/or antibody fragments, such as: Fab, Fab', (Fab')2 or other known antibody derivatives in the art, etc., as well as any one or several of IgA, IgD, IgE, IgG and IgM antibodies or other subtypes.

Wherein, the animal is preferably a mammal, such as a mouse.

The antibody of the present invention may be a chimeric antibody, a humanized antibody, a CDR grafted and/or modified antibody targeting human LAG-3.

In the above content of the present invention, the number of added, deleted, modified and/or substituted amino acids is preferably not more than 40% of the total number of amino acids in the original amino acid sequence, more preferably not more than 35%, more preferably 1-33%, more preferably 5-30%, more preferably 10-25%, more preferably 15-20%.

In the above content of the present invention, more preferably, the number of added, deleted, modified and/or substituted amino acids may be 1-7, more preferably 1-5, more preferably 1-3, more preferably 1-2.

In another preferred example, the antibody targeting LAG-3 is 405B81-13, 556F6B8, 105F1E10, 409B11E12, 409D4E10 or 553G8G8.

In another preferred embodiment, the antibody is selected from the following group: 405B81-13-1 (D→E), 405B81-13-1, 405B8113-2, 405B813-6, 405B8113-7, 556F6B8-3, 556F6B8-7, and 556F6B8-3 (D→E).

In another preferred embodiment, the heavy chain variable region has the amino acid sequence shown in SEQ ID NO: 64, SEQ ID NO: 66, SEQ ID NO: 68, SEQ ID NO: 70, or SEQ ID NO: 72.

In another preferred embodiment, the heavy chain variable region has the amino acid sequence shown in SEQ ID NO: 87, SEQ ID NO: 91, SEQ ID NO: 92, or SEQ ID NO: 93.

In another preferred embodiment, the light chain variable region has the amino acid sequence shown in SEQ ID NO: 74, SEQ ID NO: 76, SEQ ID NO: 78, SEQ ID NO: 80, or SEQ ID NO: 82.

In another preferred embodiment, the light chain variable region has the amino acid sequence shown in SEQ ID NO: 89 or SEQ ID NO: 95.

In another preferred embodiment, the amino acid sequence of the heavy chain variable region (VH) of the antibody 405B81-13 is the amino acid sequence shown in SEQ ID NO: 1.

In another preferred example, the amino acid sequence of the light chain variable region of the antibody 405B81-13 is the amino acid sequence shown in SEQ ID NO: 5.

In another preferred example, the amino acid sequence of the heavy chain variable region (VH) of the antibody 405B81-13-1 (D→E) is the amino acid sequence shown in SEQ ID NO: 64.

In another preferred example, the amino acid sequence of the light chain variable region (VL) of the antibody 405B8H3-1 (D→E) is the amino acid sequence shown in SEQ ID NO: 74.

Preparation of Antibodies

The sequence of the DNA molecule for the antibody or a fragment thereof according to the present invention can be obtained by conventional techniques, for example, methods such as PCR amplification or genomic library screening. In addition, the sequences encoding light chain and heavy chain can be fused together, to form a single-chain antibody.

Once a relevant sequence is obtained, recombination methods can be used to obtain the relevant sequence in large quantities. This is usually carried out by cloning the sequence into a vector, transforming a cell with the vector, and then separating the relevant sequence from the proliferated host cell by conventional methods.

In addition, a relevant sequence can be synthesized artificially, especially when the fragment is short in length. Usually, several small fragments are synthesized first, and then are linked together to obtain a fragment with a long sequence.

It has been possible now to obtain a DNA sequence encoding the antibody (or a fragment thereof, or a derivative thereof) according to the present invention completely by chemical synthesis. Then, the DNA sequence can be introduced into various existing DNA molecules (or, for example, vectors) and cells known in the art. In addition, mutations can also be introduced into the protein sequence according to the present invention by chemical synthesis.

The present invention further relates to a vector comprising said suitable DNA sequence and a suitable promoter or a control sequence. These vectors can be used to transform suitable host cells to enable them to express protein.

The host cell can be a prokaryotic cell, such as a bacterial cell; or a lower eukaryotic cell, such as a yeast cell; or a higher eukaryotic cell, such as a mammalian cell. Preferred animal cells include, but are not limited to, CHO-S, HEK-293 cells.

In general, under conditions suitable for expression of the antibody according to the present invention, the host cell obtained is cultured. Then, the antibody according to the present invention is purified by using conventional immunoglobulin purification steps, for example, the conventional separation and purification means well known to those skilled in the art, such as protein A-Sepharose, hydroxyapatite chromatography, gel electrophoresis, dialysis, ion exchange chromatography, hydrophobic chromatography, molecular sieve chromatography or affinity chromatography.

The monoclonal antibody obtained can be identified by conventional means. For example, the binding specificity of a monoclonal antibody can be determined by immunoprecipitation or an in vitro binding assay (such as radioimmunoassay (RIA) or enzyme-linked immunosorbent assay (ELISA)). The binding affinity of a monoclonal antibody can be determined by, for example, the Scatchard analysis (Munson et al., Anal. Biochem., 107: 220 (1980)).

The antibody according to the present invention can be expressed in a cell or on the cell membrane, or is secreted extracellularly. If necessary, the recombinant protein can be separated and purified by various separation methods according to its physical, chemical, and other properties. These methods are well known to those skilled in the art. Examples of these methods include, but are not limited to, conventional renaturation treatment, treatment with a protein precipitant (salting out method), centrifugation, osmotic bacteria disruption, ultrasonic treatment, ultracentrifugation, molecular sieve chromatography (gel filtration), adsorption chromatography, ion exchange chromatography, high performance liquid chromatography (HPLC), various other liquid chromatographic techniques, and combinations of these methods.

Uses

The present invention further provides use of the antibody according to the present invention, for example, for manufacture of a diagnostic agent, or for manufacture of a medicament for preventing and/or treating a LAG-3 related disease. The LAG-3 related diseases include tumorigenesis, tumor growth, and/or metastasis related diseases.

The uses of the antibody of the present invention include (but not limited to):

(i) diagnosis, prevention and/or treatment of melanoma (such as metastatic malignant melanoma), kidney cancer, prostate cancer, breast cancer, colon cancer, lung cancer (such as non-small cell lung cancer), uterine cancer, ovarian cancer, rectal cancer, stomach cancer, esophageal cancer, small intestine cancer, liver cancer, bladder cancer, oral cancer, brain cancer, testicular cancer, skin cancer, endocrine system cancer, fallopian tube cancer, chronic or acute leukemia (including acute or chronic myeloid leukemia, acute or chronic lymphocytic leukemia), lymphocytic lymphoma, primary CNS lymphoma, T cell lymphoma, and advanced solid tumors.

Pharmaceutical Composition

The present invention further provides a composition. In the preferred examples, the composition is a pharmaceutical composition comprising the antibody, or an active fragment, a fusion protein thereof, or a corresponding CAR-T cell, and a pharmaceutically acceptable carrier. In general, these substances may be formulated in a non-toxic, inert and pharmaceutically acceptable aqueous carrier medium, wherein the pH is generally about 5-8, preferably, pH is about 6-8, though the pH value may be varied depending on the nature of the substances to be formulated and the condition to be treated. The formulated pharmaceutical composition may be administered by conventional routes, including (but not limited to): intratumoral, intraperitoneal, intravenous, or topical administration.

The antibody of the present invention can also be used for cell therapy by expressing the nucleotide sequence in the cell. For example, the antibody is used for chimeric antigen receptor T cell immunotherapy (CAR-T) and the like.

The pharmaceutical composition according to the present invention can be directly used for binding to a LAG-3 protein molecule, and thus can be used for preventing and treating diseases such as tumors. In addition, other therapeutic agents can also be used at the same time.

The pharmaceutical composition according to the present invention comprises a safe and effective amount (e.g. 0.001-99 wt %, preferably 0.01-90 wt %, preferably 0.1-80 wt %) of the monoclonal antibody according to the present invention and a pharmaceutically acceptable carrier or excipient. Such carriers include (but are not limited to): saline, buffers, glucose, water, glycerol, ethanol, and a combination thereof. Pharmaceutical preparations should correspond to the administration modes. The pharmaceutical composition according to the present invention can be prepared in the form of an injection, for example, by a conventional method using physiological saline or an aqueous solution containing glucose and other adjuvants. A pharmaceutical composition, for example, an injection and a solution, should be prepared under aseptic conditions. The administration amount of an active ingredient is a therapeutically effective amount, for example, about 1 µg per kilogram of body weight to about 5 mg per kilogram of body weight daily. In addition, the polypeptide according to the present invention may also be used in combination with an additional therapeutic agent.

When a pharmaceutical composition is used, a safe and effective amount of an immunoconjugate is administered to a mammal, wherein the safe and effective amount is generally at least about 10 µg per kilogram of body weight, and in most cases, no more than about 50 mg per kilogram of body weight, preferably, the amount is from about 10 µg per kilogram of body weight to about 20 mg per kilogram of body weight. Of course, a specific amount should also depend on the factors such as administration route and physical conditions of a patient, which fall into the skills of skilled physicians.

The main advantages of the invention are:

(1) the antibody of the present invention has a series of excellent features:

① the variable region sequence is different from those of existing antibodies (homology<92%);

② the epitope is different from that binded by BMS986016;

③ the antibody of the present invention has a strong affinity with LAG-3 (for example, KD value of 405B8H3 is 1.96 nM);

④ the antibody of the present invention has a good activity to stimulate T cell activation.

(2) Compared with antibodies obtained from phage library, the antibody of the present invention obtained by hybridoma technology has high affinity and good sequence expression.

(3) The present invention has obtained antibodies with different sequences, which can specifically bind to LAG-3 antibodies with a binding activity lower than nanomolar, and can block the binding of LAG-3 to its ligand MHCII/LSECtin. By reversing the inhibition on T cell activation activity by LAG-3, the antibody can activate T cells to secrete IL-2, with better activities.

(4) The antibody of the present invention has a stronger ability to bind to the monkey (such as Chinese monkey) LAG-3 protein on the cell surface than that of the control antibody. The antibody of the present invention has a cross-binding reaction with monkey antigens, and can be applied to in vivo experiments in primates, for preclinical toxicology studies and preclinical pharmacokinetic studies.

The invention is further illustrated below in conjunction with specific embodiments. It should be understood that the examples are not intended to limit the scope of the invention. The experimental methods without detailed conditions in the following examples are generally in accordance with the conditions described in the conventional conditions such as Sambrook. J et al. "Guide to Molecular Cloning Laboratory" (translated by Huang Peitang et al., Beijing: Science Press, 2002), or in accordance with the conditions recommended by the manufacturer (for example, product manuals). Unless otherwise stated, percentages and parts are calculated by weight. Unless otherwise specified, the experimental materials and reagents used in the following examples are commercially available.

General Methods

The present invention uses traditional hybridoma technology to prepare monoclonal antibodies. The traditional hybridoma preparation technology was established by Kohler and Milstein 40 years ago, and has now been widely used in the preparation and production of many related monoclonal antibodies in scientific research, diagnosis, and treatment. Although the basic method is still in use today, there have been changes, improvements and innovations in many aspects, including the use of different strains of animals such as genetically modified animals, the introduction of electrofusion technology, and the application of high-efficiency screening technology equipment such as ClonePix equipment, which make the application of hybridoma technology more diverse and efficient. Monoclonal antibodies prepared from conventional animals such as mice can be cloned by conventional molecular biology methods to clone the antibody heavy chain variable region and light chain variable region genes, and the variable region genes can be grafted to human antibody constant region genes to form human-mouse chimeric antibodies to greatly reduce the immunogenicity when used in human body. In addition, the CDR domains of the variable region of the mouse antibody can be grafted onto the framework of the human antibody, thereby reducing the composition of the mouse antibody to less than 5%, greatly increasing the safety of the antibody used in human body. Antibodies obtained through this approach are called humanized antibodies and are currently the main product in the antibody drug market. According to the latest advances in monoclonal antibody technology, the present invention adopts optimized hybridoma technology to prepare the required anti-LAG-3 antibody.

Example 1 Preparation of LAG-3 Specific Antibody

Preparation of immunogens including extracellular region LAG-3 protein, LAG-3 recombinant cell strain, and expression plasmid of LAG-3 DNA vector.

Immunogen 1), the amino acid sequence 23-450 of the extracellular region of human LAG-3 protein (as shown in SEQ ID No: 61 in the sequence listing) was cloned into the pCpC vector with human IgG Fc fragment (hFc) (purchased from Invitrogen, V044-50) and plasmids were prepared according to established standard molecular biology methods. For specific methods, see Sambrook, J., Fritsch, E. F., and Maniatis T. (1989). Molecular Cloning: A Laboratory Manual, Second Edition (Plainview, N.Y.: Cold Spring Harbor Laboratory Press). HEK293 cells (purchased from Invitrogen) were transiently transfected (PEI, Polysciences) and expanded using FreeStyle™ 293 (Invitrogen) at 37° C. After 4 days, the cell culture was collected, and the cell components were removed by centrifugation to obtain the culture supernatant containing the extracellular region of LAG-3 protein. The culture supernatant was loaded onto a protein A affinity chromatography column (Mabselect Sure, purchased from GE Healthcare), and an ultraviolet (UV) detector was used to monitor the change in ultraviolet absorbance (A280 nm). After the sample was loaded, the protein affinity chromatography column was washed with PBS phosphate buffer (pH 7.2) until the UV absorption value returned to the baseline, and then eluted with 0.1M glycine hydrochloric acid (pH 2.5). The LAG-3 protein with hFc tag (LAG-3-hFc) eluted from the protein A affinity chromatography column was collected and dialyzed overnight with PBS phosphate buffer (pH 7.2) in a refrigerator at 4° C. The dialyzed protein was sterile filtered by a 0.22 micron filter and stored at −80° C. after subpackage to obtain purified immunogen human LAG-3-hFc protein. The immunogen LAG-3-hFc protein needed a series of quality control tests before use, such as tests of protein concentration, purity, molecular weight and biological activity.

Wherein, the binding activity of immunogen LAG-3-hFc to MHC II was tested by FACS, specifically:

Raji cells expressing MHC II were expanded in a T-175 cell culture flask to a 75-90% confluence, centrifuged to discard the culture medium, washed 1-2 times with PBS buffer, and after counted, the cells were diluted with blocking solution (PBS, 2% fetal bovine serum) to $1-2 \times 10^6$ cells per ml, incubated on ice for 20-30 minutes, and then washed twice with blocking solution (PBS, 2% fetal bovine serum). The collected cells were suspended in blocking solution (PBS, 2% fetal bovine serum) to $2 \times 10^6$ cells/ml, added as 100 μl per well to a 96-well FACS reaction plate ($2 \times 10^5$ cells per well), and centrifuged to discard the culture medium, and the LAG-3 protein with hFc label was diluted in a gradient, then added as 100 microliters per well to Raji cells, and incubated on ice for 1-2 hours. The plate was washed twice with blocking solution (PBS, 2% fetal bovine serum) by centrifugation, added with 100 microliters of fluorescent (Alexa 488)-labeled secondary antibodies per well, and incubated on ice for 0.5-1.0 hours. The plate was washed 2-3 times by centrifugation with blocking solution (PBS, 2% fetal bovine serum), added with 100 microliters of PBS per well to suspend cells, and detected using FACS (FACSVerse, BD) and the results were analyzed.

Wherein, the binding activity of immunogen LAG-3-hFc and LSECtin was detected by ELISA, specifically including the following steps.

The hFc-labeled LAG-3 protein (LAG-3-hFc, i.e. the immunogen) was diluted with PBS to 1 μg/mL, and added as 100 μl/well to an ELISA microplate, and incubated overnight at 4° C. After blocked with ELISA blocking solution (containing 1% BSA, pH 7.4 PBS phosphate buffer solution, wherein the percentage is the mass percentage) at 37° C. for two hours, the plated was added with gradient dilution of LSECtin-His tags, and incubated at 37° C. for 1 hour. The LSECtin-His was purchased from R&D system, product number 2947-CL. The plate was added with anti-His tag horseradish peroxidase (purchased from GenScript, trade number A00612), incubated at room temperature for 30 minutes and added with 100 microliters/well of TMB color developing solution. After incubated at room temperature for 15 minutes, the plate was added with 50 microliters of 1N hydrochloric acid to stop the color reaction, and read with an ELISA plate reader for the OD450 nm reading. The plate needed to be washed after each step.

Figure 2:
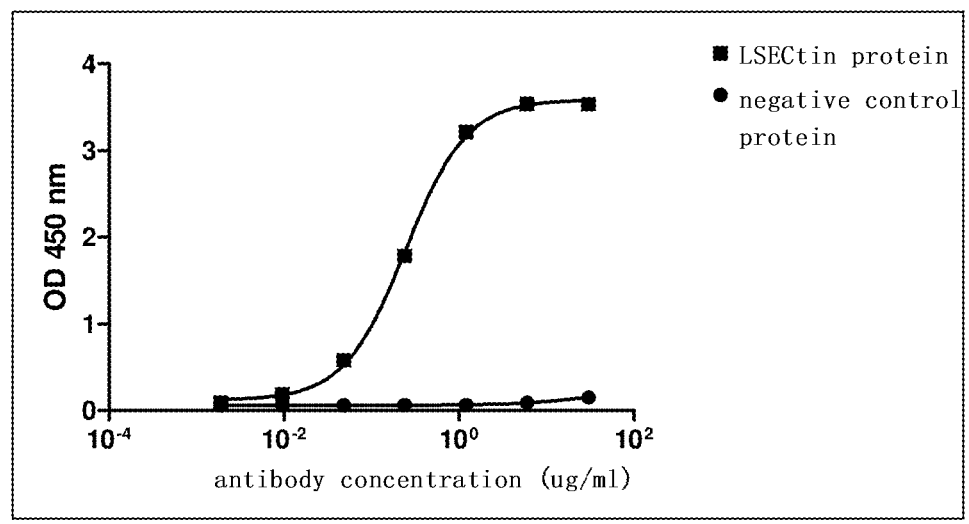
FIG. 2 shows the binding activity of LAG-3-hFc protein and its ligand LSECtin.

The results are shown in FIG. 1, FIG. 2 and Table 1, Table 2.

TABLE 1

The binding activity of LAG-3-hFc protein with its ligand MHCII

| Protein concentration (ug/ml) | hLAG-3-hFc Mean fluorescence value | hFc Mean fluorescence value |
|---|---|---|
| 200 | 324 | 21 |
| 66.7 | 426 | 28 |
| 22.2 | 356 | 20 |
| 7.4 | 249 | 18 |
| 2.5 | 121 | 14 |
| 0.8 | 73 | 12 |

TABLE 1-continued

The binding activity of LAG-3-hFc protein with its ligand MHCII

| Protein concentration (ug/ml) | hLAG-3-hFc Mean fluorescence value | hFc Mean fluorescence value |
|---|---|---|
| 0.3 | 39 | 11 |
| 0.1 | 29 | 13 |
| 0.0 | 22 | 10 |
| 0.0 | 19 | 10 |
| 0.0 | 16 | 12 |
| 0 | 13 | 13 |

TABLE 2

The binding activity of LAG-3-hFc protein with its ligand LSECtin

| Coating antigen | Protein concentration (ug/mL) | Negative protein | | LSECtin Protein | |
|---|---|---|---|---|---|
| hlag3-hFC 1 ug/ml | 30.0000 | 0.16 | 0.14 | 3.54 | 3.53 |
| | 6.0000 | 0.09 | 0.09 | 3.53 | 3.55 |
| | 1.2000 | 0.07 | 0.06 | 3.25 | 3.18 |
| | 0.2400 | 0.07 | 0.06 | 1.77 | 1.80 |
| | 0.0480 | 0.06 | 0.06 | 0.62 | 0.54 |
| | 0.0096 | 0.06 | 0.06 | 0.19 | 0.18 |
| | 0.0019 | 0.06 | 0.06 | 0.09 | 0.09 |
| | 0.0000 | 0.06 | 0.06 | 0.07 | 0.06 |

The results show that the binding activity of LAG-3 and MHCII at the cellular level varied with the concentration of LAG-3-hFC, and the binding activity of LAG-3 and LSECtin at the protein level varied with the concentration of LAG-3-hFC. The control protein was a non LAG-3 fusion protein. The expressed ligand and receptor proteins had the correct conformations, which were suitable for immunization, establishment of receptor-ligand binding blocking detection methods and identification of antibody activity.

6-8 weeks old BabL/C and SJL mice (provided by Shanghai Slack Animal Center Breeding) were used for LAG-3 protein immunization, and the mice were raised under SPF conditions after received. In the first immunization, LAG-3 protein was emulsified with Freund's complete adjuvant and injected intraperitoneally with 0.25 ml, 50 micrograms of protein per mouse. In the booster immunization, LAG-3 protein was emulsified with Freund's incomplete adjuvant and injected intraperitoneally with 0.25 ml, 50 micrograms of protein per mouse. The interval between the first immunization and the first booster immunization was 2 weeks. After that, the intervals between each subsequent immunization were 3 weeks. Blood was collected 7 days after each booster immunization, and the antibody titer and specificity in the serum were detected by ELISA and FACS.

Figure 3:
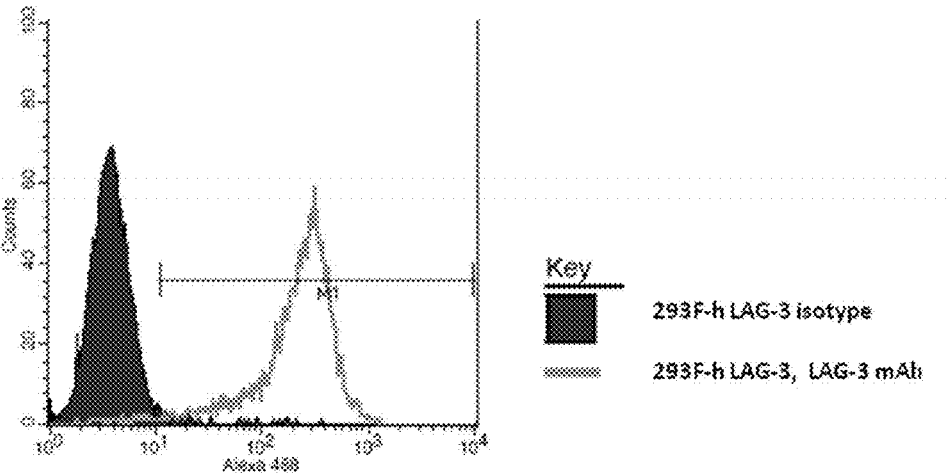
FIG. 3 shows the FACS detection results of HEK293 cells transfected with LAG-3 gene.

Immunogen 2), the human LAG-3 full-length amino acid sequence was cloned into pIRES vector (purchased from Clontech) and the plasmid was prepared. After plasmid transfection on HEK293 cell line and CHOK1 cell line (both purchased from Invitrogen) (transfected with X-treme GENE HP DNA Transfection Reagent, which is purchased from Roche, Cat #06 366 236 001, and operated according to the instructions), cells were selectively cultured in DMEM medium containing 10% (w/w) FBS and containing 0.5 µg/ml puromycin for 2 weeks. Subcloning was conducted in a 96-well culture plate by a limiting dilution method, and the plate was placed at 37° C., 5% (v/v) $CO_2$. After about 2 weeks, some of the monoclonal wells were selected and amplified into 6-well plates. The amplified clones were stained with known LAG-3 antibodies and screened by flow cytometry. The culture expanding of the monoclonal cell line with better growth and higher fluorescence intensity was continued and cryopreserved in liquid nitrogen, to obtain the immunogen LAG-3 recombinant cell line. The specific selection results are shown in Table 3 and FIG. 3. In Table 3, positive cells (%) refer to the percentage of number of positive cells in the total number of cells, and MFI is the average fluorescence intensity value of the measured cell population.

TABLE 3

The FACS screening detection results of HEK293 cells transfected with LAG-3 gene

| | | IgG control | | Anti-LAG-3 mAb | |
|---|---|---|---|---|---|
| No. | Recombinant cell clone ID | Gated (%) | MFI | Gated (%) | MFI |
| 1 | 5C5 | 0.46 | 3.5 | 98.93 | 151.91 |
| 2 | 5E7 | 0.99 | 3.6 | 98.48 | 193.95 |
| 3 | 5F10 | 0.28 | 3.02 | 98.87 | 170.35 |
| 4 | 5G8 | 0.22 | 2.87 | 98.68 | 191.76 |

The results show that HEK293 cells have a higher level of LAG-3 expression, which is suitable for use as an immunogen and for identification of antibody binding activity.

6-8 weeks old BabL/C and SJL mice (provided by Shanghai Slack Animal Center Breeding) were used for LAG-3 cell immunization, and the mice were raised under SPF conditions after received. The HEK293 stable cell line transfected with human LAG-3 was expanded to a 75-90% confluence in a T-75 cell culture flask. The medium was aspirated, and the cells were washed 1-2 times with DMEM basal medium, and then treated with enzyme-free cell dissociation fluid and cells were collected. Cells were washed 1-2 times with DMEM basal medium. After cell counting, the cells were diluted with PBS to $1-2\times10^7$ cells per ml. Each mouse was intraperitoneally injected with 0.5 ml of cell suspension during each immunization. The interval between the first and the second immunization was 2 weeks. After that, the intervals between each subsequent immunization were 3 weeks. Blood was collected 7 days after each booster immunization, and the antibody titer and specificity in the serum were detected by FACS.

Immunogen 3), LAG-3 full-length amino acid sequence cDNA was cloned into a pCDNA3.1 vector and coated on a 1.0 um gold colloidal bullet, and immunized with Helios gene gun (Bio-rad). The detailed method was developed according to the instructions of Helios gene gun.

Figure 4:
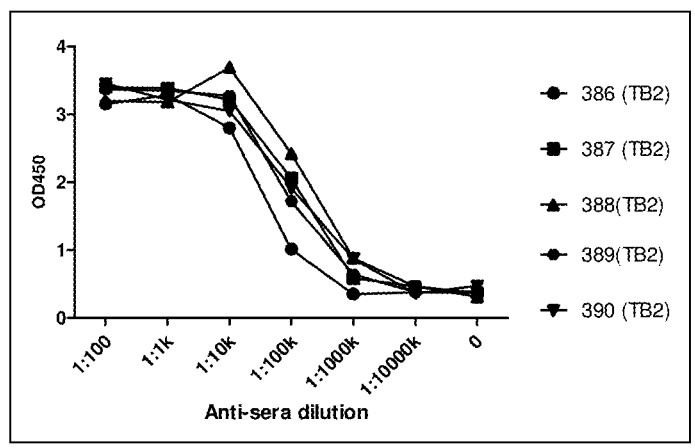
FIG. 4 shows the ELISA detection of the serum antibody titer of mice immunized with LAG-3-hFC protein.
Figure 5A:
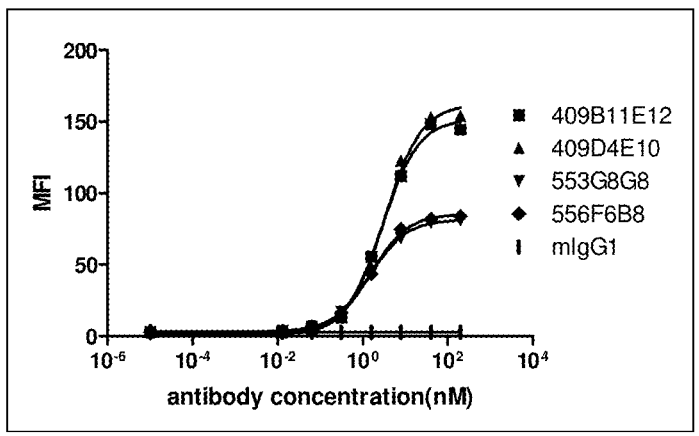
FIG. 5a shows the FACS detection of the binding reaction of LAG-3 antibody and HEK293-hLAG-3.
Figure 5B:
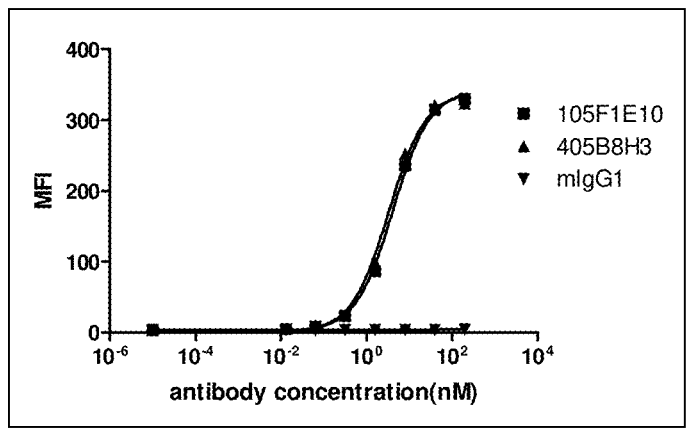
FIG. 5b shows the FACS detection of the binding reaction of LAG-3 antibody and HEK293-hLAG-3.
Figure 6A:
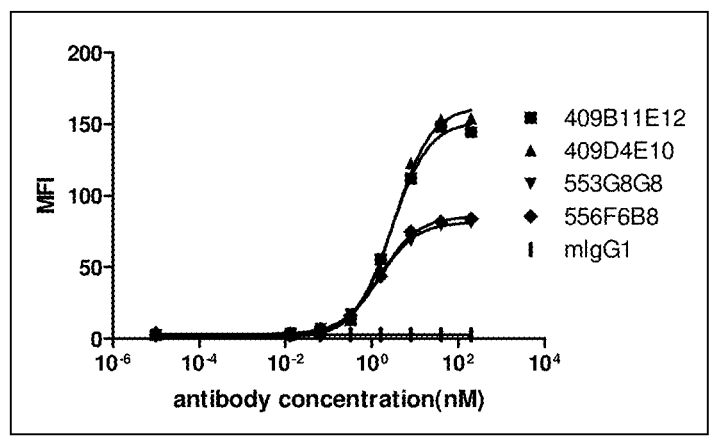
FIG. 6a shows the FACS detection of the binding reaction of LAG-3 antibody and HEK293-cLAG-3.
Figure 6B:
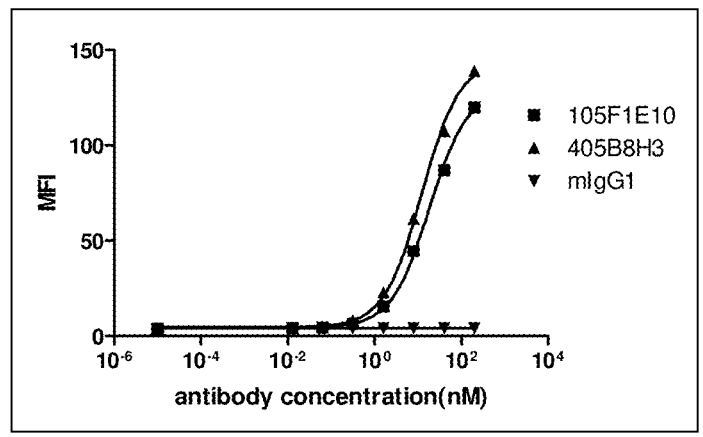
FIG. 6b shows the FACS detection of the binding reaction of LAG-3 antibody and HEK293-cLAG-3.

6-8 weeks old BabL/C and SJL mice (provided by Shanghai Slack Animal Center Breeding) were received and raised under SPF conditions. All mice were immunized with the gene gun through the abdomen for 3-4 times, 3-4 shots each time, 1.0 µg cDNA amount per shot. The interval between the first immunization and the first booster immunization was 2 weeks. After that, the intervals between each subsequent immunization were 3 weeks. Blood was collected 7 days after each booster immunization, and the antibody titer in the serum was detected by ELISA. Usually, the ELISA titer of most mice can reach more than 1:1000 after 2-3 times of immunization. Table 4 and FIG. 4 show the results of the antibody titer in serum detected by ELISA after LAG-3-hFC protein immunization.

TABLE 4

Detection of serum antibody titer in mice after
LAG-3-hFC protein immunization by ELISA

| $OD_{450nm}$ batch | Serum dilution | | | | | | Blank control |
|---|---|---|---|---|---|---|---|
| | 1:100 | 1:10³ | 1:10⁴ | 1:10⁵ | 1:10⁶ | 1:10⁷ | |
| 386 TB2 | 3.15 | 3.28 | 2.80 | 1.01 | 0.35 | 0.38 | 0.39 |
| 387 TB2 | 3.40 | 3.38 | 3.22 | 2.06 | 0.58 | 0.46 | 0.37 |
| 388 TB2 | 3.20 | 3.18 | 3.69 | 2.42 | 0.88 | 0.46 | 0.31 |
| 389 TB2 | 3.37 | 3.35 | 3.27 | 1.72 | 0.64 | 0.38 | 0.37 |
| 390 TB2 | 3.45 | 3.22 | 3.05 | 1.91 | 0.87 | 0.36 | 0.47 |

The results showed that: after 3 times of immunization with the immunogen, most mice had an ELISA titer of more than 1:100,000, indicating that mice had a better humoral immune response to the immunogen, and their spleen cells can be used for Hybridoma cell preparation.

Mice whose titers meet the requirements can be selected for cell fusion and hybridoma preparation. Before cell fusion, each mouse was injected intraperitoneally with 50-100 micrograms of purified LAG-3-hFc, for the last immunization. After 3-5 days, the mice were sacrificed and splenocytes were collected. Cells were washed by centrifugation at 1000 revolutions per minute in DMEM basal medium 3 times, and then mixed with mouse myeloma cells SP2/0 (purchased from ATCC) at a ratio of 5:1 according to the number of viable cells. High-efficiency electrofusion or PEG method (see METHODS IN ENZYMOLOGY, VOL. 220) was used for cell fusion. The fused cells were diluted into DMEM medium containing 20% fetal bovine serum and 1×HAT, wherein the percentage was the mass percentage. Then the cell solution was added as 1×10⁵/200 microliters per well to a 96-well cell culture plate, and put in a 5% $CO_2$, 37° C. incubator, wherein the percentage was the volume percentage. After 14 days, ELISA and Acumen (microwell plate cell detection method) were used to screen the supernatant in cell fusion plate. The positive clones with $OD_{450\ nm}$>1.0 in ELISA and MFI value>100 in Acumen were expanded to a 24-well plate, and cultured in a DMEM medium (Invitrogen) containing 10% (w/w) of fetal bovine serum, at 37° C. and 5% (v/v) $CO_2$. After 3 days of culture, the culture solution expanded in the 24-well plate was centrifuged. The supernatant was collected, and the supernatant was analyzed for antibody subtypes. ELISA and FACS were used to determine the binding activity to LAG-3 protein and LAG-3 positive cells, and the ligand receptor binding experiment was used to determine the blocking activity of the antibody sample to the LAG-3 receptor.

According to the results of the 24-well plate screening, hybridoma cells with $OD_{450\ nm}$>1.0 in the ELISA experiment, MFI value>50 in the FACS experiment, and the blocking inhibition rate of the LAG-3 receptor by the hybridoma cell culture supernatant in the ligand receptor binding experiment reaching 60% were selected as qualified positive clones. The qualified hybridoma cells were selected to subclone in a 96-well plate by limiting dilution method, and cultured in a DMEM medium (purchased from Invitrogen) containing 10% (w/w) FBS, at 37° C., 5% (v/v) $CO_2$. 10 days after subcloning, ELISA and Acumen were used for preliminary screening, and positive monoclones were selected and amplified to a 24-well plate to continue culture. After 3 days, FACS was used to determine the positive antigen binding and the LAG-3 receptor ligand binding experiment was used to evaluate the biological activity (the evaluation criteria were $OD_{450\ nm}$>1.0 in the ELISA experiment, MFI value>50 in the FACS experiment, and the blocking inhibition rate of the hybridoma cell culture supernatant on MHCII ligand reached 60% in the ligand receptor binding experiment).

According to the test results of the 24-well plate samples, the positive clones were expanded in DMEM (purchased from Invitrogen) medium containing 10% (w/w) FBS at 37° C. and 5% (v/v) $CO_2$. The cells were suspended in freezing solution [DMEM containing 20% (w/w) FBS and 10% (w/w) DMSO], and cryopreserved in liquid nitrogen according to conventional methods, to obtain hybridoma cells of the present invention, which can be used for subsequent antibody production, purification and amino acid sequence determination.

Example 2 Identification of Purified Antibodies (I) Detection of the Binding of Antibodies to LAG-3 Expressing Cells by Flow Cytometry (FACS)

The pIRES plasmid containing the full-length nucleotide sequence encoding human LAG-3 described in the preparation of Immunogen 2 in Example 1 was transfected into a 293F cell line to obtain a stable 293F cell line containing human LAG-3 (herein referred to as HEK293-hLAG-3 stable cell line). The pIRES plasmid with the monkey-derived full-length gene was transfected into the HEK293 cell line to construct a HEK293 stable cell line containing monkey LAG-3 (herein referred to as HEK293-cLAG-3 stable cell line). The HEK293-hLAG-3 stable cell line and HEK293-cLAG-3 stable cell line were expanded in a T-75 cell culture flask to a 90% confluence. The medium was aspirated, and the cells were washed with HBSS (Hanks' Balanced Salt Solution) 1-2 times, then treated with a enzyme-free cell dissociation fluid (Versene solution: Life technology) and the cells were collected. The cells were washed with HBSS buffer for 1-2 times. After counted, the cells were diluted with HBSS to 1-2×10⁶ cells per ml, added with 1% goat serum blocking solution, incubated on ice for 20-30 minutes, and then washed with HBSS for 2 times by centrifugation. The collected cells were suspended in the FACS buffer (HBSS+1% BSA) to 2×10⁶ cells/ml, added as 100 microliters per well to a 96-well FACS reaction plate, added with 100 microliters per well of the antibody sample to be tested, incubated on ice for 1-2 hours. The plate was washed twice with the FACS buffer by centrifugation, added with 100 microliters of fluorescent (Alexa 488)-labeled secondary antibodies per well, and incubated on ice for 0.5-1.0 hours. The plate was washed 2-3 times with FACS buffer by centrifugation, added with 100 µl fixative solution (4% Paraformaldehyde) per well to suspend the cells. 5-10 minutes later, it was washed 1-2 times with FACS buffer by centrifugation. The cells were suspended with 100 microliters of FACS buffer, FACS (FACSCalibur, BD) was used for detection and the results were analyzed. The results are shown in Table 5 and Table 6, FIG. 5a, FIG. 5b and FIG. 6a, FIG. 6b. The antibody to be tested can bind to human or monkey LAG-3 proteins on the cell surface. The activity of each antibody was equivalent, indicating that binding abilities of the antibodies to LAG-3 were strong. Wherein, the IgG control was murine IgG, and the data in the table is the average fluorescence intensity values of the cell populations measured by MFI.

TABLE 5

FACS detection of the binding reaction of LAG-3 antibody and HEK293-hLAG-3

Mean fluorescence intensity
Antibody concentration (nM)

| Clone ID | 200.000 | 40.000 | 8.000 | 1.600 | 0.320 | 0.064 | 0.013 | 0.000 |
|---|---|---|---|---|---|---|---|---|
| 409B11E12 | 144.4 | 148.4 | 112.1 | 55.6 | 13.4 | 5.0 | 2.9 | 2.5 |
| 409D4E10 | 154.3 | 153.0 | 122.8 | 48.0 | 13.0 | 4.9 | 3.3 | 2.8 |
| 553G8G8 | 81.0 | 79.4 | 68.4 | 44.4 | 17.1 | 7.0 | 3.9 | 2.7 |
| 556F6B8 | 83.7 | 81.8 | 74.9 | 43.5 | 16.1 | 6.8 | 3.6 | 2.8 |
| mIgG1 | 2.8 | 2.8 | 2.9 | 2.7 | 2.7 | 2.9 | 2.9 | 3.0 |
| 105F1E10 | 330.0 | 314.7 | 235.4 | 86.2 | 23.3 | 8.6 | 5.0 | 3.7 |
| 405B8H3 | 323.7 | 320.9 | 252.4 | 99.4 | 24.7 | 8.7 | 5.0 | 3.7 |
| mIgG1 | 4.2 | 4.0 | 3.9 | 3.9 | 3.8 | 3.8 | 3.8 | 3.8 |

TABLE 6

FACS detection of the binding reaction of LAG-3 antibody and HEK293-cLAG-3

Mean fluorescence intensity
Antibody concentration (nM)

| Clone ID | 200.000 | 40.000 | 8.000 | 1.600 | 0.320 | 0.064 | 0.013 | 0.000 |
|---|---|---|---|---|---|---|---|---|
| 409B11E12 | 133.6 | 102.1 | 69.9 | 24.4 | 8.0 | 4.2 | 3.3 | 3.0 |
| 409D4E10 | 153.3 | 129.6 | 93.8 | 36.1 | 11.5 | 4.7 | 3.5 | 3.0 |
| 553G8G8 | 127.9 | 111.9 | 77.7 | 28.1 | 8.8 | 4.2 | 3.5 | 3.2 |
| 556F6B8 | 52.2 | 51.0 | 46.7 | 24.2 | 9.8 | 5.1 | 3.9 | 3.4 |
| mIgG1 | 3.6 | 3.3 | 3.3 | 3.2 | 3.3 | 3.2 | 3.5 | 3.4 |
| 105F1E10 | 119.9 | 87.0 | 44.6 | 15.4 | 6.6 | 4.5 | 4.1 | 3.9 |
| 405B8H3 | 138.9 | 107.5 | 61.4 | 23.0 | 8.0 | 4.9 | 4.2 | 3.9 |
| mIgG1 | 4.2 | 4.1 | 4.1 | 4.0 | 4.0 | 4.0 | 4.0 | 4.0 |

Figure 7A:
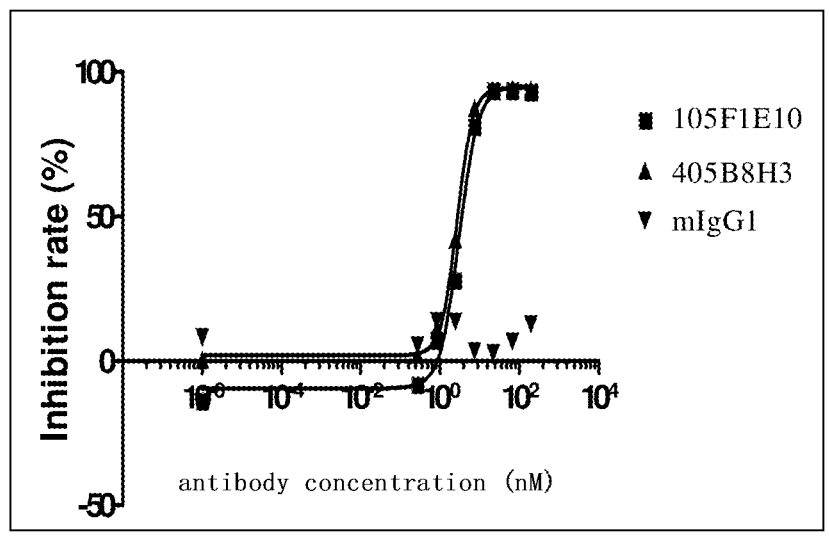
FIG. 7a shows the inhibition of the LAG-3 antibodies on the binding of LAG-3 protein to its receptor MHC II.
Figure 7B:
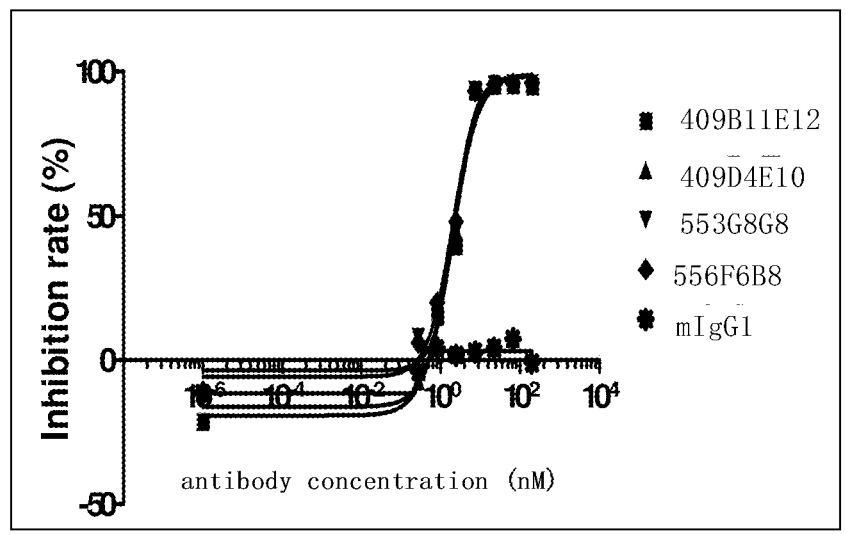
FIG. 7b shows the inhibition of the LAG-3 antibodies on the binding of LAG-3 protein to its receptor MHC II.

(II) Detection of the LAG-3 antibody blocking of the binding of LAG-3 to its ligand MHC II by LAG-3 receptor ligand binding assay Raji cells expressing MHC II were expanded in a T-175 cell culture flask to a 75-90% confluence, centrifuged to discard the culture medium, washed 1-2 times with PBS buffer, and after counted, the cells were diluted with blocking solution (PBS, 2% fetal bovine serum) to $1-2\times10^6$ cells per ml, added as 100 μl per well to the 96-well FACS reaction plate ($1\times10^5$ cells per well), incubated on ice for 20-30 minutes. The antibody sample to be tested was mixed with 1 ug/ml LAG-3-hFc protein in equal volume and incubated at room temperature for 30 minutes. The FACS reaction plate incubating the Raji cells was centrifuged to discard the supernatant. The above mixture was added as 100 μl per well to Raji cells and incubated on ice for 1-2 hours. The plate was washed twice with blocking solution (PBS, 2% fetal bovine serum) by centrifugation, added with 100 microliters of fluorescent (Alexa 488)-labeled secondary antibodies per well, and incubated on ice for 1.0 hours. The plate was washed 2-3 times by centrifugation with blocking solution (PBS, 2% fetal bovine serum), added with 100 microliters of PBS per well to suspend cells, and detected using FACS (FACS Calibur, BD) and the results were analyzed. The results are shown in Table 7 and FIGS. 7a and 7b. Wherein, the IgG control was murine IgG, and the data in the table is the inhibition rate (%).

TABLE 7

Inhibitions of the LAG-3 antibodies on the binding of LAG-3 protein to its receptor MHC II

| Inhibition rate (%) Clone number | Antibody concentration (nM) | | | | | | | |
|---|---|---|---|---|---|---|---|---|
| | 200.000 | 66.667 | 22.222 | 7.407 | 2.469 | 0.823 | 0.274 | 0.000 |
| 105F1E10 | 93.1 | 93.6 | 93.6 | 81.0 | 27.8 | 7.0 | −8.3 | −14.0 |
| 405B8H3 | 93.9 | 94.0 | 93.6 | 87.3 | 41.9 | 10.9 | 2.1 | 0.3 |
| mIgG1 | 12.8 | 6.7 | 2.8 | 3.4 | 13.7 | 13.8 | 5.3 | 8.2 |
| 409B11E12 | 95.0 | 95.5 | 95.3 | 93.4 | 39.6 | 15.3 | −3.9 | −21.2 |
| 409D4E10 | 95.9 | 96.0 | 95.8 | 93.0 | 44.7 | 18.2 | −7.5 | −21.4 |
| 553G8G8 | 95.9 | 96.0 | 95.8 | 93.8 | 45.0 | 15.2 | 8.1 | −12.4 |
| 556F6B8 | 96.0 | 95.9 | 95.6 | 93.3 | 48.1 | 20.1 | 6.0 | −10.7 |
| mIgG1 | −0.9 | 7.4 | 4.2 | 2.8 | 1.8 | 4.0 | −3.9 | −11.5 |

The results show that the obtained antibodies can inhibit the binding of LAG-3 protein and its ligand MHCII to varying degrees, and the activities of the tested antibodies were comparable.

(III) Detection of the Effect of LAG-3 Antibody on Lymphocyte Activity by Antigen-Specific T Lymphocyte Stimulation Test In the antigen-specific T lymphocyte stimulation test, LAG-3 antibodies block the binding of LAG-3 and MHC II to relieve the inhibition of T lymphocyte activity, thereby stimulating the proliferation of T cells.

1. To obtain antigen-specific T lymphocytes, firstly, the mouse CD4 isolation kit was used, CD4+ T cells were negatively screened from lymphocyte samples from OVA transgenic mice using immunomagnetic bead technology and combined antibodies, and antigen-specific CD4+T lymphocytes were isolated. The obtained T cells were mixed with the mouse thymoma cell line BW5147.G.1.4 at a ratio of 5:1, and the polyethylene glycol (PEG) cell fusion method was used for cell fusion. The fused cells were selectively cultured with 1×HAT medium containing hypoxanthine, aminopteridine and thymidine, and the obtained monoclones were expanded in a 24-well plate for expansion and culture, and the single clones were screened after 2-3 days. The clones were screened by in vitro antigen presentation experiment. Spleen cells from the same strain of common C57BL/6 mice were mixed with specific antigen OVA323-339 and the mixture was added to the culture medium of monoclonal cells. The monoclonal cells were incubated overnight to collect the supernatant (For specific methods, see David H et al., Methods Mol Biol, 2013, 960: 297-307). Enzyme-linked immunosorbent assay was used to detect the content of mouse IL2 (mIL2) in the supernatant. And the best monoclonal cells with good cell growth, stable passage (at least a dozen generations), and high secretion of mIL-2 were selected for expanding cultivation and cryopreservation in liquid nitrogen. Finally, T lymphocyte hybridoma (8B2) was selected as the best clone.

To construct a stable cell line overexpressing immunosuppressive factors, the full-length gene sequence of human LAG-3 was cloned into the pIRES expression vector and packaged into a lentivirus (Shanghai Jima). The T lymphocyte hybridoma cell line 8B2 was infected with lentivirus. The transfected cells were selectively cultured in antibiotic-containing medium. After 2 weeks, they were subcloned in a 96-well culture plate by limiting dilution. After the clones grew up, the monoclonal well cells were expanded into 6-well plates or culture flasks. The amplified clones were screened with anti-LAG-3 specific antibodies by flow cytometry. The culture expanding of the monoclonal cell line with better growth and higher fluorescence intensity was continued and cryopreserved in liquid nitrogen. Finally, T lymphocyte hybridoma (8B2)_hLAG-3(3E4) was selected as the best clone.

2. In the antigen-specific T lymphocyte stimulation experiment, T lymphocyte hybridoma (8B2)_hLAG-3(3E4) was cultured in a T-175 cell culture flask to a 75-90% confluence. The medium was discarded, and cells was washed with PBS for 1-2 times. After counted, the cells were spread as 1-2E5 cells in 50 microliters per well on a 96-well cell culture plate, then added with dilution medium for the test antibody with twice of the final concentration to the culture plate and incubated at room temperature for 30 minutes. At the same time, the spleen cells from the common C57BL/6 mice of the same strain and the specific antigen OVA323-339 were mixed and incubated for 30 minutes at room temperature. Finally, 50 μl of the mixture was added to each well of the culture plate to ensure that each reaction well had a volume of 200 ul. The supernatant were collected after incubated in a 37° C. 5% CO$_2$ incubator overnight, and frozen below −20 for testing.

3. The cytokine interleukin IL-2 enzyme-linked immunosorbent assay in the cell supernatant In the cytokine interleukin IL-2 enzyme-linked immunosorbent assay in the cell supernatant, the R&D system related detection kit Mouse IL-2 DuoSet ELISA (DY402) was used, and operated in accordance with the instructions. All test reagents except the tested antibodies were provided by the test kit.

The enzyme-linked immunosorbent assay to determine the cytokine interleukin IL-2 content in the cell supernatant used a double antibody sandwich ELISA kit (purchased from R&D Systems, IL-2 Cat #DY402). The experimental operation was strictly in accordance with the requirements of the kit instructions, and all test reagents were provided by the kit. The specific experiment was briefly described as follows. The IL-2 polyclonal antibody was coated on the ELISA microwell plate, sealed with plastic film and incubated overnight at 4° C. The plate was washed 4 times with the plate washing solution on the next day, and added with the blocking solution and blocked at room temperature for 1-2 hours. The plate was washed 4 times with the plate washing solution. The cell supernatant obtained in step 2 was used as the test sample. The standard and the test sample were incubated at room temperature for 2 hours. 400 microliters of washing solution was added to each well, the plate washing was repeated 4 times. Then horseradish peroxidase-labeled antibody against human IL-2 was added, and incubated for 2 hours at room temperature to form an immune complex with IL-2 on the microplate and the microwells were washed. The substrate was added for color development, protected from light at room temperature for 30 minutes. Finally the stop solution was added, and the absorbance at A450 nm was measured with a microplate reader.

Figure 8A:
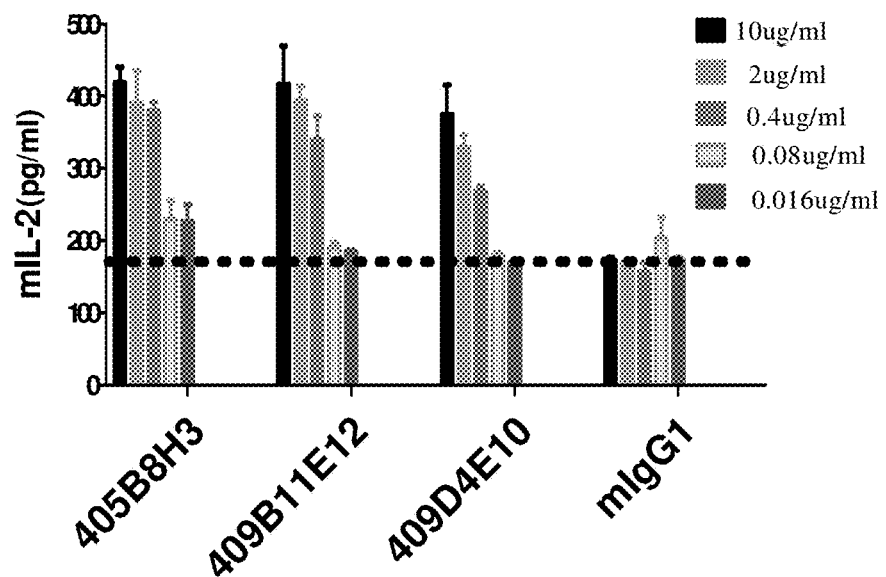
FIG. 8a shows the effect of LAG-3 antibodies on IL-2 secretion in the antigen-specific T lymphocyte stimulation test.

The effects of LAG-3 antibodies on IL-2 secretion in the antigen-specific T lymphocyte stimulation experiment described in step 2 were detected. The results are shown in FIG. 8a, FIG. 8b, and Table 8, wherein the mIgG control was mouse IgG, and the data in the table is the IL-2 value (pg/mL).

TABLE 8

Effect of LAG-3 antibodies on IL-2 secretion in the antigen-specific T lymphocyte stimulation test

| | mIL-2 (pg/mL) | | | | |
| | Antibody concentration (ug/mL) | | | | |
| Clone ID | 10 | 2 | 4 | 0.08 | 0.016 |
| --- | --- | --- | --- | --- | --- |
| 405B8H3 | 440.6 | 434.6 | 392.0 | 203.6 | 204.7 |
| 409B11E12 | 363.7 | 375.7 | 373.7 | 182.9 | 187.2 |
| 409D4E10 | 335.0 | 346.5 | 260.7 | 174.6 | 171.5 |
| mIgG1 | 168.6 | 174.3 | 144.6 | 174.8 | 177.4 |
| 553G8G8 | 351.9 | 250.9 | 226.7 | 133.5 | 98.2 |
| 556F6B8 | 255.2 | 270.5 | 213.8 | 140.9 | 88.3 |
| mIgG1 | 108.2 | 84.1 | 84.2 | 89.2 | 104.5 |

The results show that the antibodies to be tested in the antigen-specific T lymphocyte stimulation test can enhance the IL-2 secretion of T lymphocytes, and the activation effects were concentration gradient dependent, and the activity rate of 405B8H3 was better than those of other antibodies.

(IV) Antigenic Epitope Prediction

The extracellular region of the human LAG-3 protein contains an exposed outer loop (eatra loop) with the following amino acid sequence: GPPAAAPGHPLAPGPHPAAPSSWGPRPRRY (positions 70-99 of SEQ ID NO: 61). In order to test the binding of purified antibodies to this region and predict the epitope bound by each antibody, peptide scanning experiments were performed throughout this region.

Fifteen overlapping peptides including the full length of the outer loop sequence were prepared and biotin was coupled to each C-terminus. Enzyme-linked immunosorbent assay (ELISA) was used to detect the binding of antibodies to these peptides. Streptavidin (sigma, Cat #M5432) was diluted with PBS to a final concentration of 1.0 μg/ml, and then added as 100 μl per well to a 96-well ELISA plate. The plate was sealed with plastic film and incubated overnight at 4° C. The plate was washed 2 times with the plate washing solution (PBS+0.01% Tween20) on the next day, and added with the blocking solution (PBS+0.01% Tween20+1% BSA) and blocked at room temperature for 1-2 hours. The blocking solution was poured off, and biotinylated peptides was added to a final concentration of 1 ug/ml, as 100 ul per well to the 96-well ELISA plate, incubated at 37° C. for 1-2 hours, then washed with plate washing solution (PBS+0.01% Tween20)2-3 times. Then the antibody samples to be tested were incubated as 100 μl per well at 37° C. for 1-2 hours, and then the plate was washed 2-3 times with a plate washing solution (PBS+0.01% Tween20). HRP (horseradish peroxidase) labeled secondary antibody was added, and the plate was incubated at 37° C. for 1-2 hours, and washed 2-3 times with a plate washing solution (PBS+0.01% Tween20). 100 μl of TMB substrate was added to each well. After incubated at room temperature for 15-30 minutes, the plate was added with 100 μl of stop solution (1.0N HCl) to each well. An ELISA plate reader (TiterMax 384plus, Molecular Device) was used to read the A450 nm value. The results of the peptide scanning experiment are summarized in Table 9 below.

TABLE 9

Results of peptide scanning experiment

| SEQ ID NO: | LAG-3 Extra cyclic peptide | 405B8H3 | 409B11E12 | 105F1E10 | 409D4E10 | BMS986016 |
|---|---|---|---|---|---|---|
| 96 | LAPGPHPAAPSSK-Biotin | - | - | - | - | - |
| 97 | APGPHPAAPSSWK-Biotin | - | - | - | - | - |
| 98 | PGPHPAAPSSWGK-Biotin | - | - | - | - | + |
| 99 | GPHPAAPSSWGPK-Biotin | - | - | - | - | ++ |
| 100 | PHPAAPSSWGPRK-Biotin | - | - | ++ | - | ++ |
| 101 | HPAAPSSWGPRPK-Biotin | - | - | ++ | - | ++ |
| 102 | PAAPSSWGPRPRK-Biotin | ++ | ++ | ++ | ++ | ++ |
| 103 | AAPSSWGPRPRRK-Biotin | ++ | ++ | ++ | ++ | ++ |
| 104 | APSSWGPRPRRYK-Biotin | ++ | ++ | ++ | ++ | - |
| 105 | PSSWGPRPRRYTK-Biotin | ++ | ++ | ++ | ++ | - |
| 106 | SSWGPRPRRYTVK-Biotin | ++ | ++ | ++ | ++ | - |
| 107 | SWGPRPRRYTVLK-Biotin | ++ | ++ | ++ | ++ | - |
| 108 | WGPRPRRYTVLSK-Biotin | + | ++ | + | ++ | - |
| 109 | GPRPRRYTVLSVK-Biotin | - | - | - | - | - |
| 110 | GPPAAAPGHPLAPGPHPAAPSSWGPRPRRYK-biotin | ++ | ++ | ++ | ++ | ++ |

| SEQ ID NO: | LAG-3 Extra cyclic peptide | 553G8G8 | 556F6B8 |
|---|---|---|---|
| 96 | LAPGPHPAAPSSK-biotin | - | - |
| 98 | PGPHPAAPSSWGK-Biotin | - | - |
| 100 | PHPAAPSSWGPRK-Biotin | - | - |
| 102 | PAAPSSWGPRPRK-Biotin | - | - |
| 104 | APSSWGPRPRRYK-Biotin | - | - |
| 106 | SSWGPRPRRYTVK-Biotin | - | - |
| 108 | WGPRPRRYTVLSK-Biotin | - | - |
| 110 | GPPAAAPGHPLAPGPHPAAPSSWGPRPRRYK-biotin | - | - |

Based on the results in Table 9 above, it can be determined that 553G8G8 and 556F6B8 do not recognize the outer loop sequence, and 405B8H3, 409B11E12, and 409D4E10 recognize a region in the outer loop comprising the amino acid sequence SSWGPRPR (positions 90-97 of SEQ ID NO: 61), and 105F1E10 recognizes a region in the outer loop comprising the amino acid sequence APSSWGPR (positions 88-95 of SEQ ID NO: 61).

The results show that the epitopes bound by the antibody of the present invention are inconsistent with that bound by the LAG-3 antibody BMS986016 of BMS, and the antibody of the present invention will not infringe the epitope HPAAPSSW (positions 85-92 of SEQ ID NO: 61) protected by the patent CN102176921A of BMS.

Example 3 Determination of Amino Acid Sequences of Light and Heavy Chain Variable Regions Total RNA isolation: After the subclonal culture supernatant was tested for antigen binding, $1$-$5 \times 10^7$ hybridoma cells were collected by centrifugation. The cells were added with 1 mL Trizol, mixed and transferred to a 1.5 ml centrifuge tube, let stand for 5 min at room temperature; and added with 0.2 ml chloroform, shaked for 15 s, let stand for 2 min, and centrifuged at 4° C., 12000 g×5 min. Then the supernatant was taken and transferred to a new 1.5 ml centrifuge tube; and added with 0.5 ml isopropanol, gently mixed in the tube, let stand at room temperature for 10 min, and centrifuged at 4° C., 12000 g×15 min. The supernatant was discarded; and the tube was added with 1 ml 75% ethanol, and the precipitate was gently washed. The solution was centrifuged at 4° C., 12000 g×5 min, and the supernatant was discarded and the precipitate was dried, an appropriate amount of DEPC $H_2O$ was added in a water bath at 55° C. for 10 min for dissolution.

Reverse transcription and PCR: 1 μg tRNA was taken, and a 20 ul system was configured, added with reverse transcriptase and reacted at 42° C. for 60 minutes, and the reaction was terminated at 70° C. for 10 minutes. 50 μl PCR system was configured, comprising 1 μl cDNA, 25 pmol of each primer, 1 μl DNA polymerase and a matching buffer system, 250 μmol dNTPs. PCR program was set, comprising pre-denaturation 95° C. 3 min, denaturation 95° C. 30 s, annealing 55° C. 30 s, extension 72° C. 35 s, and further extension at 72° C. for 5 min after 35 cycles. Note: The extension temperature can be adjusted according to the actual situation.

Cloning and sequencing: 5 μl of PCR product was taken for agarose gel electrophoresis detection. Column recovery kit was used to purify the positive samples. Ligation reaction were performed in a 10 μl reaction system containing: sample 50 ng, T vector 50 ng, ligase 0.5 μl, and buffer 1 μl, and reacted at 16° C. for half an hour. 5 μl of the ligation product was taken and added to 100 μl of competent cells, ice bath for 5 minutes, then heat shock in a 42° C. water bath for 1 minute, and put back on ice for 1 minute, and added with 650 μl antibiotic-free SOC medium. The cells were resuscitated on a shaker at 37° C. at 200 RPM for 30 min, taken out with 200 μl and spreaded on LB solid medium containing antibiotics and incubated overnight at 37° C. in an incubator. On the next day, primers M13F and M13R on the T vector were used to configure a 30 μl PCR system. Colony PCR was performed, a pipette tip was used to dip the colony into the PCR reaction system and pipette, and 0.5 μl was aspirated onto another LB solid petri dish containing antibiotics to preserve the strain. After the PCR reaction was over, 5 μl of the reaction solution was take out for agar glycogel electrophoresis detection, and the positive samples were sequenced. Wherein, the steps of sequencing can be found in Kabat, Sequences of Proteins of Immunological Interest, National Institutes of Health, Bethesda, Md. (1991).

Figures 13A, 13B, 14A, 14B, 15:
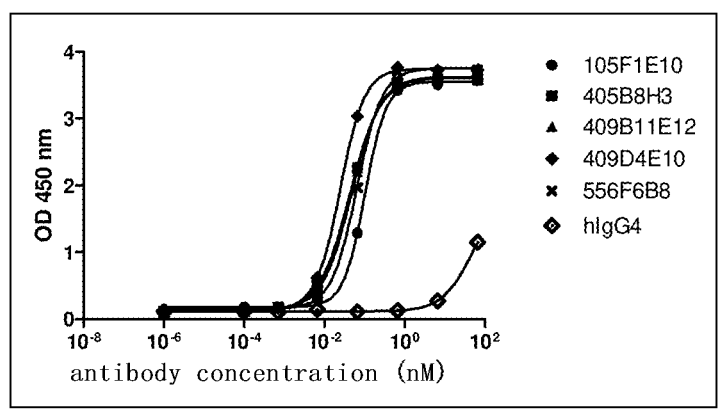
FIG. 13a shows protein and gene sequences of LAG-3 antibody 409D4E10 heavy chain variable region (SEQ ID NO: 33 is the amino acid sequence, and SEQ ID NO: 57 is the nucleotide sequence).
FIG. 13b shows protein and gene sequences of LAG-3 antibody 409D4E10 light chain variable region (SEQ ID NO: 37 is the amino acid sequence, and SEQ ID NO: 58 is the nucleotide sequence).
FIG. 14a shows protein and gene sequences of LAG-3 antibody 553G8G8 heavy chain variable region (SEQ ID NO: 41 is the amino acid sequence, and SEQ ID NO: 59 is the nucleotide sequence).
FIG. 14b shows protein and gene sequences of LAG-3 antibody 553G8G8 light chain variable region (SEQ ID NO: 45 is the amino acid sequence, and SEQ ID NO: 60 is the nucleotide sequence).
FIG. 15 shows the activities of LAG-3 mouse-human chimeric antibodies reaction with human LAG-3 extracellular domain protein in enzyme-linked immunosorbent assay.

Sequencing results: The heavy chain variable region protein and gene (DNA) sequences, and the light chain variable region protein and gene sequences of the antibody product of the present invention were as follows:

See FIG. 9a and FIG. 9b for antibody 105F1E10; FIG. 10a and FIG. 10b for antibody 405B8H3; FIG. 11a and FIG. 1b for antibody 556F6B8; FIG. 12a and FIG. 12b for antibody 409B11E12; FIG. 13a and FIG. 13b for antibody 409D4E10; FIG. 14a and FIG. 14b for antibody 553G8G8.

Example 4 Construction of Mouse-Human Chimeric Antibody, and Production and Purification of the Antibody Plasmid construction and preparation: The hybridoma antibody heavy chain variable region sequence was cloned into the pCP expression vector containing the signal peptide and human heavy chain antibody IgG4 constant region, and the light chain variable region was recombined to the pCP expression vector containing the signal peptide and human antibody light chain kappa (lambda) constant region, and the plasmids were verified by sequencing. Plasmids were extracted using alkaline lysis kit to increase the purity, filtered through a 0.22 m filter membrane for transfection.

Cell transfection: Freestyle 293F cells were used, and the medium was Freestyle 293 expression medium, added with 10% F68 to a final concentration of 0.1%, when used. During transfection, the cell density was cultured to 1-1.5× $10^6$ cells per milliliter; and the shaker was set to 37° C., 130 RPM, with a $CO_2$ concentration of 8%. 5 ml of medium was taken and mixed well with PEI (200 μg/ml). 5 ml of medium was taken and mixed well with a certain amount of plasmids (the amount of plasmids was 100 μg/ml). After 5 minutes, the two solutions were combined and mixed well, let stand for 15 minutes; and added slowly into the cells, being shaken while added, to avoid excessive concentration of PEI. And the mixed solution was cultured in a shaker. On the next day, it was added with peptone (sigma) to a final concentration of 0.5%. On the 5-7 day, the antibody titer of the culture medium was tested. On the 6-7 day, it was centrifuged (3500 RPM, 30 min) and filtered to collect the supernatant for purification.

Antibody purification: For continuously used endotoxin-free chromatography columns and Protein A fillers, 0.1M NaOH was used for treatment for 30 minutes, or 5 column volumes of 0.5M NaOH was used for washing; for long-term unused column materials and chromatography columns, at least 1M NaOH was used for soaking for 1 hour, and non-endotoxic water was used for rinsing to neutrality, and the column material was washed with 10 times the column volume of 1% Triton×100. 5 column volumes of PBS was used for equilibrate. The filtered cell supernatant was loaded on the column, and the flow-through liquid was collected if necessary. After loading the samples, the column was washed with 5 column volumes of PBS. Elution was carried out with 5 column volumes of 0.1M Glycine-HCl with pH3.0, and the eluate was collected, and neutralized with 1/10 volume of 1M Tris-HCl (1.5M NaCl) with pH8.5. After the antibodies harvested, they were dialyzed overnight in 1×PBS to avoid endotoxin contamination. After dialysis, spectrophotometry or a kit was used to determine the concentration, and HPLC-SEC was used to determine the purity of the antibody, and an endotoxin detection kit was used to detect the content of antibody endotoxin.

Figure 16:
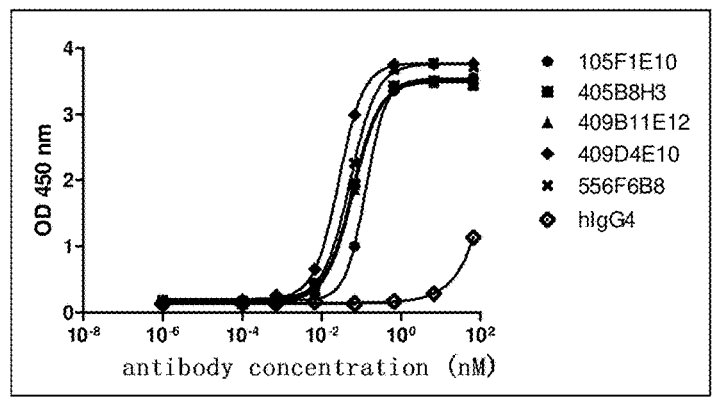
FIG. 16 shows the activities of LAG-3 mouse-human chimeric antibodies reaction with monkey LAG-3 extracellular domain protein in enzyme-linked immunosorbent assay.
Figure 17:
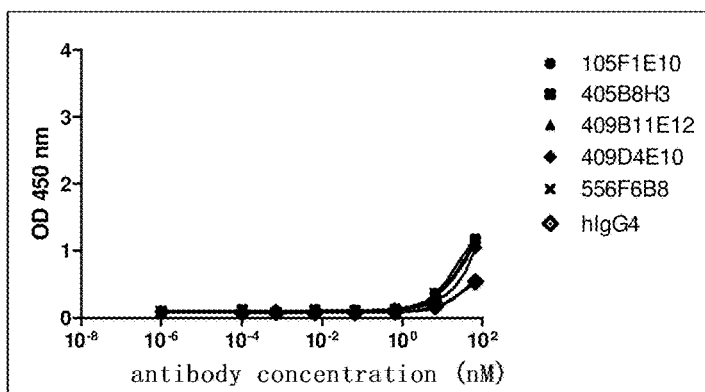
FIG. 17 shows the activities of LAG-3 mouse-human chimeric antibodies reaction with mouse LAG-3 extracellular domain protein in enzyme-linked immunosorbent assay.

Example 5 Identification of Mouse-Human Chimeric Antibody (I) Enzyme-Linked Immunosorbent Assay (ELISA) Detection of the Binding of Antibodies to LAG-3 Protein The amino acid sequence 23-450 of the extracellular region of the human LAG-3 protein described in preparation of Immunogen 1 in Example 1 (as shown in SEQ ID No: 61 in the sequence listing) was cloned into a pCpC vector containing human IgG Fc fragment (hFc), transfected into HEK293 cells, and the cell culture fluid was collected. And the human LAG-3 protein with hFc tag (here called hLAG-3-hFc protein) was obtained by purification. The amino acid sequence 18-449 of the extracellular region of the monkey LAG-3 protein (as shown in SEQ ID NO: 62 in the sequence listing) was cloned into a pCpC vector containing human IgG Fc fragment (hFc), transfected into HEK293 cells, and the cell culture fluid was collected. And the hFc tagged monkey LAG-3 protein (herein referred to as cLAG-3-hFc protein) was obtained by purification. The amino acid sequence 24-442 of the extracellular region of the murine LAG-3 protein (as shown in SEQ ID NO: 63 in the sequence listing) was cloned into a pCpC vector containing the human IgG Fc fragment (hFc), transfected into HEK293 cells, and the cell culture fluid was collected. And the mouse LAG-3 protein with hFc tag (herein referred to as mLAG-3-hFc protein) was obtained by purification. Purified human, monkey, and mouse LAG-3 extracellular domain proteins (hLAG-3-hFc, cLAG-3-hFc, mLAG-3-hFc) were diluted with PBS to a final concentration of 1.0 μg/ml, and then added as 100 μl per well to a 96-well ELISA plate. The plate was sealed with plastic film and incubated overnight at 4° C. The plate was washed 2 times with the plate washing solution (PBS+0.01% Tween20) on the next day, and added with the blocking solution (PBS+0.01% Tween20+1% BSA) and blocked at room temperature for 1-2 hours. The blocking solution was poured out, and the plate was added with 50-100 μl of the antibody sample to be tested to each well, incubated at 37° C. for 1-2 hours, and washed 2-3 times with a plate washing solution (PBS+0.01% Tween20). HRP (horseradish peroxidase) labeled secondary antibody was added, and the plate was incubated at 37° C. for 1-2 hours, and washed 2-3 times with a plate washing solution (PBS+0.01% Tween20). 100 μl of TMB substrate was added to each well. After incubated at room temperature for 15-30 minutes, the plate was added with 100 μl of stop solution (1.0N HCl) to each well. An ELISA plate reader (TiterMax 384plus, Molecular Device) was used to read the A450 nm value. The results are shown in FIG. 15, FIG. 16 and FIG. 17, Table 10, Table 11 and Table 12.

TABLE 10

Activities of LAG-3 mouse-human chimeric antibodies recation with human LAG-3 extracellular domain protein in enzyme-linked immunosorbent assay

| Clone ID | OD450 Antibody Concentration (nM) | | | | | | | |
|---|---|---|---|---|---|---|---|---|
| | 66.6670 | 6.6667 | 0.6667 | 0.0667 | 0.0067 | 0.0007 | 0.0001 | 0.0000 |
| 105F1E10 | 3.60 | 3.53 | 3.46 | 1.29 | 0.30 | 0.20 | 0.13 | 0.11 |
| 405B8H3 | 3.57 | 3.54 | 3.51 | 2.25 | 0.57 | 0.19 | 0.11 | 0.12 |
| 409B11E12 | 3.59 | 3.64 | 3.55 | 2.16 | 0.47 | 0.20 | 0.12 | 0.13 |
| 409D4E10 | 3.73 | 3.73 | 3.76 | 3.10 | 0.63 | 0.16 | 0.13 | 0.14 |
| 556F6B8 | 3.69 | 3.73 | 3.76 | 1.94 | 0.38 | 0.17 | 0.13 | 0.12 |
| hIgG control | 1.17 | 0.29 | 0.14 | 0.11 | 0.13 | 0.10 | 0.10 | 0.11 |

TABLE 11

Activities of LAG-3 mouse-human chimeric antibodies reaction with monkey LAG-3 extracellular domain protein in enzyme-linked immunosorbent assay

| Clone ID | OD450 Antibody Concentration (nM) | | | | | | | |
|---|---|---|---|---|---|---|---|---|
| | 66.6670 | 6.6667 | 0.6667 | 0.0667 | 0.0067 | 0.0007 | 0.0001 | 0.0000 |
| 105F1E10 | 3.59 | 3.53 | 3.38 | 1.00 | 0.26 | 0.16 | 0.14 | 0.15 |
| 405B8H3 | 3.46 | 3.55 | 3.39 | 1.96 | 0.46 | 0.21 | 0.15 | 0.15 |
| 409B11E12 | 3.44 | 3.47 | 3.36 | 1.91 | 0.39 | 0.17 | 0.14 | 0.14 |
| 409D4E10 | 3.77 | 3.79 | 3.78 | 3.05 | 0.64 | 0.27 | 0.19 | 0.18 |
| 556F6B8 | 3.72 | 3.78 | 3.70 | 2.43 | 0.46 | 0.21 | 0.18 | 0.19 |
| hIgG control | 1.16 | 0.29 | 0.18 | 0.14 | 0.19 | 0.13 | 0.14 | 0.13 |

TABLE 12

Activities of LAG-3 mouse-human chimeric antibodies reaction with mouse LAG-3 extracellular domain protein in enzyme-linked immunosorbent assay

| | OD450 Antibody Concentration (nM) | | | | | | | |
|---|---|---|---|---|---|---|---|---|
| Clone ID | 66.6670 | 6.6667 | 0.6667 | 0.0667 | 0.0067 | 0.0007 | 0.0001 | 0.0000 |
| 105F1E10 | 0.54 | 0.14 | 0.09 | 0.08 | 0.09 | 0.08 | 0.09 | 0.08 |
| 405B8H3 | 1.10 | 0.34 | 0.11 | 0.08 | 0.08 | 0.08 | 0.08 | 0.10 |
| 409B11E12 | 1.10 | 0.31 | 0.10 | 0.09 | 0.07 | 0.08 | 0.09 | 0.08 |
| 409D4E10 | 1.06 | 0.23 | 0.11 | 0.13 | 0.09 | 0.13 | 0.10 | 0.09 |
| 556F6B8 | 1.08 | 0.36 | 0.15 | 0.11 | 0.14 | 0.08 | 0.14 | 0.09 |
| hIgG control | 0.56 | 0.18 | 0.09 | 0.08 | 0.08 | 0.07 | 0.08 | |

The results show that the mouse-human chimeric antibody obtained in the present invention can bind to human and monkey LAG-3 extracellular domain proteins, and the activity of each antibody was close; while it cannot bind to mouse LAG-3 protein. Wherein, the IgG control is human IgG, and the data in the table is A450 nm values.

(II) Detection of the Binding of Antibodies to LAG-3 Expressing Cells by Flow Cytometry (FACS)

Figure 18:
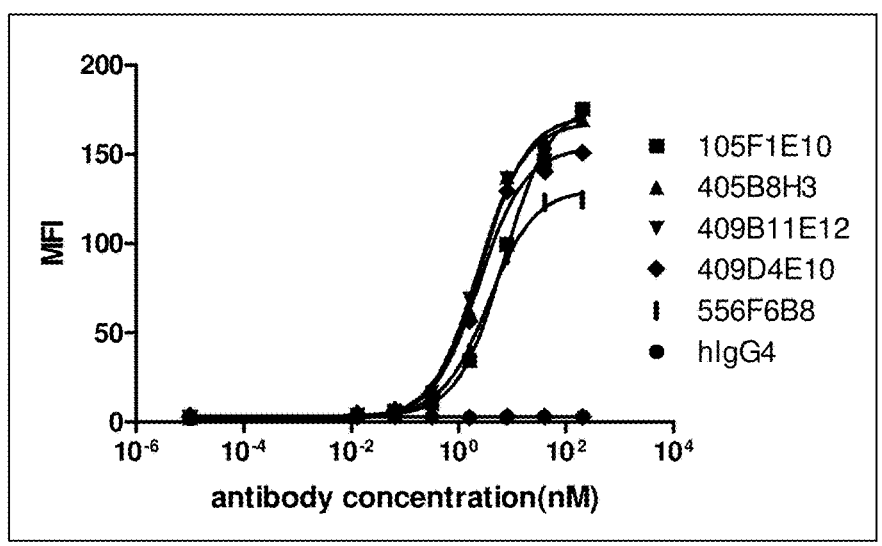
FIG. 18 shows the FACS detections of the binding reactions between LAG-3 mouse-human chimeric antibodies and HEK293-hLAG-3.
Figure 19:
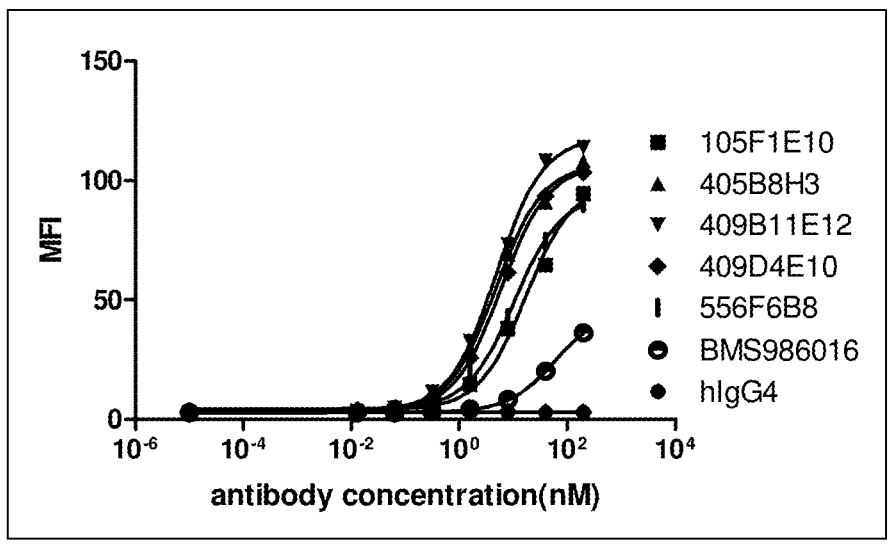
FIG. 19 shows the FACS detections of the binding reactions between LAG-3 mouse-human chimeric antibodies and HEK293-cLAG-3.

According to the experimental method in Example 2 (I), the binding activity of the obtained mouse-human chimeric LAG-3 antibody to the cell expressing LAG-3 was identified. The results are shown in FIG. 18 and FIG. 19, Table 13 and Table 14. Wherein, the IgG control was human IgG, and the data in the table is the average fluorescence intensity values of the cell populations measured by MFI.

The results show that the mouse-human chimeric antibody obtained in the present invention can bind human and monkey LAG-3 proteins on the cell surface. And the ability of the antibody of the present invention to bind to the monkey LAG-3 protein on the cell surface was stronger than that of the control antibody (BMS986016).

The sequence of monkey LAG-3 in the experiment was obtained from tissue samples of Chinese monkeys. The antibody of the present invention has a cross-binding reaction with monkey antigens, and can be applied to in vivo experiments in primates, for preclinical toxicology studies and preclinical pharmacokinetic studies.

TABLE 13

FACS detections of the binding reactions between LAG-3 mouse-human chimeric antibodies and HEK293-hLAG-3

| | Mean fluorescence intensity Antibody concentration (nM) | | | | | | | |
|---|---|---|---|---|---|---|---|---|
| Clone ID | 200.000 | 40.000 | 8.000 | 1.600 | 0.320 | 0.064 | 0.013 | 0.000 |
| 105F1E10 | 175.4 | 146.3 | 99.4 | 34.7 | 10.7 | 5.1 | 3.6 | 2.6 |
| 405B8H3 | 169.4 | 157.6 | 137.3 | 62.3 | 17.3 | 6.3 | 4.0 | 2.8 |
| 409B11E12 | 171.0 | 149.5 | 136.3 | 69.0 | 16.8 | 6.3 | 4.1 | 2.8 |
| 409D4E10 | 150.7 | 140.4 | 129.1 | 56.8 | 15.7 | 6.3 | 4.0 | 3.0 |
| 556F6B8 | 124.6 | 123.0 | 93.5 | 39.1 | 14.3 | 6.5 | 4.2 | 3.3 |
| hIgG control | 3.1 | 3.1 | 3.0 | 2.7 | 3.1 | 3.1 | 3.0 | 3.0 |

TABLE 14

FACS detections of the binding reactions between LAG-3 mouse-human chimeric antibodies and HEK293-cLAG-3

| | Mean fluorescence intensity Antibody Concentration (nM) | | | | | | | |
|---|---|---|---|---|---|---|---|---|
| Clone ID | 200.000 | 40.000 | 8.000 | 1.600 | 0.320 | 0.064 | 0.013 | 0.000 |
| 105F1E10 | 94.46 | 64.63 | 37.94 | 14.74 | 5.72 | 3.54 | 2.89 | 2.72 |
| 405B8H3 | 107.91 | 90.84 | 69.31 | 29.36 | 10.28 | 4.80 | 3.52 | 2.90 |
| 409B11E12 | 113.91 | 108.18 | 73.06 | 32.84 | 11.61 | 4.95 | 3.39 | 2.84 |
| 409D4E10 | 103.41 | 93.44 | 61.45 | 25.84 | 8.96 | 4.42 | 3.36 | 2.99 |
| 556F6B8 | 90.48 | 74.42 | 42.52 | 19.20 | 8.37 | 4.45 | 3.46 | 3.10 |
| BMS986016 | 36.16 | 20.16 | 8.35 | 4.41 | 3.37 | 2.83 | 2.85 | 2.93 |
| hIgG Control | 2.90 | 2.88 | 3.16 | 3.25 | 3.13 | 3.04 | 2.87 | 2.86 |

Figure 20:
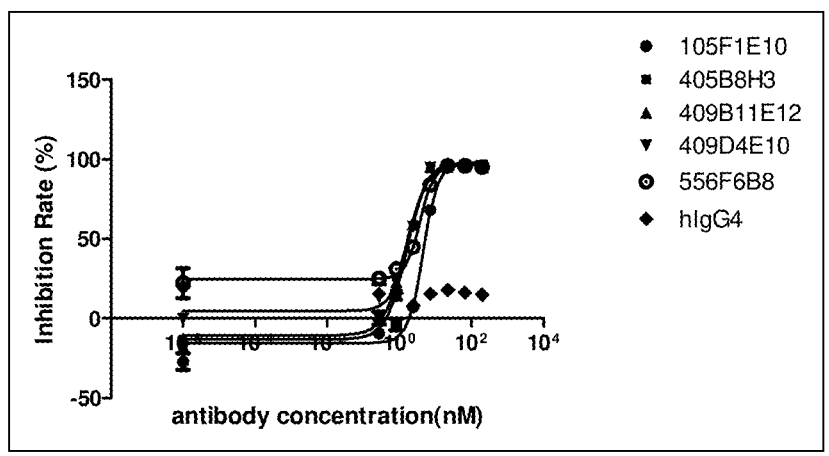
FIG. 20 shows the inhibitions of the LAG-3 mouse-human chimeric antibodies on the binding of LAG-3 protein to its receptor MHC II.

(III) Detection of the LAG-3 Antibody Blocking of the Binding of LAG-3 to its Ligands MHC II and LSECtin by LAG-3 Receptor Ligand Binding Assay (1) Detection of the LAG-3 Antibody Blocking of the Binding of LAG-3 to its Ligand MHC II by LAG-3 Receptor Ligand Binding Assay According to the experimental method in Example 2 (II), the blocking activity of the obtained mouse-human chimeric LAG-3 antibody was identified, and the test results are shown in FIG. 20 and Table 15.

TABLE 15

Inhibitions of the LAG-3 mouse-human chimeric antibodies on the binding of LAG-3 protein to its receptor MHC II

| Inhibition rate (%) | Antibody concentration (nM) | | | | | | | |
|---|---|---|---|---|---|---|---|---|
| Clone number | 200.000 | 66.667 | 22.222 | 7.407 | 2.469 | 0.823 | 0.274 | 0.000 |
| 105F1E10 | 96.0 | 96.0 | 95.8 | 67.0 | 8.2 | −0.3 | −10.1 | −32.3 |
| 405B8H3 | 95.2 | 95.8 | 95.7 | 95.1 | 55.8 | 17.5 | 4.3 | −15.6 |
| 409B11E12 | 94.8 | 95.3 | 95.6 | 95.1 | 59.2 | 24.4 | 4.4 | −11.8 |
| 409D4E10 | 95.7 | 95.9 | 95.7 | 94.7 | 56.7 | 20.9 | 11.3 | −1.7 |
| 556F6B8 | 95.2 | 96.0 | 95.8 | 82.7 | 41.5 | 29.7 | 21.5 | 12.9 |
| hIgG control | 12.3 | 12.1 | 19.7 | 8.8 | 2.1 | 10.2 | 8.1 | 17.7 |

The results show that the mouse-human chimeric antibody LAG-3 antibody obtained in the present invention can block the binding of LAG-3 and the ligand MHCII to varying degrees.

Figure 21:
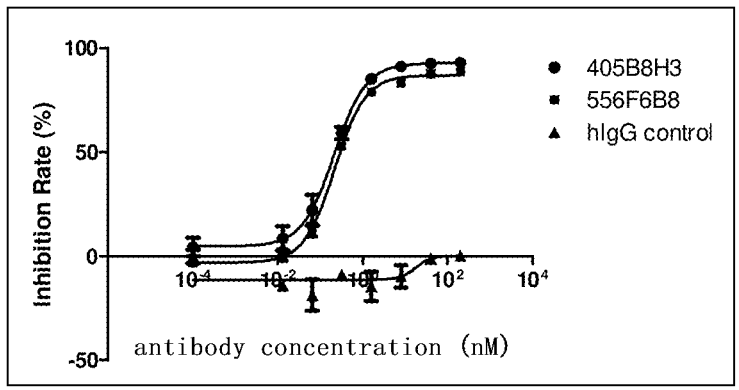
FIG. 21 shows the inhibitions of the LAG-3 mouse-human chimeric antibodies on the binding of LAG-3 protein to its receptor LSECtin.

(2) Detection of the LAG-3 Antibody Blocking of the Binding of LAG-3 to its Ligands LSECtin by LAG-3 Receptor Ligand Binding Assay LAG-3 extracellular domain protein (LAG-3-hFc) was diluted with PBS to a final concentration of 1.0 μg/mL, and then added to a 96-well ELISA plate as 100 μl per well. The plate was covered with a plastic film and incubated overnight at 4° C. The plate was washed twice with plate washing solution [PBS containing 0.01% (v/v) Tween 20] on the next day, added with blocking solution [PBS containing 0.01% (v/v) Tween 20 and 1% (w/w) BSA] and blocked for 2 hours at room temperature. The blocking solution was discarded, and the plate was added with 50 μl of the purified LAG-3 antibody test sample obtained in Example 2 to each well, then added with LSECtin protein (LSECtin-His), 50 μl per well, mixed well and incubated at 37° C. After 2 hours, the plate was washed 3 times with a plate washing solution [PBS containing 0.01% (v/v) Tween 20]. Anti-His tag HRP (horseradish peroxidase) diluent (purchased from GenScript) was added as 100 microliters per well, and after the plate was incubated for 2 hours at 37° C., it was washed with plate washing solution [PBS containing 0.01% (v/v) Tween 20] for 3 times. 100 μl of TMB substrate was added to each well. After incubated at room temperature for 30 minutes, the plate was added with 100 μl of stop solution (1.0N HCl) to each well. An ELISA plate reader (SpectraMax 384plus, Molecular Device) was used to read the A450 nm value. The test results are shown in FIG. 21 and Table 16, respectively.

TABLE 16

Inhibitions of the LAG-3 mouse-human chimeric antibodies on the binding of LAG-3 protein to its receptor LSECtin

| Inhibition rate (%) | Antibody concentration (nM) | | | | | | | |
|---|---|---|---|---|---|---|---|---|
| Clone number | 200.000 | 40.000 | 8.000 | 1.600 | 0.320 | 0.064 | 0.013 | 0.000 |
| 405B8H3 | 92.9 | 92.1 | 90.6 | 85.3 | 62.0 | 29.4 | 14.3 | 8.8 |
|  | 93.1 | 92.9 | 91.4 | 84.9 | 56.2 | 14.7 | 2.8 | −0.2 |
| 556F6B8 | 87.9 | 87.5 | 81.4 | 79.2 | 52.0 | 15.6 | 3.2 | −5.0 |
|  | 89.4 | 87.5 | 85.1 | 78.3 | 54.0 | 9.4 | −2.2 | −1.8 |
| hIgG control | 2.6 | 0.7 | −4.3 | −21.6 | −7.9 | −26.4 | −12.9 | 3.1 |
|  | −2.2 | −3.5 | −15.1 | −7.4 | −10.1 | −11.2 | −15.7 | −3.6 |

The results show that the mouse-human chimeric antibody LAG-3 antibody obtained in the present invention can block the binding of LAG-3 and the ligand LSECtin to varying degrees.

Figure 22:
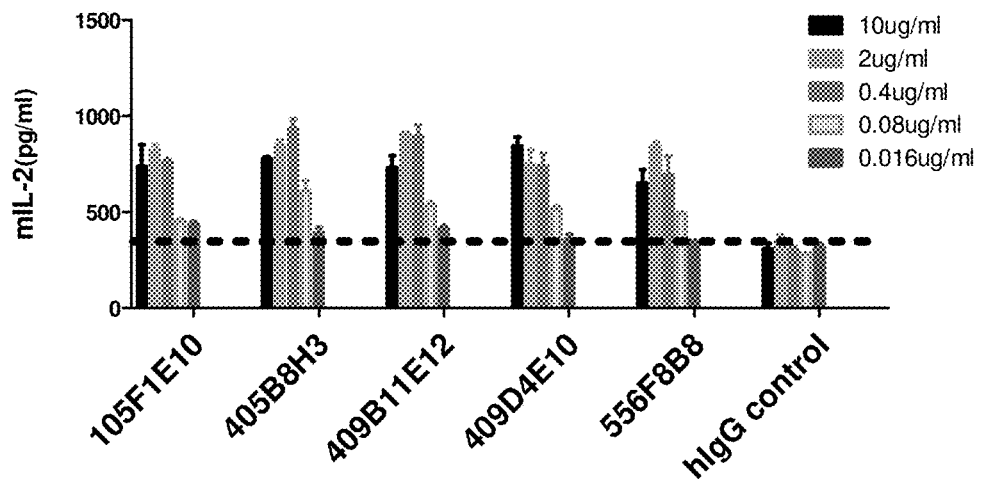
FIG. 22 shows the effects of LAG-3 mouse-human chimeric antibodies on IL-2 secretion in the antigen-specific T lymphocyte stimulation test.

(IV) Detection of the Effect of LAG-3 Antibody on Lymphocyte Activity by Antigen-Specific T Lymphocyte Stimulation Test Experimental methods were according to that in Example 2 (III). The results are shown in Table 17 and FIG. 22, wherein the IgG control was human IgG (hIgG), and the data in the table is the concentration of mouse IL-2.

TABLE 17

Effects of LAG-3 mouse-human chimeric antibodies on IL-2 secretion in the antigen-specific T lymphocyte stimulation test

| | IL-2 production, pg/ml | | | | | | | | | |
|---|---|---|---|---|---|---|---|---|---|---|
| | 10 ug/ml | | 2 ug/ml | | 0.4 ug/ml | | 0.08 ug/ml | | 0.016 ug/ml | |
| Clone ID | N = 1 | N = 2 | N = 1 | N = 2 | N = 1 | N = 2 | N = 1 | N = 2 | N = 1 | N = 2 |
| 105F1E10 | 850.3 | 626.7 | 852.7 | 791.7 | 779.4 | 757.1 | 437.0 | 466.9 | 451.9 | 419.5 |
| 405B8H3 | 770.2 | 789.2 | 875.8 | 824.7 | 882.8 | 985.9 | 665.6 | 559.2 | 366.2 | 420.5 |
| 409B11E12 | 670.6 | 795.2 | 914.1 | 915.3 | 835.1 | 953.5 | 525.0 | 554.9 | 401.5 | 433.4 |
| 409D4E10 | 890.4 | 801.3 | 824.9 | 673.4 | 803.9 | 677.6 | 497.5 | 533.5 | 384.4 | 333.5 |
| 556F8B8 | 583.8 | 722.0 | 818.2 | 866.0 | 793.6 | 599.2 | 499.0 | 490.7 | 348.1 | 352.6 |
| hIgG control | 338.5 | 276.6 | 381.5 | 317.0 | 322.5 | 286.2 | 285.8 | 282.0 | 335.7 | 297.5 |

The results show that the mouse-human chimeric antibody obtained in the present invention can stimulate IL-2 secretion in an antigen-specific T lymphocyte stimulation test, and the activity had a concentration gradient-dependent effect, indicating that LAG-3 antibody can reverse the inhibitory effect of LAG-3 on T cell activation. It can be seen from the measured results that the activity levels of the antibodies obtained in the present invention were comparable.

(V) Detection of the Effect of LAG-3 Antibody on Lymphocyte Activity by Lymphocyte Stimulation Test In the lymphocyte stimulation test, LAG-3 antibodies block the binding of LAG-3 protein and its receptor MHC II to relieve the inhibition of T lymphocyte activity, thereby stimulating the proliferation of T cells.

1. Peripheral Blood Mononuclear Lymphocyte PBMCs were Isolated from the Whole Blood Using Ficoll.

The freshly obtained whole blood was diluted with phosphate buffer PBS at a volume ratio of 1:1, to obtain diluted whole blood. A sterile pipette was used to gently spread the diluted whole blood on the surface of Ficoll (purchased from GE Healthcare). The volume ratio of Ficoll to diluted whole blood was 3:4. The solution was mixed without shaking, gradiently centrifuged at 400 g at room temperature 20° C. for 30 minutes. The centrifuge tube after centrifugation was divided into three layers, wherein the upper layer was plasma and the middle layer was milky white, which was mononuclear lymphocytes. A sterile pipette was used to gently aspirate the middle layer cells, collected in a new centrifuge tube, diluted to three times of volume with PBS phosphate buffer, and centrifuged at 100 g at room temperature for 10 minutes, then the supernatant was discarded. The lymphocytes were resuspended to 10 mL in PBS phosphate buffer, and the previous steps were repeated to remove the platelets. Finally, the lymphocytes were resuspended in 10 mL of multi-component RPMI1640 medium (purchased from Invitrogen) containing 10% fetal bovine serum for use, namely peripheral blood mononuclear lymphocytes PBMCs, and the percentages were mass percentages.

2. SEB-Dependent PBMC Stimulation Experiment

Before the test, the mouse-human chimeric antibody LAG-3 antibody diluted in equal volume ratio was prepared to obtain the sample solution to be tested.

The obtained peripheral blood mononuclear lymphocytes PBMCs were plated with $1\times10^5$ cells, 100 microliters per well, on a 96-well cell culture plate, and then the test sample solution was added to the culture plate and incubated at room temperature for 30 minutes. Finally, the superantigen SEB was added. Each reaction well contained 50 microliters of 400 ng/ml SEB. The volume of each reaction well was 200 μL. The reaction plate was incubated in a 37° C., 5% $CO_2$ incubator for 72 hours, and then the supernatant was collected. The supernatant was frozen at −20° C., and the percentage was the volume percentage.

3. Detection of Cytokine Interleukin IL-2 Enzyme-Linked Immunosorbent Assay in Cell Supernatant In the detection of cytokine interleukin IL-2 enzyme-linked immunosorbent assay in the cell supernatant, the R&D system related detection kit human IL-2 DuoSet ELISA (DY202) was used, and operated in accordance with the instructions. All test reagents except the tested antibodies were provided by the test kit.

The enzyme-linked immunosorbent assay to determine the cytokine interleukin IL-2 content in the cell supernatant used a double antibody sandwich ELISA kit (purchased from R&D Systems, IL-2 Cat #DY202). The experimental operation was strictly in accordance with the requirements of the kit instructions, and all test reagents were provided by the kit. The specific experiment was briefly described as follows. The IL-2 polyclonal antibody was coated on the ELISA microwell plate, sealed with plastic film and incubated overnight at 4° C. The plate was washed 4 times with the plate washing solution on the next day, and added with the blocking solution and blocked at room temperature for 1-2 hours. The plate was washed 4 times with the plate washing solution. The cell supernatant obtained in step 2 was used as the test sample. The standard and the test sample were incubated at room temperature for 2 hours. 400 microliters of washing solution was added to each well, the plate washing was repeated 4 times. Then horseradish peroxidase-labeled antibody against human IL-2 was added, and incubated for 2 hours at room temperature to form an immune complex with IL-2 on the microplate and the microwells were washed. The substrate was added for color development, protected from light at room temperature for 30 minutes. Finally the stop solution was added, and the absorbance at A450 nm was measured with a microplate reader.

Figure 23:
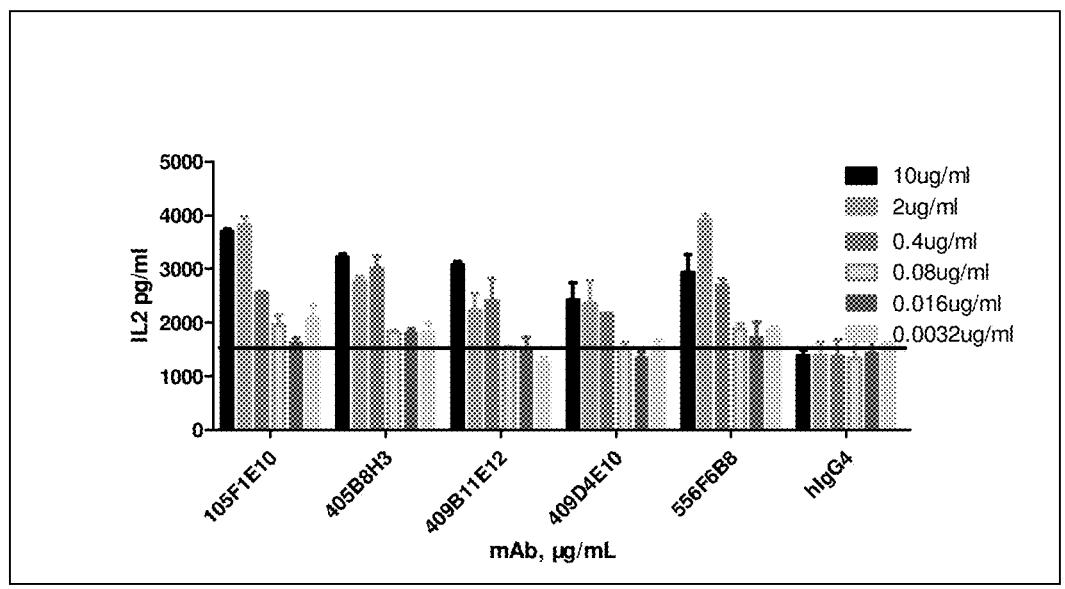
FIG. 23 shows the effects of LAG-3 mouse-human chimeric antibodies on IL-2 secretion in the SEB-dependent PBMC stimulation test.

The effects of LAG-3 antibodies on IL-2 secretion in the SEB-dependent PBMC stimulation experiment described in step 2 were detected. The results are shown in FIG. 23 and Table 18.

TABLE 18

Effects of LAG-3 mouse-human chimeric antibodies on IL-2 secretion in the SEB-dependent PBMC stimulation test

| | IL-2 production, pg/ml | | | | | | | | | | | |
|---|---|---|---|---|---|---|---|---|---|---|---|---|
| | 10 ug/ml | | 2 ug/ml | | 0.4 ug/ml | | 0.08 ug/ml | | 0.016 ug/ml | | 0.0032 ug/ml | |
| Clone ID | N = 1 | N = 2 | N = 1 | N = 2 | N = 1 | N = 2 | N = 1 | N = 2 | N = 1 | N = 2 | N = 1 | N = 2 |
| 105F1E10 | 3738 | 3649 | 3966 | 3663 | 2549 | 2571 | 2134 | 1772 | 1716 | 1521 | 2336 | 1839 |
| 405B8H3 | 3279 | 3157 | 2696 | 2854 | 2793 | 3241 | 1805 | 1845 | 1879 | 1774 | 2005 | 1604 |
| 409B11E12 | 3138 | 3014 | 2539 | 1915 | 2825 | 1989 | 1549 | 1530 | 1725 | 1226 | 1339 | 1191 |
| 409D4E10 | 2737 | 2098 | 2774 | 1937 | 2173 | 2156 | 1628 | 1422 | 1254 | 1446 | 1662 | 1243 |
| 556F6B8 | 2610 | 3259 | 3796 | 4011 | 2572 | 2812 | 1778 | 1977 | 1432 | 2012 | 1780 | 1913 |
| hIgG4 | 1277 | 1490 | 1128 | 1629 | 1063 | 1682 | 1019 | 1654 | 1224 | 1658 | 1624 | 1594 |

The results show that in the SEB-dependent PBMC lymphocyte stimulation test, the antibodies obtained in the present invention can increase the secretion of IL-2 by PBMCs, and the activity had a concentration gradient-dependent effect, indicating that LAG-3 antibody can reverse the inhibitory effect of LAG-3 on T cell activation. It can be seen from the measured results that the activity levels of the antibodies obtained in the present invention were comparable. Wherein, the hIgG control was human IgG, and the data in the table is the IL-2 value (pg/mL).

(VI) Antibody Affinity Test

First, anti-human Fc IgG was immobilized on the surface of the CM5 chip to 6000-10000 RU by amino coupling method, with FC1 as the reference channel. The coupling process was as follows: a freshly prepared 1:1 mixture of 50 mM NHS and 200 mM EDC was activated for 7 minutes, then injected with 10-50 ug/ml anti-human Fc IgG diluted in 10 mM sodium acetate ph5.0 buffer. The remaining activated sites were blocked with 1M ethanolamine. Then, HBS-EP+ buffer was used to dilute the antibody to be tested to 5 ug/ml (adjustable according to the capture level) and the antibodies were captured on the chip at a flow rate of 10 ul/min to obtain a response value of about 100~300 RU. Then the antigen protein was diluted to 100 nM (the highest concentration was tentatively 100 nM), and flew through the chip surface at a flow rate of 30 ul/min. If enough signal value was obtained, the antigen-protein was diluted by several concentration gradients, and flew through the chip surface respectively. At the end of each cycle, the chip surface was regenerated with 10 mM Glycine at pH 1.5. The kinetic rate constant needed to be subtracted from the blank control, and the data was fitted with the global fit analysis method 1:1 combination model. The dissociation equilibrium rate constant (KD) was calculated according to the following formula: KD=kd/ka. The results are shown in Table 19.

TABLE 19

Analysis and determination of anti-LAG-3 antibody affinity

| Clone ID | ka (1/Ms) | kd (1/s) | KD (M) |
|---|---|---|---|
| 105F1E10 | 3.85E+04 | 9.66E−05 | 2.51E−09 |
| 405B8H3 | 8.04E+04 | 1.58E−04 | 1.96E−09 |
| 556F6B8 | 1.22E+05 | 4.59E−04 | 3.77E−09 |

The results show that the KD values of the antibodies obtained in the present invention were all at the nanomolar (nM) level and were comparable to the tool antibodies, indicating that these antibodies had a good affinity for human LAG-3 ECD. Wherein, the 405B8H3 antibody had the best affinity for human LAG-3 ECD.

Example 6 Preparation, Identification and Hot Spot Mutation of Humanized Antibody (I) Preparation of Humanized Antibody The heavy chain and light chain variable regions of clones 405B8H3 and 556F6B8 were used as humanization templates.

Through sequence alignment (NCBI-Igblast), the germline gene sequence with the highest homology to the candidate antibody 405B8H3 heavy chain variable region and light chain variable region was selected as the variable region transplantation skeleton: IGHV1-46*01 and IGKV1-16*01. After the human antibody framework was selected, homology modeling was used to predict the key amino acids that may determine the structure in the mouse antibody constant region, and the grafted framework region was designed for back mutation.

According to the above principles, 4 heavy chain variable region sequences (405B8H3 VH_g0, 405B8H3 VH_g1, 405B8H3 VH_g2, and 405B8H3 VH_g3) (see Table 20) and 3 light chain variable region sequences (405B8H3 VL_g0, 405B8H3 VL_g1, and 405B8H3 VL_g2) (see Table 21) were designed respectively, followed by cross-combination for expression, for a total of 12 expression combinations, see Table 22.

TABLE 20

Back mutation design after homology modeling of 405B8H3 heavy chain variable region

| | |
|---|---|
| 405B8 H3 | VHQVQLQQSGAELVRPGASVTLSCKASGYTFTDYEMHWVKQTPVHGLEWIGATDPE TGNSAYNQKFKGKAIMTADKSSSTAYMELRSLTSEDSAVYYCISTGWNDWGQGT SLTVSS (SEQ ID NO: 1) |
| IGHV1-46* 01/JH6b | QVQLVQSGAEVKKPGASVKVSCKASGYTFTSYYMHWVRQAPGQGLEWMGIINP SGGSTSYAQKFQGRVTMTRDTSTSTVYMELSSLRSEDTAVYYCISTGMDVWGQG TTVTVSS (SEQ ID NO: 86) |
| 405B8H3 VH_g0 | QVQLVQSGAEVKKPGASVKVSCKASGYTFTDYEMHWVRQAPGQGLEWMGATD PETGNSAYNQKFKGRVTMTRDTSTSTVYMELSSLRSEDTAVYYCISTGWNDWGQ GTTVTVSS (SEQ ID NO: 64) |
| 405B8H3 VH_g1 | QVQLVQSGAEVKKPGASVKVSCKASGYTFTDYEMHWVRQAPGQGLEWMGATD PETGNSAYNQKFKGRVTMTADKSTSTVYMELSSLRSEDTAVYYCISTGWNDWGQ GTTVTVSS (SEQ ID NO: 66) |
| 405B8H3 VH_g2 | QVQLVQSGAEVKKPGASVKVSCKASGYTFTDYEMHWVRQAPGQGLEWIGATDP ETGNSAYNQKFKGRATMTADKSTSTAYMELSSLRSEDTAVYYCISTGWNDWGQ GTTVTVSS (SEQ ID NO: 68) |
| 405B8H3 VH_g3 | QVQLVQSGAEVKKPGASVKVSCKASGYTFTDYEMHWVKQAPGQGLEWIGATDP ETGNSAYNQKFKGKATMTADKSTSTAYMELSSLRSEDTAVYYCISTGWNDWGQ GTTVTVSS (SEQ ID NO: 87) |

TABLE 21

Back mutation design after homology modeling of 405B8H3 light chain variable region

| | |
|---|---|
| 405B8H3 | VLDIKMTQSPSSMYASLGERVTITCKASQDINSYLSWFQQKPGKSPKTLIYRADRLLD GVPSRFSGSGSGQDYSLTISSLEYGDMGIYYCLQYDEFPYTFGGGTKLEIK (SEQ ID NO: 5) |
| IGKV1-16* 01/JK2 | DIQMTQSPSSLSASVGDRVTITCRASQGISNYLAWFQQKPGKAPKSLIYAASSLQSG VPSRFSGSGSGTDFTLTISSLQPEDFATYYCQQYNSYPYTFGQGTKLEIK (SEQ ID NO: 88) |
| 405B8H3 VL_g0 | DIQMTQSPSSLSASVGDRVTITCKASQDINSYLSWFQQKPGKAPKSLIYRADRLLD GVPSRFSGSGSGTDFTLTISSLQPEDFATYYCLQYDEFPYTFGQGTKLEIK (SEQ ID NO: 76) |
| 405B8H3 VL_g1 | DIQMTQSPSSLSASVGDRVTITCKASQDINSYLSWFQQKPGKAPKSLIYRADRLLD GVPSRFSGSGSGQDYTLTISSLQPEDFATYYCLQYDEFPYTFGQGTKLEIK (SEQ ID NO: 78) |
| 405B8H3 VL_g2 | DIKMTQSPSSLSASVGDRVTITCKASQDINSYLSWFQQKPGKSPKSLIYRADRLLDG VPSRFSGSGSGQDYTLTISSLQPEDFATYYCLQYDEFPYTFGQGTKLEIK (SEQ ID NO: 89) |

TABLE 22

405B8H3 humanized antibody expression combination

| | 405B8H3 VH.g0 | 405B8H3 VH.g1 | 405B8H3 VH.g2 | 405B8H3 VH.g3 |
|---|---|---|---|---|
| 405B8H3 VL.g0 | 405B8H3-1 | 405B8H3-2 | 405B8H3-3 | 405B8H3-4 |
| 405B8H3 VL.g1 | 405B8H3-5 | 405B8H3-6 | 405B8H3-7 | 405B8H3-8 |
| 405B8H3 VL.g2 | 405B8H3-9 | 405B8H3-10 | 405B8H3-11 | 405B8H3-12 |

Through sequence alignment (NCBI-Igblast), the germline gene sequence with the highest homology to the candidate antibody 556F6B8 heavy chain variable region and light chain variable region was selected as the variable region transplantation skeleton: G V459*01 and IGKV19*01. After the human antibody framework was selected, homology modeling was used to predict the key amino acids that may determine the structure in the mouse antibody constant region, and the grafted framework region was designed for back mutation.

According to the above principles, 4 heavy chain variable region sequences (556F6B8 VH_g0, 556F6B8 VH_g1, 556F6B8 VH_g2, and 556F6B8 VH_g3) (see Table 23) and 3 light chain variable region sequences (556F6B8 VL_g0, 556F6B8 VL_g1, and 556F6B8 VL_g2) (see Table 24) were designed respectively, followed by cross-combination for expression, for a total of 12 expression combinations, see Table 25.

TABLE 23

Back mutation design after homology modeling of 556F6B8 heavy chain variable region

| | |
|---|---|
| 556F6B8 VH | RVQLKQSGPGLVQPSQSLSITCTVSGFSLIKYGVHWVRQSPGEGLEWLGVIWRGGI TDYNAAFMSRLSITKDNSKSQVFFKMNSLQADDTAIYYCAKWDGPLAMDYWGQ GTSVTVSS (SEQ ID NO: 9) |
| IGHV4-59* 01/JH6b | QVQLQESGPGLVKPSETLSLTCTVSGGSISSYYWSWIRQPPGKGLEWIGYIYYSGS TNYNPSLKSRVTISVDTSKNQFSLKLSSVTAADTAVYYCARWFGELLMDVWGQG TTVTVSS (SEQ ID NO: 90) |
| 556F6B8VH_ g0 | QVQLQESGPGLVKPSETLSLTCTVSGGSISKYGVHWIRQPPGKGLEWIGVIWRGGI TDYNAAFMSRVTISVDTSKNQFSLKLSSVTAADTAVYYCARWDGPLAMDYWGQ GTTVTVSS (SEQ ID NO: 91) |
| 556F6B8VH_ g1 | QVQLQESGPGLVKPSETLSLTCTVSGFSIIKYGVHWIRQPPGKGLEWIGVIWRGGIT DYNAAFMSRVTISVDTSKNQFSLKLSSVTAADTAVYYCARWDGPLAMDYWGQG TTVTVSS (SEQ ID NO: 92) |
| 556F6B8 VH_g2 | QVQLQESGPGLVKPSETLSLTCTVSGFSLIKYGVHWIRQPPGKGLEWIGVIWRGGI TDYNAAFMSRVTISKDTSKSQVSLKLSSVTAADTAVYYCARWDGPLAMDYWGQ GTTVTVSS (SEQ ID NO: 72) |
| 556F6B8VH_ g3 | RVQLQESGPGLVKPSETLSLTCTVSGFSLIKYGVHWIRQPPGKGLEWIGVIWRGGI TDYNAAFMSRVTISKDTSKSQVSLKLSSVTAADTAVYYCAKWDGPLAMDYWGQ GTTVTVSS (SEQ ID NO: 93) |

TABLE 24

Back mutation design after homology modeling of 556F6B8 light chain variable region

| | |
|---|---|
| 556F6B8 VL | DIVMTQSHKFLSTSVGDRVSITCKASQDVGTTVAWYQQKPGQSPKLLIYWASTRH TGVPDRFTGSGSGTDFTLTISNVQSEDLADYFCQQYSSYPYTFGGGTKLEIK (SEQ ID NO: 13) |
| IGKV1-9* 01/JK2 | DIQLTQSPSFLSASVGDRVTITCRASQGISSYLAWYQQKPGKAPKLLIYAASTLQSG VPSRFSGSGSGTEFTLTISSLQPEDFATYYCQQLNSYPYTFGQGTKLEIK (SEQ ID NO: 94) |
| 556F6B8VL_ g0 | DIQLTQSPSFLSASVGDRVTITCKASQDVGTTVAWYQQKPGKAPKLLIYWASTRH TGVPSRFSGSGSGTEFTLTISSLQPEDFATYYCQQYSSYPYTFGQGTKLEIK (SEQ ID NO: 80) |
| 556F6B8VL_ g1 | DIVLTQSPSFLSASVGDRVTITCKASQDVGTTVAWYQQKPGKAPKLLIYWASTRH TGVPSRFSGSGSGTEFTLTISSLQPEDFATYYCQQYSSYPYTFGQGTKLEIK (SEQ ID NO: 82) |
| 556F6B8 VL_g2 | DIVLTQSPSFLSASVGDRVTITCKASQDVGTTVAWYQQKPGKSPKLLIYWASTRHT GVPSRFSGSGSGTEFTLTISSLQPEDFATYYCQQYSSYPYTFGQGTKLEIK (SEQ ID NO: 95) |

TABLE 25

556F6B8 humanized antibody expression combination

| | 556F6B8 VH.g0 | 556F6B8 VH.g1 | 556F6B8 VH.g2 | 556F6B8 VH.g3 |
|---|---|---|---|---|
| 556F6B8 VL.g0 | 556F6B8-1 | 556F6B8-2 | 556F6B8-3 | 556F6B8-4 |
| 556F6B8 VL.g1 | 556F6B8-5 | 556F6B8-6 | 556F6B8-7 | 556F6B8-8 |
| 556F6B8 VL.g2 | 556F6B8-9 | 556F6B8-10 | 556F6B8-11 | 556F6B8-12 |

Vector construction: The experimental method was according to that of Example 4. The heavy chain variable region sequence and the light chain variable region sequence were cloned into the pCP expression vector containing the signal peptide and the human antibody IgG4 constant region, and verified by sequencing.

Preparation of Humanized Antibody:

Cell transfection: The experimental method was according to that of Example 4. Freestyle 293F cells were used to transfect the constructed plasmid into the cells, cultured for 6-7 days, and the supernatant was filtered and collected for purification.

Antibody purification: The experimental method was according to that of Example 4. An endotoxin-free Protein A chromatography column was used to purify the cell culture supernatant and harvest the antibody. Then they were dialyzed overnight in 1×PBS to avoid endotoxin contamination.

The obtained antibody was tested and analyzed for protein concentration and purity. The yield and purity analysis results of all antibodies were normal.

(II) Identification of Humanized Antibodies

Figure 24:
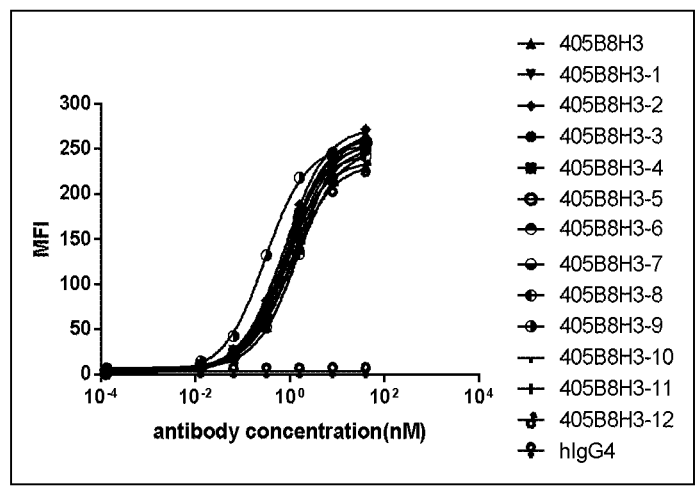
FIG. 24 shows the FACS detection of the binding reaction between 405B8H3 humanized antibody and HEK293-hLAG-3.
Figure 25:
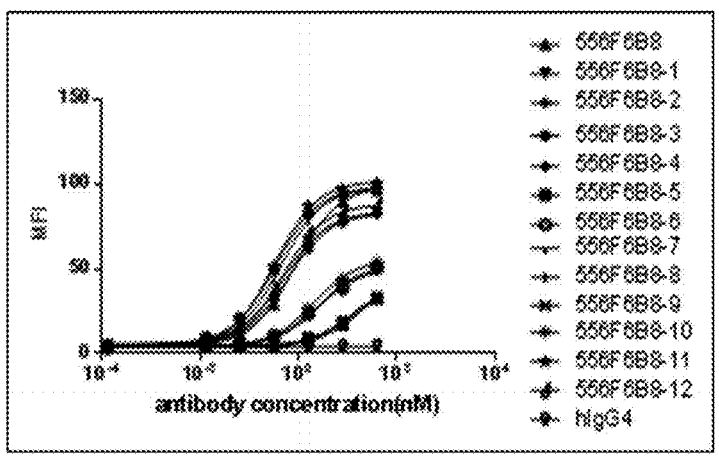
FIG. 25 shows the FACS detection of the binding reaction between 556F6B8 humanized antibody and HEK293-hLAG-3.

A. The binding of antibodies to LAG-3 expressing cells was detected by Flow cytometry (FACS), wherein the method was according to that of Example 5. The results are shown in Table 26 and FIG. 24 as well as Table 27 and FIG. 25. All the antibodies obtained can bind to human LAG-3 on the cell surface. Wherein, the IgG control was human IgG, and the data in the table is the average fluorescence intensity values of the cell populations measured by MFI.

TABLE 26

FACS detection of the binding reaction between 405B8H3 humanized antibody and HEK293-hLAG-3

| Clone ID | Mean fluorescence intensity Antibody concentration (nM) | | | | | |
|---|---|---|---|---|---|---|
| | 40 | 8 | 1.6 | 0.32 | 0.064 | 0.013 | 0 |
| 405B8H3 | 266 | 226 | 139 | 54 | 19 | 9 | 4 |
| 405B8H3-1 | 257 | 244 | 178 | 73 | 26 | 11 | 4 |
| 405B8H3-2 | 272 | 245 | 188 | 82 | 27 | 11 | 4 |
| 405B8H3-3 | 253 | 230 | 173 | 74 | 26 | 11 | 4 |
| 405B8H3-4 | 251 | 217 | 151 | 63 | 23 | 10 | 4 |
| 405B8H3-5 | 257 | 243 | 174 | 62 | 21 | 9 | 4 |
| 405B8H3-6 | 254 | 242 | 179 | 66 | 21 | 9 | 4 |
| 405B8H3-7 | 252 | 230 | 163 | 62 | 21 | 9 | 4 |
| 405B8H3-8 | 242 | 213 | 134 | 52 | 19 | 8 | 4 |
| 405B8H3-9 | 249 | 246 | 218 | 132 | 43 | 14 | 4 |
| 405B8H3-10 | 238 | 229 | 184 | 82 | 25 | 11 | 4 |
| 405B8H3-11 | 230 | 220 | 164 | 71 | 25 | 11 | 4 |
| 405B8H3-12 | 229 | 207 | 142 | 61 | 23 | 11 | 4 |
| hIgG control | 4 | 4 | 4 | 4 | 4 | 4 | 4 |

TABLE 27

FACS detection of the binding reaction between 556F6B8 humanized antibody and HEK293-hLAG-3

| Clone ID | Mean fluorescence intensity Antibody concentration (nM) | | | | | |
|---|---|---|---|---|---|---|
| | 40 | 8 | 1.6 | 0.32 | 0.064 | 0.013 | 0 |
| 556F6B8 | 96 | 90 | 67 | 29 | 12 | 6 | 4 |
| 556F6B8-1 | 33 | 19 | 9 | 5 | 4 | 4 | 4 |
| 556F6B8-2 | 49 | 37 | 23 | 10 | 5 | 4 | 4 |
| 556F6B8-3 | 98 | 94 | 83 | 49 | 21 | 10 | 4 |
| 556F6B8-4 | 82 | 77 | 62 | 32 | 14 | 7 | 4 |
| 556F6B8-5 | 32 | 16 | 8 | 5 | 4 | 4 | 4 |
| 556F6B8-6 | 50 | 39 | 23 | 10 | 6 | 4 | 4 |
| 556F6B8-7 | 98 | 93 | 79 | 44 | 18 | 8 | 4 |
| 556F6B8-8 | 83 | 79 | 64 | 36 | 15 | 8 | 4 |
| 556F6B8-9 | 33 | 18 | 9 | 5 | 4 | 4 | 4 |
| 556F6B8-10 | 54 | 44 | 27 | 11 | 6 | 4 | 4 |
| 556F6B8-11 | 100 | 97 | 87 | 51 | 20 | 9 | 4 |
| 556F6B8-12 | 87 | 83 | 70 | 36 | 15 | 8 | 4 |
| hIgG control | 4 | 4 | 4 | 4 | 4 | 4 | 4 |

B. The LAG-3 antibody affinity constant was determined by the same method as in Example 5.

The affinity of the antibody after humanization was evaluated, and the results are shown in Table 28. The results show that the KD values of the antibodies obtained in the present invention were all at the nanomolar (nM) level, and the affinities of the antibodies after humanization transformation were equivalent to those of the corresponding mouse-human chimeric antibodies.

TABLE 28

Analysis and determination of anti-LAG-3 antibody affinity

| Clone ID | ka (1/Ms) | kd (1/s) | KD (M) |
|---|---|---|---|
| 405B8H3 | 6.395E+04 | 1.652E−04 | 2.583E−09 |
| 405B8H3-1 | 1.001E+05 | 2.543E−04 | 2.539E−09 |
| 405B8H3-2 | 1.096E+05 | 1.844E−04 | 1.682E−09 |
| 405B8H3-6 | 9.488E+04 | 1.932E−04 | 2.037E−09 |
| 405B8H3-7 | 9.643E+04 | 3.165E−04 | 3.282E−09 |
| 556F6B8 | 1.341E+05 | 4.548E−04 | 3.392E−09 |
| 556F6B8-3 | 1.406E+05 | 4.648E−04 | 3.307E−09 |
| 556F6B8-7 | 1.393E+05 | 4.530E−04 | 3.252E−09 |

(III) Hot Spot Mutations of Humanized Antibodies

The hot spots of antibody 405B8H3-1 were subjected to point mutations. The 405B8H3-1 antibody had a mutable site, and the asparagine D at position 56 of the light chain was mutated to glutamate E.

For the vector construction and preparation of hot-spot mutated antibodies, the methods were the same as the vector construction and preparation of humanized antibodies in Example 6. The obtained antibody with hot spot mutations was tested and analyzed for protein concentration and purity. The yield and purity analysis results of all antibodies were normal.

Activity Identification of Hot Spot Mutated Antibodies

A. Detection of the Binding of Antibodies to LAG-3 Expressing Cells by Flow Cytometry (FACS)

Figure 26:
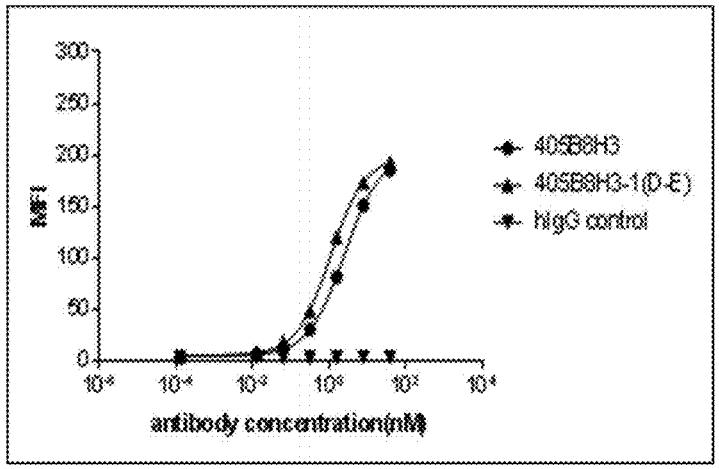
FIG. 26 shows the FACS detection of the binding reaction between the hot-spot mutant antibody and HEK293-hLAG-3.

The method was the same as that in Example 5. The results are shown in Table 29 and FIG. 26. Both hot-spot mutated antibodies and chimeric antibodies can bind to human LAG-3 on the cell surface. Wherein, the IgG control was human IgG, and the data in the table is the average fluorescence intensity values of the cell populations measured by MH.

TABLE 29

FACS detection of the binding reaction of hot-spot mutated antibody with HEK293-hLAG-3

| Clone ID | Mean fluorescence intensity Antibody concentration (nM) | | | | | |
|---|---|---|---|---|---|---|
| | 40 | 8 | 1.6 | 0.32 | 0.064 | 0.013 | 0 |
| 405B8H3 | 185 | 152 | 80 | 31 | 12 | 6 | 3 |
| 405B8H3-1 (D→E) | 192 | 172 | 123 | 47 | 18 | 8 | 3 |
| hIgG control | 3 | 3 | 3 | 3 | 3 | 3 | 3 |

Figure 27:
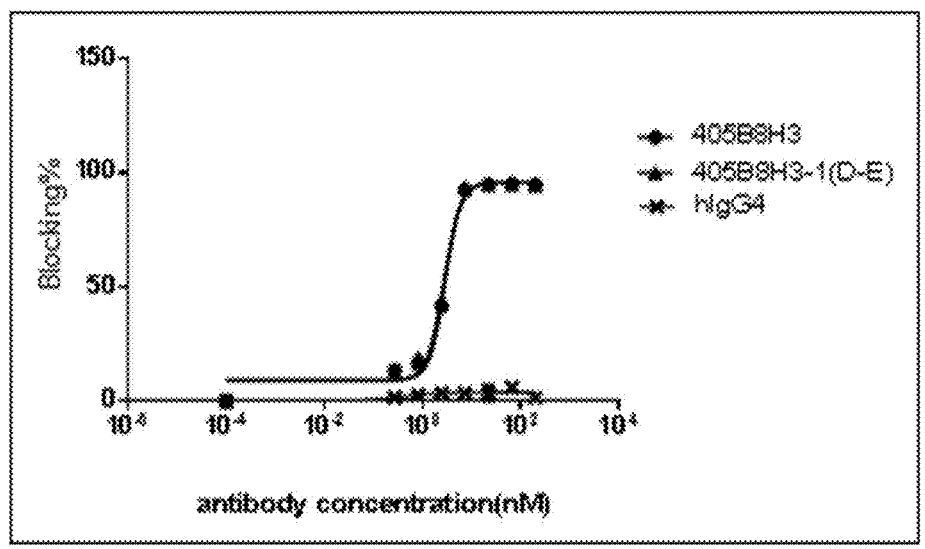
FIG. 27 shows the inhibition of the hot-spot mutant antibody on the binding of LAG-3 protein to its receptor MHC II, wherein the ordinate is the inhibition rate % (blocking %).

B. Detection of the Antibody Blocking of the Binding of LAG-3 to its Ligand MHC II by LAG-3 Receptor Ligand Binding Assay Experimental method was according to that of Example 2 (II). The test results are shown in Table 30 and FIG. 27, respectively. The results show that both hot spot mutated antibodies and mouse-human chimeric antibodies can block the binding of LAG-3 to the ligand MHCII, and their activities were equivalent.

TABLE 30

Inhibitions of the hot-spot mutated antibodies on the binding of LAG-3 protein to its receptor MHC II

| Inhibition rate (%) | Antibody concentration (nM) | | | | | | | |
|---|---|---|---|---|---|---|---|---|
| Clone ID | 200.000 | 66.667 | 22.222 | 7.407 | 2.469 | 0.823 | 0.274 | 0.000 |
| 405B8H3 | 95 | 95 | 95 | 93 | 41 | 14 | 13 | 0 |
| 405B8H3-1 (D→E) | 94 | 95 | 95 | 93 | 43 | 17 | 12 | 0 |
| hIgG control | 1 | 4 | 0 | 1 | 3 | 2 | 0 | 0 |

Figure 28:
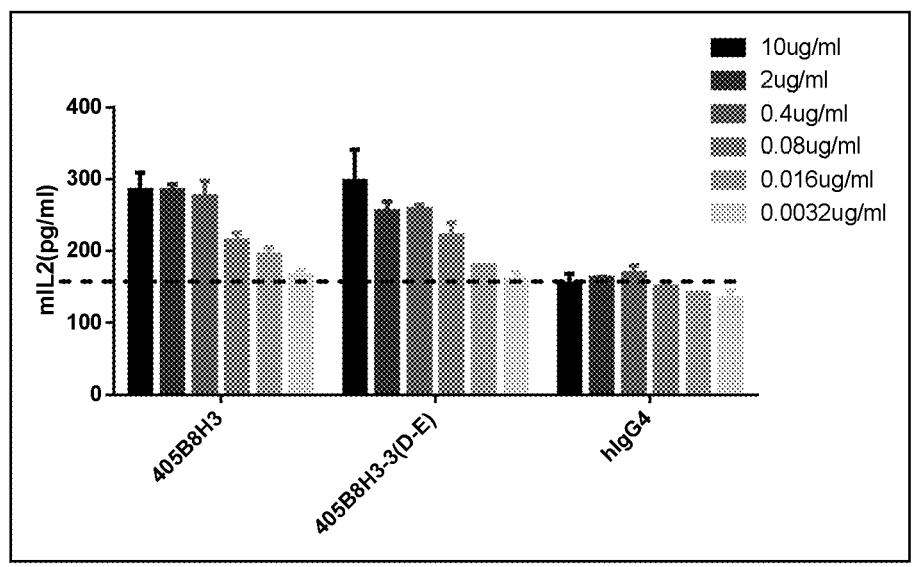
FIG. 28 shows the effect of the hot-spot mutated antibody on IL-2 secretion in antigen-specific T lymphocyte stimulation test.

C. Detection of the Effect of LAG-3 Antibody on Lymphocyte Activity by Antigen-Specific T Lymphocyte Stimulation Test Experimental methods were according to that in Example 2 (III). The results are shown in Table 31 and FIG. 28, wherein the IgG control was human IgG (hIgG), and the data in the table is the concentration of mouse IL-2.

The results show that both the hot spot mutation humanized antibody and the corresponding mouse-human chimeric antibody can stimulate IL-2 secretion in the antigen-specific T lymphocyte stimulation test, and had a concentration gradient-dependent effect and had comparable activities.

TABLE 31

Effect of hot spot mutated antibodies on IL-2 secretion in the antigen-specific T lymphocyte stimulation test

| | IL-2 production, pg/ml | | | | | | | | | | | |
|---|---|---|---|---|---|---|---|---|---|---|---|---|
| | 10 ug/ml | | 2 ug/ml | | 0.4 ug/ml | | 0.08 ug/ml | | 0.016 ug/ml | | 0.0032 ug/ml | |
| Clone ID | N = 1 | N = 2 | N = 1 | N = 2 | N = 1 | N = 2 | N = 1 | N = 2 | N = 1 | N = 2 | N = 1 | N = 2 |
| 405B8H3 | 261 | 309 | 277 | 293 | 297 | 255 | 225 | 204 | 185 | 205 | 160 | 173 |
| 405B8H3-1 (D-E) | 341 | 254 | 241 | 269 | 253 | 264 | 203 | 240 | 179 | 180 | 171 | 151 |
| hIgG Control | 142 | 168 | 164 | 162 | 159 | 179 | 157 | 145 | 141 | 143 | 144 | 123 |

D. Determination of LAG-3 Antibody Affinity Constant

The method was the same as that in Example 5. The affinity of hot-spot mutated antibodies was evaluated, and the results are shown in Table 32.

The results show that the KD values of the antibodies obtained in the present invention were all at the nanomolar (nM) level, and the affinity of the humanized antibody with hot spot mutation 405B8H3-1 (D→E) was increased by 1.5 times (3.11/2.03=1.5) compared with the corresponding mouse-human chimeric antibody 405B8H3, while the affinity of the humanized antibody 556F6B8-3 with hot spot mutation (mutation of asparagine D at position 100 of the heavy chain to glutamate E) was reduced to 1/12.5 (33.5/2.68=12.5), compared with the corresponding mouse-human chimeric antibody 405B8H3.

TABLE 32

Analysis and determination of hot-spot mutated anti-LAG-3 antibody affinity

| Clone ID | ka (1/Ms) | kd (1/s) | KD (M) |
|---|---|---|---|
| 405B8H3 | 5.28E+04 | 1.64E−04 | 3.11E−09 |
| 405B8H3-1 (D→E) | 7.75E+04 | 1.58E−04 | 2.03E−09 |
| 556F6B8 | 1.62E+05 | 4.33E−04 | 2.68E−09 |
| 556F6B8-3 (D→E) | 1.15E+05 | 0.003843 | 3.35E−08 |

DISCUSSION

At present, the clinical research of Bristol-Myers Squibb's LAG-3 antibody BMS986016 is mainly used for the treatment of malignant solid tumors, and it is also mainly concentrated on its combined use with other therapies or target drugs to develop antibodies with a wide range of indications to expand its applicable clinical symptoms, including unresectable metastatic melanoma, advanced solid cancer, breast cancer, endometrial cancer, ovarian cancer, kidney cancer, pancreatic cancer, recurrent glioblastoma, head and neck cancer, bladder cancer, metastasis colorectal cancer, gastrointestinal stromal tumors, acinar cell carcinoma, high-grade malignant solid tumors, non-small cell lung cancer, etc.

The activity of the antibody itself is affected by the sequences of the variable regions and the structure of the constant region. The sequences of the variable regions of an antibody determines the determinants of antigen recognition, binding affinity, and metabolic rate in vivo, which will affect its in vivo activity and even the clinical effects of different patients.

There is urgently needs to develop LAG-3 antibodies with higher yields to reduce the treatment cost of patients and benefit more patients in this field. Currently, tumor immunotherapy is expensive, and there is an urgent need to invent and produce new antibodies to reduce costs.

All publications mentioned herein are incorporated by reference as if each individual document was cited as a reference in the present application. It should be understood that, after reading the above teachings of the present invention, those skilled in the art can make various modifications and changes. These equivalent forms are also within the scope defined by the claims appended hereto.

Sequence Information of the Present Invention:

The amino acid sequences of the heavy chain variable regions (VH) and light chain variable regions (VL) of the LAG-3 antibodies and the nucleotide sequences encoding the heavy chain variable regions (VH) and light chain variable regions (VL), wherein, CDR1, CDR2, CDR3, CDR1', CDR2', CDR3' are underlined respectively:

mAb103-405B8H3-VH SEQ ID NO: 1
QVQLQQSGAELVRPGASVTLSCKASGYTFTDYEMHWVKQTPVHGLEWIG**ATDPETGNSAYN
QKFKGKAIMTADKSSSTAYMELRSLTSEDSAVYYCISTGWND**WGQGTSLTV S mAb103-405B8H3-VH SEQ ID NO: 49
CAGGTTCAACTGCAGCAGTCTGGGGCTGAGCTGGTGAGGCCTGGGGCTTCAGTG
ACGCTGTCCTGCAAGGCTTCGGGCTACACATTTACTGACTATGAAATGCACTG
GGTGAAGCAGACACCTGTGCATGGCCTGGAATGGATTGGA**GCCACTGATCCTG
AAACTGGTAATAGTGCCTACAATCAGAAGTTCAAGGGC**AAGGCCATAATGA
CTGCAGACAAATCCTCCAGCACAGCCTACATGGAGCTCCGCAGCCTGACATCTG
AGGACTCTGCCGTCTATTACTGTATATCAACTGGGTGGAATGACTGGGGCCAA
GGCACCAGTCTCACAGTCTCCTCA mAb103-405B8H3-VL SEQ ID NO: 5
DIKMTQSPSSMYASLGERVTITCKASQDINSYLSWFQQKPGKSPKTLIYRADRLLDGVPSR
FSGSGSGQDYSLTISSLEYGDMGIYYCLQYDEFPYTFGGGTKLEIK mAb103-405B8H3-VL SEQ ID NO: 50
GACATCAAGATGACCCAGTCTCCATCTTCCATGTATGCATCTCTAGGAGAGAGA
GTCACTATCACTTGCAAGGCGAGTCAGGACATTAATAGCTATTTAAGCTGTT
CCAGCAGAAACCAGGGAAATCTCCTAAGACCCTGATCTAT**CGTGCAGACAGAT
TGTTAGAT**GGGGTCCCATCAAGGTTCAGTGGCAGTGGATCTGGGCAAGATTATT
CTCTCACCATCAGCAGCCTGGAGTATGGAGATATGGGAATTTATTATTGT**CTAC
AGTATGATGAGTTTCCGTACACG**TTCGGAGGGGGGACCAAGCTGGAAATAAA
A mAb123-556F6B8-VH SEQ ID NO: 9
RVQLKQSGPGLVQPSQSLSITCTVSGFSLIKYGVHWVRQSPGEGLEWLGV**IWRGGITDYNA
AFMSRLSITKDNSKSQVFFKMNSLQADDTAIYYCAKWDGPLAMDY**WGQGTSVTVSS mAb123-556F6B8-VH SEQ ID NO: 51
CGGGTGCAGCTGAAGCAGTCAGGACCTGGCCTAGTGCAGCCCTCACAGAGCCT
GTCCATAACCTGCACAGTCTCTGGTTTCTCATTAATTAAGTACGGTGTACACTG
GGTTCGCCAGTCTCCAGGAGAGGGTCTGGAGTGGCTGGGA**GTGATATGGAGAG
GTGGCATCACAGACTACAATGCAGCTTTCATGTCC**AGACTGAGCATCACCAA
GGACAACTCCAAGAGCCAAGTTTTCTTTAAAATGAACAGTCTGCAAGCTGATGA
CACTGCCATATACTACTGTGCCAAATGGGACGGGCCCCTGGCTATGGACTAC
TGGGGTCAAGGAACCTCAGTCACCGTCTCCTCA mAb123-556F6B8-VL SEQ ID NO: 13
DIVMTQSHKFLSTSVGDRVSITCKASQDVGTTVAWYQQKPGQSPKLLIYWASTRHTGVPDR
FTGSGSGTDFTLTISNVQSEDLADYFCQQYSSYPYTFGGGTKLEIK mAb123-556F6B8-VL SEQ ID NO: 52
GACATTGTGATGACCCAGTCTCACAAATTCTTGTCCACATCAGTAGGAGACAGG
GTCAGCATCACCTGCAAGGCCAGTCAGGATGTGGGTACTACTGTAGCCTGGT
ATCAACAGAAACCAGGACAATCTCCTAAACTACTGATTTAC**TGGGCATCCACC
CGGCACACT**GGAGTCCCTGATCGCTTCACAGGCAGTGGATCTGGGACAGATTT
CACTCTCACCATTAGCAATGTGCAGTCTGAAGACTTGGCAGATTATTTCTGT**CA
GCAATATAGCAGCTATCCGTACACG**TTCGGAGGGGGGACCAAGCTAGAAATA
AAA mAb009-105F1E10-VH SEQ ID NO: 17
EVQLQQSGPELVKPGASVKMSCRASGYTFTDFKMHWMKQSHGKSLEWIG**YIAPNNGGTAYN
QKFRGKATLTVNESSNTAYMELRSLTSEDSAVYYCVDWDDVDY**WGQGTTLTVSS mAb009-105F1E10-VH SEQ ID NO: 53
GAGGTCCAGCTGCAACAGTCTGGACCTGAGCTGGTGAAGCCTGGGGCTTCAGTG
AAGATGTCCTGCAGGGCTTCTGGATACACATTCACTGACTTCAAAATGCACTG
GATGAAGCAGAGCCATGGAAAGAGCCTTGAGTGGATTGGA**TATATTGCCCCTA
ACAATGGTGGTACTGCCTACAATCAGAAATTCAGGGGC**AAGGCCACATTGA
CTGTAAACGAGTCCTCCAACACAGCCTACATGGAGCTCCGCAGCCTGACATCGG
AAGATTCTGCAGTCTATTACTGTGTGGACTGGGACGACGTTGACTACTGGGGC
CAAGGCACCACTCTCACAGTCTCCTCA mAb009-105F1E10-VL SEQ ID NO: 21
DIKMTQSPSSMYASLGERVTITCKASQDINSYLSWFQQKSGKSPKTLIYRANRLVDGVPSR
FSGSGSGQDYSLTISSLEYEDMGIYYCLQYVEFPLTFGAGTKLELK mAb009-105F1E10-VL SEQ ID NO: 54
GACATCAAGATGACCCAGTCTCCATCTTCCATGTATGCATCTCTAGGAGAGAGA
GTCACTATCACTTGCAAGGCGAGTCAGGACATTAATAGCTATTTAAGCTGTT
CCAGCAGAAATCAGGGAAATCTCCTAAGACCCTGATCTAT**CGTGCAAATAGAT
TGGTAGAT**GGGGTCCCATCAAGGTTCAGTGGCAGTGGATCTGGGCAAGATTAT
TCTCTCACCATCAGCAGCCTGGAGTATGAAGATATGGGAATTTATTATTGT**CTA
CAGTATGTTGAGTTTCCTCTCACG**TTCGGTGCTGGGACCAAGCTGGAGCTGAA
A mAb104-409B11E12-VH SEQ ID NO: 25
QVQLQQSGAELVRPGASVTLSCKASGYTFTDYEMHWVKQTTVHGLEWIG**ATDPETSYSAYN
QKFKGKAILTADKSSSTAYMELRSLTSEDSAVYYCIATGWND**WGQGTSLTVSS mAb104-409B11E12-VH SEQ ID NO: 55
CAGGTTCAACTGCAGCAGTCTGGGGCTGAGCTGGTGAGGCCTGGGGCTTCAGTG
ACGCTGTCCTGCAAGGCTTCGGGCTACACATTTACTGACTATGAAATGCACTG
GGTGAAGCAGAACTGTGCATGGCCTGGAATGGATTGGA**GCCACTGATCCTG
AAACTAGTTATAGTGCCTACAATCAGAAGTTCAAGGGC**AAGGCCATACTGAC
TGCAGACAAATCCTCCAGCACAGCCTACATGGAGCTCCGCAGCCTGACATCTGA
GGACTCTGCCGTCTATTACTGTATAGCAACTGGGTGGAACGACTGGGGCCAAG
GCACCAGTCTCACAGTCTCCTCA mAb104-409B11E12-VL SEQ ID NO: 29
DLKMTQSPSSMYASLGERVTITCKASQDINSYLSWFQQKPGKSPKTLIYRANRLLDGVPSR
FSGSGSGQDYSLTISSLEYEDMGIYYCLQYDEFPYTFGGGTKLEIK mAb104-409B11E12-VL SEQ ID NO: 56
GACCTCAAGATGACCCAGTCTCCATCTTCCATGTATGCATCTCTAGGAGAGAGA
GTCACTATCACTTGCAAGGCGAGTCAGGACATTAATAGCTATTTAAGTTGGTT
CCAGCAGAAACCAGGGAAATCTCCTAAGACCCTGATCTAT**CGTGCAAACAGAT
TGTTAGAT**GGGGTCCCATCAAGGTTCAGTGGCAGTGGATCTGGGCAAGATTATT
CTCTCACCATCAGCAGCCTGGAGTATGAAGATATGGGAATTTATTATTGT**CTAC
AGTATGATGAGTTTCCGTACACA**TTCGGAGGGGGGACCAAGCTGGAAATAAA
A mAb112-409D4E10-VH SEQ ID NO: 33
QVQLQQSGAELVRPGASVTLSCKASGNTFTDYEMHWVKQTPVHGLEWIG**ATDPETDNTAYN
QKFKGKAILTTDKSSSTAYMELRSLTSEDSAVYYCITSGWND**WGQGTSLTVSS mAb112-409D4E10-VH SEQ ID NO: 57
CAGGTTCAACTGCAGCAGTCTGGGGCTGAGCTGGTGAGGCCTGGGGCTTCAGTG
ACGCTGTCCTGCAAGGCTTCGGGCAACACATTTACTGACTATGAAATGCACTG
GGTGAAGCAGACACCTGTGCATGGCCTGGAATGGATTGGA**GCCACTGATCCTG
AAACTGATAATACTGCCTACAATCAGAAGTTCAAGGGC**AAGGCCATACTGAC
TACAGACAAATCCTCCAGCACAGCCTACATGGAGCTCCGCAGCCTGACATCTGA
GGACTCTGCCGTCTATTATTGCATAACAAGTGGGTGGAACGACTGGGGCCAAG
GCACCAGTCTCACAGTCTCCTCA mAb112-409D4E10-VL SEQ ID NO: 37
DIKMTQSPSSMYASLGERVTITCKASQDINSYLSWFQQKPGKSPKTLTYRANRLLDGVPSR
FSGSGSGQDYSLTISSLEYEDMGIYYCLQYNEFPYTFGGGTKLEIK mAb112-409D4E10-VL SEQ ID NO: 58
GACATCAAGATGACCCAGTCTCCATCTTCCATGTATGCATCTCTAGGAGAGAGA
GTCACTATCACTTGCAAGGCGAGTCAGGACATTAATAGCTATTTAAGCTGGTT
CCAGCAGAAACCAGGGAAATCTCCTAAGACCCTGATCTAT**CGTGCAAACAGAT
TGTTAGAT**GGGGTCCCATCAAGGTTCAGTGGCAGTGGATCTGGGCAAGATTATT
CTCTCACCATCAGCAGCCTGGAATATGAAGATATGGGAATTTATTATTGT**CTAC
AGTATAATGAGTTTCCGTACACG**TTCGGAGGGGGGACCAAGCTGGAAATAAA
A mAb120-553G8G8-VH SEQ ID NO: 41
RVQLKQSGPGLVQPSQSLSITCTVSGFSLIKYGVHWVRQSPGEGLEWLG**VIWRGGITDYNA
AFMSRLSITKDNSKSQVFFKMNSLQADDTAIYYCAKWDGPLAMDY**WGQGTSVTVSS mAb120-553G8G8-VH SEQ ID NO: 59
CGGGTGCAGCTGAAGCAGTCAGGACCTGGCCTAGTGCAGCCCTCACAGAGCCT
GTCCATAACCTGCACAGTCTCTGGTTTCTCATTAATTAAGTACGGTGTACACTG
GGTTCGCCAGTCTCCAGGAGAGGGTCTGGAGTGGCTGGGA**GTGATATGGAGAG
GTGGCATCACAGACTACAATGCAGCTTTCATGTCC**AGACTGAGCATCACCAA
GGACAACTCCAAGAGCCAAGTTTTCTTTAAAATGAACAGTCTGCAAGCTGATGA
CACTGCCATATACTACTGTGCCAAA**TGGGACGGGCCCCTGGCTATGGACTAC
TGGGGTCAAGGAACCTCAGTCACCGTCTCCTCA mAb120-553G8G8-VL SEQ ID NO: 45
DVQMIQSPSSLSASLGDMVTMTCQASQGTNINLNWFQQKPGKAPKLLIYGASNLEDGVPSR
FSGSRYGTDFTLTISSLEDEDMATYFGLQHSYLPLTFGAGTKLELK mAb120-553G8G8-VL SEQ ID NO: 60
GATGTCCAGATGATTCAGTCTCCATCCTCCCTGTCTGCATCTTTGGGAGACATGG
TCACCATGACTTGCCAGGCAAGTCAGGGCACTAACATTAATTTAAACTGGTTT
CAGCAAAAACCAGGGAAAGCTCCTAAGCTCCTGATCTAT**GGTGCAAGCAACTT
GGAAGAT**GGGGTCCCATCAAGGTTCAGTGGCAGTAGATATGGGACAGATTTCA
CTCTCACCATCAGCAGCCTGGAGGATGAAGATATGGCAACGTATTTCGGT**CTAC
AGCATAGTTATCTCCCGCTCACG**TTCGGTGCTGGGACCAAGCTGGAGCTGAAA

405B8H3-1-VH SEQ ID NO: 64
QVQLVQSGAEVKKPGASVKVSCKASGYTFTDYEMHWVRQAPGQGLEWMG**ATDP
ETGNSAYNQKFKGRVTMTRDTSTSTVYMELSSLRSEDTAVYYCISTGWND**WGQG
TTVTVSS

-continued

405B8H3-1-VH SEQ ID NO: 65
CAGGTGCAGCTGGTGCAGAGCGGCGCTGAAGTGAAGAAGCCCGGCGCCAGCGT
GAAGGTGAGCTGCAAGGCCAGCGGCTACACCTTCACCGACTACGAGATGCACT
GGGTGAGACAGGCTCCTGGCCAGGGCCTGGAGTGGATGGGA**GCCACCGATCC
CGAGACCGGCAACAGCGCCTATAACCAGAAGTTCAAGGGC**AGGGTGACCAT
GACCAGGGACACCAGCACCAGCACCGTGTACATGGAGCTGAGCAGCCTGAGGA
GCGAGGACACCGCCGTGTACTACTGCATCAGCACCGGCTGGAACGACTGGGG
ACAGGGCACCACCGTGACCGTGAGCAGC

405B8H3-1-VL SEQ ID NO: 76
DIQMTQSPSSLSASVGDRVTITCKASQDINSYLSWFQQKPGKAPKSLIYRADRLLD
GVPSRFSGSGSGTDFTLTISSLQPEDFATYYCLQYDEFPYTFGQGTKLEIK

405B8H3-1-VL SEQ ID NO: 77
GACATCCAGATGACCCAGAGCCCTAGCAGCCTGAGCGCTAGCGTGGGCGACAG
AGTGACCATCACCTGCAAGGCCAGCCAGGACATCAACAGCTACCTGAGCTGG
TTCCAGCAGAAGCCCGGCAAGGCCCCTAAGAGCCTGATCTAC**AGGGCCGACAG
ACTGCTGGAC**GGCGTGCCTAGCAGGTTTAGCGGCAGCGGCAGCGGCACCGATT
TCACCCTGACCATCAGCAGCCTGCAGCCCGAGGACTTCGCCACCTACTACTGC**C
TGCAGTACGACGAGTTCCCCTACACC**TTCGGCCAGGGCACCAAGCTGGAGAT
CAAG

405B8H3-2-VH SEQ ID NO: 66
QVQLVQSGAEVKKPGASVKVSCKASGYTFTDYEMHWVRQAPGQGLEWMG**ATDP
ETGNSAYNQKFKGRVTMTADKSTSTVYMELSSLRSEDTAVYYCISTGWND**WGQ
GTTVTVSS

405B8H3-2-VH SEQ ID NO: 67
CAGGTGCAGCTGGTGCAGAGCGGCGCTGAAGTGAAGAAGCCCGGCGCCAGCGT
GAAGGTGAGCTGCAAGGCCAGCGGCTACACCTTCACCGACTACGAGATGCACT
GGGTGAGACAGGCTCCTGGCCAGGGCCTGGAGTGGATGGGA**GCCACCGATCC
CGAGACCGGCAACAGCGCCTATAACCAGAAGTTCAAGGGC**AGGGTGACCAT
GACCGCCGACAAGAGCACCAGCACCGTGTACATGGAGCTGAGCAGCCTGAGGA
GCGAGGACACCGCCGTGTACTACTGCATCAGCACCGGCTGGAACGACTGGGG
ACAGGGCACCACCGTGACCGTGAGCAGC

405B8H3-2-VL amino acid sequence SEQ ID NO: 76

405B8H3-2-VL nucleotide sequence SEQ ID NO: 77

405B8H3-6-VH amino acid sequence SEQ ID NO: 66

405B8H3-6-VH nucleotide sequence SEQ ID NO: 67

405B8H3-6-VL SEQ ID NO: 78
DIQMTQSPSSLSASVGDRVTITCKASQDINSYLSWFQQKPGKAPKSLIYRADRLLD
GVPSRFSGSGSGQDYTLTISSLQPEDFATYYCLQYDEFPYTFGQGTKLEIK

405B8H3-6-VL SEQ ID NO: 79
GACATCCAGATGACCCAGAGCCCTAGCAGCCTGAGCGCTAGCGTGGGCGACAG
AGTGACCATCACCTGCAAGGCCAGCCAGGACATCAACAGCTACCTGAGCTGG
TTCCAGCAGAAGCCCGGCAAGGCCCCTAAGAGCCTGATCTAC**AGGGCCGACAG
ACTGCTGGAC**GGCGTGCCTAGCAGGTTTAGCGGCAGCGGCAGCGGCCAGGATT
ACACCCTGACCATCAGCAGCCTGCAGCCCGAGGACTTCGCCACCTACTACTGC**C
TGCAGTACGACGAGTTCCCCTACACC**TTCGGCCAGGGCACCAAGCTGGAGAT
CAAG

405B8H3-7-VH SEQ ID NO: 68
QVQLVQSGAEVKKPGASVKVSCKASGYTFTDYEMHWVRQAPGQGLEWIG**ATDPE
TGNSAYNQKFKGRATMTADKSTSTAYMELSSLRSEDTAVYYCISTGWND**WGQGT
TVTVSS

405B8H3-7-VH SEQ ID NO: 69
CAGGTGCAGCTGGTGCAGAGCGGCGCTGAAGTGAAGAAGCCTGGCGCCAGCGT
GAAGGTGTCCTGCAAGGCCAGCGGCTACACCTTCACCGACTACGAGATGCACT
GGGTGAGGCAGGCTCCTGGACAGGGCCTGGAGTGGATTGGC**GCCACAGACCCC
GAGACCGGCAATAGCGCCTACAACCAGAAGTTCAAGGGC**AGGGCCACAATG
ACCGCCGACAAGAGCACCAGCACCGCCTACATGGAGCTGAGCAGCCTGAGGAG
CGAGGACACCGCCGTGTACTACTGCATCTCCACCGGCTGGAACGACTGGGGAC
AGGGCACCACCGTGACCGTGAGCAGC

405B8H3-7-VL amino acid sequence SEQ ID NO: 78

405B8H3-7-VL nucleotide sequence SEQ ID NO: 79

405B8H3-1 (D→E)-VH amino acid sequence SEQ ID NO: 64

405B8H3-1 (D→E)-VH nucleotide sequence SEQ ID NO: 65

-continued

405B8H3-1(D→E)-VL SEQ ID NO: 74
DIQMTQSPSSLSASVGDRVTITCKASQDINSYLSWFQQKPGKAPKSLIYRADRLLE
GVPSRFSGSGSGTDFTLTISSLQPEDFATYYCLQYDEFPYTFGQGTKLEIK

405B8H3-1(D→E)-VL SEQ ID NO: 75
GACATCCAGATGACCCAGAGCCCTAGCAGCCTGAGCGCTAGCGTGGGCGACAG
AGTGACCATCACCTGCAAGGCCAGCCAGGACATCAACAGCTACCTGAGCTGG
TTCCAGCAGAAGCCCGGCAAGGCCCCTAAGAGCCTGATCTACAGGGCCGACAG
ACTGCTGGAAGGCGTGCCTAGCAGGTTTAGCGGCAGCGGCAGCGGCACCGATT
TCACCCTGACCATCAGCAGCCTGCAGCCCGAGGACTTCGCCACCTACTACTGCC
TGCAGTACGACGAGTTCCCCTACACCTTCGGCCAGGGCACCAAGCTGGAGAT
CAAG

556F6B8-3-VH SEQ ID NO: 72
QVQLQESGPGLVKPSETLSLTCTVSGFSLIKYGVHWIRQPPGKGLEWIGVIWRGGI
TDYNAAFMSRVTISKDTSKSQVSLKLSSVTAADTAVYYCARWDGPLAMDYWGQ
GTTVTVSS

556F6B8-3-VH SEQ ID NO: 73
CAGGTGCAGCTGCAGGAGTCCGGACCTGGCCTGGTGAAGCCCAGCGAGACCCT
GAGCCTGACCTGCACCGTGAGCGGCTTCAGCCTGATCAAGTACGGCGTGCACT
GGATCAGGCAGCCTCCCGGAAAGGGCTGGAGTGGATCGGCGTCATCTGGAG
GGGCGGCATCACCGACTACAACGCCGCCTTCATGAGCAGGGTGACCATCAG
CAAGGACACCAGCAAGAGCCAGGTGAGCCTGAAGCTGAGCAGCGTGACAGCCG
CCGACACAGCCGTGTACTACTGTGCCAGGTGGGATGGCCCCCTGGCCATGGA
TTACTGGGGCCAGGGCACCACAGTGACCGTGAGCAGC

556F6B8-3-VL SEQ ID NO: 80
DIQLTQSPSFLSASVGDRVTITCKASQDVGTTVAWYQQKPGKAPKLLIYWASTRH
TGVPSRFSGSGSGTEFTLTISSLQPEDFATYYCQQYSSYPYTFGQGTKLEIK

556F6B8-3-VL SEQ ID NO: 81
GACATCCAGCTGACCCAGAGCCCCAGCTTTCTGAGCGCCAGCGTGGGCGACAG
GGTGACCATCACCTGCAAGGCCAGCCAGGACGTGGGCACCACAGTGGCCTG
GTACCAGCAGAAGCCCGGCAAGGCCCCCAAGCTGCTGATCTACTGGGCCAGCA
CCAGGCATACAGGCGTGCCCAGCAGATTCAGCGGCAGCGGAAGCGGCACCGA
GTTCACCCTGACCATCAGCAGCCTGCAGCCCGAGGACTTCGCCACCTACTACTG
CCAGCAGTACAGCTCCTACCCCTACACCTTCGGCCAGGGCACCAAGCTGGAG
ATCAAG

556F6B8-7-VH amino acid sequence SEQ ID NO: 72

556F6B8-7-VH nucleotide sequence SEQ ID NO: 73

556F6B8-7-VL SEQ ID NO: 82
DIVLTQSPSFLSASVGDRVTITCKASQDVGTTVAWYQQKPGKAPKLLIYWASTRH
TGVPSRFSGSGSGTEFTLTISSLQPEDFATYYCQQYSSYPYTFGQGTKLEIK

556F6B8-7-VL SEQ ID NO: 83
GACATCGTGCTGACCCAGAGCCCCAGCTTTCTGAGCGCCAGCGTGGGCGACAGG
GTGACCATCACCTGCAAGGCCAGCCAGGACGTGGGCACCACAGTGGCCTGG
TACCAGCAGAAGCCCGGCAAGGCCCCCAAGCTGCTGATCTACTGGGCCAGCAC
CAGGCATACAGGCGTGCCCAGCAGATTCAGCGGCAGCGGAAGCGGCACCGAGT
TCACCCTGACCATCAGCAGCCTGCAGCCCGAGGACTTCGCCACCTACTACTGCC
AGCAGTACAGCTCCTACCCCTACACCTTCGGCCAGGGCACCAAGCTGGAGAT
CAAG

556F6B8-3(D→E)-VH SEQ ID NO: 70
QVQLQESGPGLVKPSETLSLTCTVSGFSLIKYGVHWIRQPPGKGLEWIGVIWRGGI
TDYNAAFMSRVTISKDTSKSQVSLKLSSVTAADTAVYYCARWEGPLAMDYWGQ
GTTVTVSS

556F6B8-3(D→E)-VH SEQ ID NO: 71
CAGGTGCAGCTGCAGGAGTCCGGACCTGGCCTGGTGAAGCCCAGCGAGACCCT
GAGCCTGACCTGCACCGTGAGCGGCTTCAGCCTGATCAAGTACGGCGTGCACT
GGATCAGGCAGCCTCCCGGAAAGGGCCTGGAGTGGATCGGCGTCATCTGGAG
GGGCGGCATCACCGACTACAACGCCGCCTTCATGAGCAGGGTGACCATCAG
CAAGGACACCAGCAAGAGCCAGGTGAGCCTGAAGCTGAGCAGCGTGACAGCCG
CCGACACAGCCGTGTACTACTGTGCCAGGTGGGAAGGCCCCCTGGCCATGGA
TTACTGGGGCCAGGGCACCACAGTGACCGTGAGCAGC

556F6B8-3(D→E)-VL amino acid sequence SEQ ID NO: 80

556F6B8-3(D→E)-VL nucleotide sequence SEQ ID NO: 81

TABLE 20

LAG3-antibody CDR region sequences and the amino acid sequence numbering (SEQ ID NO:) are as follows:

| Clone number | CDR | Amino acid sequence information | SEQ ID NO: |
|---|---|---|---|
| 405B8H3 | VH-CDR1 | DYEMH | 2 |
| | VH-CDR2 | ATDPETGNSAYNQKFKG | 3 |
| | VH-CDR3 | TGWND | 4 |
| | VL-CDR1 | KASQDINSYLS | 6 |
| | VL-CDR2 | RADRLLD | 7 |
| | VL-CDR3 | LQYDEFPYT | 8 |
| 556F6B8 | VH-CDR1 | KYGVH | 10 |
| | VH-CDR2 | VIWRGGITDYNAAFMS | 11 |
| | VH-CDR3 | WDGPLAMDY | 12 |
| | VL-CDR1 | KASQDVGTTVA | 14 |
| | VL-CDR2 | WASTRHT | 15 |
| | VL-CDR3 | QQYSSYPYT | 16 |
| 105F1E10 | VH-CDR1 | DFKMH | 18 |
| | VH-CDR2 | YIAPNNGGTAYNQKFRG | 19 |
| | VH-CDR3 | WDDVDY | 20 |
| | VL-CDR1 | KASQDINSYLS | 22 |
| | VL-CDR2 | RANRLVD | 23 |
| | VL-CDR3 | LQYVEFPLT | 24 |
| 409B11E12 | VH-CDR1 | DYEMH | 26 |
| | VH-CDR2 | ATDPETSYSAYNQKFKG | 27 |
| | VH-CDR3 | TGWND | 28 |
| | VL-CDR1 | KASQDINSYLS | 30 |
| | VL-CDR2 | RANRLLD | 31 |
| | VL-CDR3 | LQYDEFPYT | 32 |
| 409D4E10 | VH-CDR1 | DYEMH | 34 |
| | VH-CDR2 | ATDPETDNTAYNQKFKG | 35 |
| | VH-CDR3 | SGWND | 36 |
| | VL-CDR1 | KASQDINSYLS | 38 |
| | VL-CDR2 | RANRLLD | 39 |
| | VL-CDR3 | LQYNEFPYT | 40 |
| 553G8G8 | VH-CDR1 | KYGVH | 42 |
| | VH-CDR2 | VIWRGGITDYNAAFMS | 43 |
| | VH-CDR3 | WDGPLAMDY | 44 |
| | VL-CDR1 | QASQGTNINLN | 46 |
| | VL-CDR2 | GASNLED | 47 |
| | VL-CDR3 | LQHSYLPLT | 48 |
| 405B8H3-1 (D→E) | VH-CDR1 | DYEMH | 2 |
| | VH-CDR2 | ATDPETGNSAYNQKFKG | 3 |
| | VH-CDR3 | TGWND | 4 |
| | VL-CDR1 | KASQDINSYLS | 6 |
| | VL-CDR2 | RADRLLE | 84 |
| | VL-CDR3 | LQYDEFPYT | 8 |
| 405B8H3-1 | VH-CDR1 | DYEMH | 2 |
| | VH-CDR2 | ATDPETGNSAYNQKFKG | 3 |
| | VH-CDR3 | TGWND | 4 |
| | VL-CDR1 | KASQDINSYLS | 6 |
| | VL-CDR2 | RADRLLD | 7 |
| | VL-CDR3 | LQYDEFPYT | 8 |
| 405B8H3-2 | VH-CDR1 | DYEMH | 2 |
| | VH-CDR2 | ATDPETGNSAYNQKFKG | 3 |
| | VH-CDR3 | TGWND | 4 |
| | VL-CDR1 | KASQDINSYLS | 6 |
| | VL-CDR2 | RADRLLD | 7 |
| | VL-CDR3 | LQYDEFPYT | 8 |
| 405B8H3-6 | VH-CDR1 | DYEMH | 2 |
| | VH-CDR2 | ATDPETGNSAYNQKFKG | 3 |
| | VH-CDR3 | TGWND | 4 |
| | VL-CDR1 | KASQDINSYLS | 6 |
| | VL-CDR2 | RADRLLD | 7 |
| | VL-CDR3 | LQYDEFPYT | 8 |
| 405B8H3-7 | VH-CDR1 | DYEMH | 2 |
| | VH-CDR2 | ATDPETGNSAYNQKFKG | 3 |
| | VH-CDR3 | TGWND | 4 |
| | VL-CDR1 | KASQDINSYLS | 6 |
| | VL-CDR2 | RADRLLD | 7 |
| | VL-CDR3 | LQYDEFPYT | 8 |
| 556F6B8-3 (D→E) | VH-CDR1 | KYGVH | 10 |
| | VH-CDR2 | VIWRGGITDYNAAFMS | 11 |
| | VH-CDR3 | WEGPLAMDY | 85 |
| | VL-CDR1 | KASQDVGTTVA | 14 |
| | VL-CDR2 | WASTRHT | 15 |
| | VL-CDR3 | QQYSSYPYT | 16 |
| 556F6B8-3 | VH-CDR1 | KYGVH | 10 |
| | VH-CDR2 | VIWRGGITDYNAAFMS | 11 |
| | VH-CDR3 | WDGPLAMDY | 12 |
| | VL-CDR1 | KASQDVGTTVA | 14 |
| | VL-CDR2 | WASTRHT | 15 |
| | VL-CDR3 | QQYSSYPYT | 16 |
| 556F6B8-7 | VH-CDR1 | KYGVH | 10 |
| | VH-CDR2 | VIWRGGITDYNAAFMS | 11 |
| | VH-CDR3 | WDGPLAMDY | 12 |
| | VL-CDR1 | KASQDVGTTVA | 14 |
| | VL-CDR2 | WASTRHT | 15 |
| | VL-CDR3 | QQYSSYPYT | 16 |

Wherein, VH is the variable region of the heavy chain, and VL is the variable region of the light chain. VH-CDR1, VH-CDR2, VH-CDR3 are heavy chain variable region CDR1, CDR2, CDR3, respectively; VL-CDR1, VL-CDR2, VL-CDR3 are light chain variable region CDR1', CDR2', CDR3', respectively.

TABLE 33

Summary of humanized VH or VL

| Humanized VH or VL | amino acid sequence SEQ ID NO: | nucleotide sequence SEQ ID NO: |
|---|---|---|
| Humanized VH1 | 64 | 65 |
| Humanized VH2 | 66 | 67 |
| Humanized VH3 | 68 | 69 |
| Humanized VH4 | 70 | 71 |
| Humanized VH5 | 72 | 73 |
| Humanized VL1 | 74 | 75 |
| Humanized VL2 | 76 | 77 |
| Humanized VL3 | 78 | 79 |
| Humanized VL4 | 80 | 81 |
| Humanized VL5 | 82 | 83 |

TABLE 34

Summary of antibody VH and VL

| | VH SEQ ID NO: | VL SEQ ID NO: |
|---|---|---|
| 405B8H3 | 1 | 5 |
| 556F6B8 | 9 | 13 |
| 105F1E10 | 17 | 21 |
| 409B11E12 | 25 | 29 |
| 409D4E10 | 33 | 37 |
| 553G8G8 | 41 | 45 |
| 405B8H3-1 (D→E) | 64 | 74 |
| 405B8H3-1 | 64 | 76 |
| 405B8H3-2 | 66 | 76 |

TABLE 34-continued

Summary of antibody VH and VL

| | VH SEQ ID NO: | VL SEQ ID NO: |
|---|---|---|
| 405B8H3-6 | 66 | 78 |
| 405B8H3-7 | 68 | 78 |
| 556F6B8-3 (D→E) | 70 | 80 |
| 556F6B8-3 | 72 | 80 |
| 556F6B8-7 | 72 | 82 |

Amino acid sequence of human LAG-3 protein
SEQ ID NO: 61
MWEAQFLGLLFLQPLWVAPVKPLQPGAEVPVVWAQEGAPAQLPCSPTIP
LQDLSLLRRAGVTWQHQPDSGPPAAAPGHPLAPGPHPAAPSSWGPRPRR
YTVLSVGPGGLRSGRLPLQPRVQLDERGRQRGDFSLWLRPARRADAGEY
RAAVHLRDRALSCRLRLRGQASMTASPPGSLRASDWVILNCSFSRPDR
PASVHWFRNRGQGRVPVRESPHHHLAESFLFLPQVSPMDSGPWGCILTY
RDGFNVSIMYNLTVLGLEPPTPLTVYAGAGSRVGLPCRLPAGVGTRSFL
TAKWTPPGGGPDLLVTGDNGDFTLRLEDVSQAQAGTYTCHIHLQEQQLN
ATVTLAIITVTPKSFGSPGSLGKLLCEVTPVSGQERFVWSSLDTPSQRS
FSGPWLEAQEAQLLSQPWQCQLYQGERLLGAAVYFTELSSPGAQRSGRA
PGALPAGHLLLFLILGVLSLLLLVTGAFGFHLWRRQWRPRRFSALEQGI
HPPQAQSKIEELEQEPEPEPEPEPEPEPEPEPEQL Amino acid sequence of monkey LAG-3 protein
SEQ ID NO: 62
MWEAQFLGLLFLQPLWVAPVKPPQPGAEISVVWAQEGAPAQLPCSPTIP
LQDLSLLRRAGVTWQHQPDSGPPAPAPGHPPAPGHRPAAPYSWGPRPRR
YTVLSVGPGGLRSGRLPLQPRVQLDERGRQRGDFSLWLRPARRADAGEY
RATVHLRDRALSCRLRLRVGQASMTASPPGSLRTSDWVILNCSFSRPDR
PASVHWFRSRGQGRVPVQGSPHHHLAESFLFLPHVGPMDSGLWGCILTY
RDGFNVSIMYNLTVLGLEPATPLTVYAGAGSRVELPCRLPPAVGTQSFL
TAKWAPPGGGPDLLVAGDNGDFTLRLEDVSQAQAGTYICHIRLQGQQLN
ATVTLAIITVTPKSFGSPGSLGKLLCEVTPASGQEHFVWSPLNTPSQRS
FSGPWLEAQEAQLLSQPWQCQLHQGERLLGAAVYFTELSSPGAQRSGRA
PGALRAGHLPLFLILGVLFLLLLVTGAFGFHLWRRQWRPRRFSALEQGI
HPPQAQSKIEELEQEPELEPEPELERELGPEPEPGPEPEPEQL*

Amino acid sequence of mouse LAG-3 protein
SEQ ID NO: 63
MREDLLLGFLLLGLLWEAPVVSSGPGKELPVVWAQEGAPVHLPCSLKSP
NLDPNFLRRGGVIWQHQPDSGQPTPIPALDLHQGMPSPRQPAPGRYTVL
SVAPGGLRSGRQPLHPHVQLEERGLQRGDFSLWLRPALRTDAGEYHATV
RLPNRALSCSLRLRVGQASMIASPSGVLKLSDWVLLNCSFSRPDRPVSV
HWFQGQNRVPVYNSPRHFLAETFLLLPQVSPLDSGTWGCVLTYRDGFNV
SITYNLKVLGLEPVAPLTVYAAEGSRVELPCHLPPGVGTPSLLIAKWTP
PGGGPELPVAGKSGNFTLHLEAVGLAQAGTYTCSIHLQGQQLNATVTLA
VITVTPKSFGLPGSRGKLLCEVTPASGKERFVWRPLNNLSRSCPGPVLE
IQEARLLAERWQCQLYEGQRLLGATVYAAESSSGAHSARRISGDLKGGH
LVLVLILGALSLFLLVAGAFGFHWWRKQLLLRRFSALEHGIQPFPAQRK
IEELERELETEMGQEPEPEPEPQLEPEPRQL

---

The invention claimed is:

1. An antibody, that binds to LAG-3 comprising:
   (1) a heavy chain variable region comprising the following three complementary determining regions (CDRs):
   CDR1 having the amino acid sequence of SEQ ID NO: 2;
   CDR2 having the amino acid sequence of SEQ ID NO: 3; and
   CDR3 having the amino acid sequence of SEQ ID NO: 4; and
   (2) a light chain variable region comprising the following three complementary determining regions (CDRs):
   CDR1' having the amino acid sequence of SEQ ID NO: 6;
   CDR2' having the amino acid sequence of SEQ ID NO: 7 or SEQ ID NO: 84; and
   CDR3' having the amino acid sequence of SEQ ID NO: 8.

2. The antibody of claim 1, wherein the heavy chain variable region comprises the amino acid sequence of SEQ ID NO: 1, and wherein the light chain variable region comprises the amino acid sequence of SEQ ID NO: 5.

3. The antibody of claim 1, wherein
   the heavy chain variable region comprises the amino acid sequence of SEQ ID NO: 64, and wherein the light chain variable region comprises the amino acid sequence of SEQ ID NO: 74.

4. A recombinant protein comprising:
   (i) the antibody of claim 1; and
   (ii) an optional tag sequence that assists expression and/or purification of the recombinant protein.

5. A polynucleotide encoding the antibody of claim 1, or a recombinant protein comprising the antibody of claim 1.

6. The polynucleotide of claim 5, wherein the polynucleotide comprises the nucleotide sequence of SEQ ID NO: 49 (encoding the heavy chain variable region) and the nucleotide sequence of SEQ ID NO: 50 (encoding the light chain variable region); or
   wherein the polynucleotide comprises the nucleotide sequence of SEQ ID NO: 65 (encoding the heavy chain variable region) and the nucleotide sequence of SEQ ID NO: 77 (encoding the light chain variable region).

7. A vector comprising the polynucleotide of claim 5.

8. A genetically engineered host cell comprising the vector of claim 7.

9. A pharmaceutical composition comprising:
   (i) the antibody of claim 1 as an active ingredient; and
   (ii) a pharmaceutically acceptable carrier.

10. A composition for detecting LAG-3 protein in a sample in vitro, which comprises the antibody of claim 1 as an active ingredient.

11. A method for preparing a recombinant protein, wherein the method comprises:
    (a) culturing a host cell containing a vector comprising a polynucleotide encoding the antibody of claim 1 under conditions suitable for expression; and
    (b) isolating a recombinant protein from the culture, wherein the recombinant protein is the antibody of claim 5.

* * * * *

SEQUENCE LISTING

<160> NUMBER OF SEQ ID NOS: 110

<210> SEQ ID NO 1
<211> LENGTH: 114
<212> TYPE: PRT
<213> ORGANISM: Artificial Sequence
<220> FEATURE:
<223> OTHER INFORMATION: 405B8H3-VH

<400> SEQUENCE: 1

Gln Val Gln Leu Gln Gln Ser Gly Ala Glu Leu Val Arg Pro Gly Ala
1               5                   10                  15

Ser Val Thr Leu Ser Cys Lys Ala Ser Gly Tyr Thr Phe Thr Asp Tyr
                20                  25                  30

Glu Met His Trp Val Lys Gln Thr Pro Val His Gly Leu Glu Trp Ile
            35                  40                  45

Gly Ala Thr Asp Pro Glu Thr Gly Asn Ser Ala Tyr Asn Gln Lys Phe
        50                  55                  60

Lys Gly Lys Ala Ile Met Thr Ala Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

```
Ile Ser Thr Gly Trp Asn Asp Trp Gly Gln Gly Thr Ser Leu Thr Val
            100                 105                 110

Ser Ser

<210> SEQ ID NO 2
<211> LENGTH: 5
<212> TYPE: PRT
<213> ORGANISM: Artificial Sequence
<220> FEATURE:
<223> OTHER INFORMATION: VH-CDR

<400> SEQUENCE: 2

Asp Tyr Glu Met His
1               5

<210> SEQ ID NO 3
<211> LENGTH: 17
<212> TYPE: PRT
<213> ORGANISM: Artificial Sequence
<220> FEATURE:
<223> OTHER INFORMATION: VH-CDR

<400> SEQUENCE: 3

Ala Thr Asp Pro Glu Thr Gly Asn Ser Ala Tyr Asn Gln Lys Phe Lys
1               5                   10                  15

Gly

<210> SEQ ID NO 4
<211> LENGTH: 5
<212> TYPE: PRT
<213> ORGANISM: Artificial Sequence
<220> FEATURE:
<223> OTHER INFORMATION: VH-CDR

<400> SEQUENCE: 4

Thr Gly Trp Asn Asp
1               5

<210> SEQ ID NO 5
<211> LENGTH: 107
<212> TYPE: PRT
<213> ORGANISM: Artificial Sequence
<220> FEATURE:
<223> OTHER INFORMATION: 405B8H3-VL

<400> SEQUENCE: 5

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asp Arg Leu Leu Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Gly Asp Met Gly Ile Tyr Tyr Cys Leu Gln Tyr Asp Glu Phe Pro Tyr
                85                  90                  95

Thr Phe Gly Gly Gly Thr Lys Leu Glu Ile Lys
            100                 105
```

```
<210> SEQ ID NO 6
<211> LENGTH: 11
<212> TYPE: PRT
<213> ORGANISM: Artificial Sequence
<220> FEATURE:
<223> OTHER INFORMATION: VL-CDR

<400> SEQUENCE: 6

Lys Ala Ser Gln Asp Ile Asn Ser Tyr Leu Ser
1               5                   10

<210> SEQ ID NO 7
<211> LENGTH: 7
<212> TYPE: PRT
<213> ORGANISM: Artificial Sequence
<220> FEATURE:
<223> OTHER INFORMATION: VL-CDR

<400> SEQUENCE: 7

Arg Ala Asp Arg Leu Leu Asp
1               5

<210> SEQ ID NO 8
<211> LENGTH: 9
<212> TYPE: PRT
<213> ORGANISM: Artificial Sequence
<220> FEATURE:
<223> OTHER INFORMATION: VL-CDR

<400> SEQUENCE: 8

Leu Gln Tyr Asp Glu Phe Pro Tyr Thr
1               5

<210> SEQ ID NO 9
<211> LENGTH: 117
<212> TYPE: PRT
<213> ORGANISM: Artificial Sequence
<220> FEATURE:
<223> OTHER INFORMATION: 556F6B8-VH

<400> SEQUENCE: 9

Arg Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Ile Lys Tyr
            20                  25                  30

Gly Val His Trp Val Arg Gln Ser Pro Gly Glu Gly Leu Glu Trp Leu
        35                  40                  45

Gly Val Ile Trp Arg Gly Gly Ile Thr Asp Tyr Asn Ala Ala Phe Met
    50                  55                  60

Ser Arg Leu Ser Ile Thr Lys Asp Asn Ser Lys Ser Gln Val Phe Phe
65                  70                  75                  80

Lys Met Asn Ser Leu Gln Ala Asp Asp Thr Ala Ile Tyr Tyr Cys Ala
                85                  90                  95

Lys Trp Asp Gly Pro Leu Ala Met Asp Tyr Trp Gly Gln Gly Thr Ser
            100                 105                 110

Val Thr Val Ser Ser
        115

<210> SEQ ID NO 10
<211> LENGTH: 5
<212> TYPE: PRT
<213> ORGANISM: Artificial Sequence
<220> FEATURE:
<223> OTHER INFORMATION: VH-CDR
```

<400> SEQUENCE: 10

Lys Tyr Gly Val His
1               5

<210> SEQ ID NO 11
<211> LENGTH: 16
<212> TYPE: PRT
<213> ORGANISM: Artificial Sequence
<220> FEATURE:
<223> OTHER INFORMATION: VH-CDR

<400> SEQUENCE: 11

Val Ile Trp Arg Gly Gly Ile Thr Asp Tyr Asn Ala Ala Phe Met Ser
1               5                   10                  15

<210> SEQ ID NO 12
<211> LENGTH: 9
<212> TYPE: PRT
<213> ORGANISM: Artificial Sequence
<220> FEATURE:
<223> OTHER INFORMATION: VH-CDR

<400> SEQUENCE: 12

Trp Asp Gly Pro Leu Ala Met Asp Tyr
1               5

<210> SEQ ID NO 13
<211> LENGTH: 107
<212> TYPE: PRT
<213> ORGANISM: Artificial Sequence
<220> FEATURE:
<223> OTHER INFORMATION: 556F6B8-VL

<400> SEQUENCE: 13

Asp Ile Val Met Thr Gln Ser His Lys Phe Leu Ser Thr Ser Val Gly
1               5                   10                  15

Asp Arg Val Ser Ile Thr Cys Lys Ala Ser Gln Asp Val Gly Thr Thr
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Ser Tyr Pro Tyr
                85                  90                  95

Thr Phe Gly Gly Gly Thr Lys Leu Glu Ile Lys
            100                 105

<210> SEQ ID NO 14
<211> LENGTH: 11
<212> TYPE: PRT
<213> ORGANISM: Artificial Sequence
<220> FEATURE:
<223> OTHER INFORMATION: VL-CDR

<400> SEQUENCE: 14

Lys Ala Ser Gln Asp Val Gly Thr Thr Val Ala
1               5                   10

<210> SEQ ID NO 15
<211> LENGTH: 7

```
<212> TYPE: PRT
<213> ORGANISM: Artificial Sequence
<220> FEATURE:
<223> OTHER INFORMATION: VL-CDR

<400> SEQUENCE: 15

Trp Ala Ser Thr Arg His Thr
1               5

<210> SEQ ID NO 16
<211> LENGTH: 9
<212> TYPE: PRT
<213> ORGANISM: Artificial Sequence
<220> FEATURE:
<223> OTHER INFORMATION: VL-CDR

<400> SEQUENCE: 16

Gln Gln Tyr Ser Ser Tyr Pro Tyr Thr
1               5

<210> SEQ ID NO 17
<211> LENGTH: 115
<212> TYPE: PRT
<213> ORGANISM: Artificial Sequence
<220> FEATURE:
<223> OTHER INFORMATION: 105F1E10-VH

<400> SEQUENCE: 17

Glu Val Gln Leu Gln Gln Ser Gly Pro Glu Leu Val Lys Pro Gly Ala
1               5                   10                  15

Ser Val Lys Met Ser Cys Arg Ala Ser Gly Tyr Thr Phe Thr Asp Phe
            20                  25                  30

Lys Met His Trp Met Lys Gln Ser His Gly Lys Ser Leu Glu Trp Ile
        35                  40                  45

Gly Tyr Ile Ala Pro Asn Asn Gly Gly Thr Ala Tyr Asn Gln Lys Phe
    50                  55                  60

Arg Gly Lys Ala Thr Leu Thr Val Asn Glu Ser Ser Asn Thr Ala Tyr
65                  70                  75                  80

Met Glu Leu Arg Ser Leu Thr Ser Glu Asp Ser Ala Val Tyr Tyr Cys
                85                  90                  95

Val Asp Trp Asp Asp Val Asp Tyr Trp Gly Gln Gly Thr Thr Leu Thr
            100                 105                 110

Val Ser Ser
        115

<210> SEQ ID NO 18
<211> LENGTH: 5
<212> TYPE: PRT
<213> ORGANISM: Artificial Sequence
<220> FEATURE:
<223> OTHER INFORMATION: VH-CDR

<400> SEQUENCE: 18

Asp Phe Lys Met His
1               5

<210> SEQ ID NO 19
<211> LENGTH: 17
<212> TYPE: PRT
<213> ORGANISM: Artificial Sequence
<220> FEATURE:
<223> OTHER INFORMATION: VH-CDR
```

<400> SEQUENCE: 19

Tyr Ile Ala Pro Asn Asn Gly Gly Thr Ala Tyr Asn Gln Lys Phe Arg
1               5                   10                  15

Gly

<210> SEQ ID NO 20
<211> LENGTH: 6
<212> TYPE: PRT
<213> ORGANISM: Artificial Sequence
<220> FEATURE:
<223> OTHER INFORMATION: VH-CDR

<400> SEQUENCE: 20

Trp Asp Asp Val Asp Tyr
1               5

<210> SEQ ID NO 21
<211> LENGTH: 107
<212> TYPE: PRT
<213> ORGANISM: Artificial Sequence
<220> FEATURE:
<223> OTHER INFORMATION: 105F1E10-VL

<400> SEQUENCE: 21

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Ser Trp Phe Gln Gln Lys Ser Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Val Glu Phe Pro Leu
                85                  90                  95

Thr Phe Gly Ala Gly Thr Lys Leu Glu Leu Lys
            100                 105

<210> SEQ ID NO 22
<211> LENGTH: 11
<212> TYPE: PRT
<213> ORGANISM: Artificial Sequence
<220> FEATURE:
<223> OTHER INFORMATION: VL-CDR

<400> SEQUENCE: 22

Lys Ala Ser Gln Asp Ile Asn Ser Tyr Leu Ser
1               5                   10

<210> SEQ ID NO 23
<211> LENGTH: 7
<212> TYPE: PRT
<213> ORGANISM: Artificial Sequence
<220> FEATURE:
<223> OTHER INFORMATION: VL-CDR

<400> SEQUENCE: 23

Arg Ala Asn Arg Leu Val Asp
1               5

```
<210> SEQ ID NO 24
<211> LENGTH: 9
<212> TYPE: PRT
<213> ORGANISM: Artificial Sequence
<220> FEATURE:
<223> OTHER INFORMATION: VL-CDR

<400> SEQUENCE: 24

Leu Gln Tyr Val Glu Phe Pro Leu Thr
1               5

<210> SEQ ID NO 25
<211> LENGTH: 114
<212> TYPE: PRT
<213> ORGANISM: Artificial Sequence
<220> FEATURE:
<223> OTHER INFORMATION: 409B11E12-VH

<400> SEQUENCE: 25

Gln Val Gln Leu Gln Gln Ser Gly Ala Glu Leu Val Arg Pro Gly Ala
1               5                   10                  15

Ser Val Thr Leu Ser Cys Lys Ala Ser Gly Tyr Thr Phe Thr Asp Tyr
                20                  25                  30

Glu Met His Trp Val Lys Gln Thr Thr Val His Gly Leu Glu Trp Ile
            35                  40                  45

Gly Ala Thr Asp Pro Glu Thr Ser Tyr Ser Ala Tyr Asn Gln Lys Phe
        50                  55                  60

Lys Gly Lys Ala Ile Leu Thr Ala Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ile Ala Thr Gly Trp Asn Asp Trp Gly Gln Gly Thr Ser Leu Thr Val
            100                 105                 110

Ser Ser

<210> SEQ ID NO 26
<211> LENGTH: 5
<212> TYPE: PRT
<213> ORGANISM: Artificial Sequence
<220> FEATURE:
<223> OTHER INFORMATION: VH-CDR

<400> SEQUENCE: 26

Asp Tyr Glu Met His
1               5

<210> SEQ ID NO 27
<211> LENGTH: 17
<212> TYPE: PRT
<213> ORGANISM: Artificial Sequence
<220> FEATURE:
<223> OTHER INFORMATION: VH-CDR

<400> SEQUENCE: 27

Ala Thr Asp Pro Glu Thr Ser Tyr Ser Ala Tyr Asn Gln Lys Phe Lys
1               5                   10                  15

Gly

<210> SEQ ID NO 28
<211> LENGTH: 5
<212> TYPE: PRT
<213> ORGANISM: Artificial Sequence
<220> FEATURE:
```

<223> OTHER INFORMATION: VH-CDR

<400> SEQUENCE: 28

Thr Gly Trp Asn Asp
1               5

<210> SEQ ID NO 29
<211> LENGTH: 107
<212> TYPE: PRT
<213> ORGANISM: Artificial Sequence
<220> FEATURE:
<223> OTHER INFORMATION: 409B11E12-VL

<400> SEQUENCE: 29

Asp Leu Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Leu Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Tyr
                85                  90                  95

Thr Phe Gly Gly Gly Thr Lys Leu Glu Ile Lys
            100                 105

<210> SEQ ID NO 30
<211> LENGTH: 11
<212> TYPE: PRT
<213> ORGANISM: Artificial Sequence
<220> FEATURE:
<223> OTHER INFORMATION: VL-CDR

<400> SEQUENCE: 30

Lys Ala Ser Gln Asp Ile Asn Ser Tyr Leu Ser
1               5                   10

<210> SEQ ID NO 31
<211> LENGTH: 7
<212> TYPE: PRT
<213> ORGANISM: Artificial Sequence
<220> FEATURE:
<223> OTHER INFORMATION: VL-CDR

<400> SEQUENCE: 31

Arg Ala Asn Arg Leu Leu Asp
1               5

<210> SEQ ID NO 32
<211> LENGTH: 9
<212> TYPE: PRT
<213> ORGANISM: Artificial Sequence
<220> FEATURE:
<223> OTHER INFORMATION: VL-CDR

<400> SEQUENCE: 32

Leu Gln Tyr Asp Glu Phe Pro Tyr Thr
1               5

<210> SEQ ID NO 33

```
<211> LENGTH: 114
<212> TYPE: PRT
<213> ORGANISM: Artificial Sequence
<220> FEATURE:
<223> OTHER INFORMATION: 409D4E10-VH

<400> SEQUENCE: 33

Gln Val Gln Leu Gln Gln Ser Gly Ala Glu Leu Val Arg Pro Gly Ala
1               5                   10                  15

Ser Val Thr Leu Ser Cys Lys Ala Ser Gly Asn Thr Phe Thr Asp Tyr
            20                  25                  30

Glu Met His Trp Val Lys Gln Thr Pro Val His Gly Leu Glu Trp Ile
        35                  40                  45

Gly Ala Thr Asp Pro Glu Thr Asp Asn Thr Ala Tyr Asn Gln Lys Phe
    50                  55                  60

Lys Gly Lys Ala Ile Leu Thr Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ile Thr Ser Gly Trp Asn Asp Trp Gly Gln Gly Thr Ser Leu Thr Val
            100                 105                 110

Ser Ser

<210> SEQ ID NO 34
<211> LENGTH: 5
<212> TYPE: PRT
<213> ORGANISM: Artificial Sequence
<220> FEATURE:
<223> OTHER INFORMATION: VH-CDR

<400> SEQUENCE: 34

Asp Tyr Glu Met His
1               5

<210> SEQ ID NO 35
<211> LENGTH: 17
<212> TYPE: PRT
<213> ORGANISM: Artificial Sequence
<220> FEATURE:
<223> OTHER INFORMATION: VH-CDR

<400> SEQUENCE: 35

Ala Thr Asp Pro Glu Thr Asp Asn Thr Ala Tyr Asn Gln Lys Phe Lys
1               5                   10                  15

Gly

<210> SEQ ID NO 36
<211> LENGTH: 5
<212> TYPE: PRT
<213> ORGANISM: Artificial Sequence
<220> FEATURE:
<223> OTHER INFORMATION: VH-CDR

<400> SEQUENCE: 36

Ser Gly Trp Asn Asp
1               5

<210> SEQ ID NO 37
<211> LENGTH: 107
<212> TYPE: PRT
<213> ORGANISM: Artificial Sequence
<220> FEATURE:
<223> OTHER INFORMATION: 409D4E10-VL
```

```
<400> SEQUENCE: 37

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Leu Asp Gly Val Pro Ser Arg Phe Ser Gly
50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asn Glu Phe Pro Tyr
                85                  90                  95

Thr Phe Gly Gly Gly Thr Lys Leu Glu Ile Lys
            100                 105

<210> SEQ ID NO 38
<211> LENGTH: 11
<212> TYPE: PRT
<213> ORGANISM: Artificial Sequence
<220> FEATURE:
<223> OTHER INFORMATION: VL-CDR

<400> SEQUENCE: 38

Lys Ala Ser Gln Asp Ile Asn Ser Tyr Leu Ser
1               5                   10

<210> SEQ ID NO 39
<211> LENGTH: 7
<212> TYPE: PRT
<213> ORGANISM: Artificial Sequence
<220> FEATURE:
<223> OTHER INFORMATION: VL-CDR

<400> SEQUENCE: 39

Arg Ala Asn Arg Leu Leu Asp
1               5

<210> SEQ ID NO 40
<211> LENGTH: 9
<212> TYPE: PRT
<213> ORGANISM: Artificial Sequence
<220> FEATURE:
<223> OTHER INFORMATION: VL-CDR

<400> SEQUENCE: 40

Leu Gln Tyr Asn Glu Phe Pro Tyr Thr
1               5

<210> SEQ ID NO 41
<211> LENGTH: 117
<212> TYPE: PRT
<213> ORGANISM: Artificial Sequence
<220> FEATURE:
<223> OTHER INFORMATION: 553G8G8-VH

<400> SEQUENCE: 41

Arg Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Ile Lys Tyr
            20                  25                  30
```

```
Gly Val His Trp Val Arg Gln Ser Pro Gly Glu Gly Leu Glu Trp Leu
         35                  40                  45

Gly Val Ile Trp Arg Gly Gly Ile Thr Asp Tyr Asn Ala Ala Phe Met
 50                  55                  60

Ser Arg Leu Ser Ile Thr Lys Asp Asn Ser Lys Ser Gln Val Phe Phe
 65                  70                  75                  80

Lys Met Asn Ser Leu Gln Ala Asp Asp Thr Ala Ile Tyr Tyr Cys Ala
                 85                  90                  95

Lys Trp Asp Gly Pro Leu Ala Met Asp Tyr Trp Gly Gln Gly Thr Ser
                100                 105                 110

Val Thr Val Ser Ser
        115

<210> SEQ ID NO 42
<211> LENGTH: 5
<212> TYPE: PRT
<213> ORGANISM: Artificial Sequence
<220> FEATURE:
<223> OTHER INFORMATION: VH-CDR

<400> SEQUENCE: 42

Lys Tyr Gly Val His
 1               5

<210> SEQ ID NO 43
<211> LENGTH: 16
<212> TYPE: PRT
<213> ORGANISM: Artificial Sequence
<220> FEATURE:
<223> OTHER INFORMATION: VH-CDR

<400> SEQUENCE: 43

Val Ile Trp Arg Gly Gly Ile Thr Asp Tyr Asn Ala Ala Phe Met Ser
 1               5                  10                  15

<210> SEQ ID NO 44
<211> LENGTH: 9
<212> TYPE: PRT
<213> ORGANISM: Artificial Sequence
<220> FEATURE:
<223> OTHER INFORMATION: VH-CDR

<400> SEQUENCE: 44

Trp Asp Gly Pro Leu Ala Met Asp Tyr
 1               5

<210> SEQ ID NO 45
<211> LENGTH: 107
<212> TYPE: PRT
<213> ORGANISM: Artificial Sequence
<220> FEATURE:
<223> OTHER INFORMATION: 553G8G8-VL

<400> SEQUENCE: 45

Asp Val Gln Met Ile Gln Ser Pro Ser Ser Leu Ser Ala Ser Leu Gly
 1               5                  10                  15

Asp Met Val Thr Met Thr Cys Gln Ala Ser Gln Gly Thr Asn Ile Asn
                 20                  25                  30

Leu Asn Trp Phe Gln Gln Lys Pro Gly Lys Ala Pro Lys Leu Leu Ile
             35                  40                  45

Tyr Gly Ala Ser Asn Leu Glu Asp Gly Val Pro Ser Arg Phe Ser Gly
 50                  55                  60
```

```
Ser Arg Tyr Gly Thr Asp Phe Thr Leu Thr Ile Ser Ser Leu Glu Asp
 65                  70                  75                  80

Glu Asp Met Ala Thr Tyr Phe Gly Leu Gln His Ser Tyr Leu Pro Leu
                 85                  90                  95

Thr Phe Gly Ala Gly Thr Lys Leu Glu Leu Lys
            100                 105

<210> SEQ ID NO 46
<211> LENGTH: 11
<212> TYPE: PRT
<213> ORGANISM: Artificial Sequence
<220> FEATURE:
<223> OTHER INFORMATION: VL-CDR

<400> SEQUENCE: 46

Gln Ala Ser Gln Gly Thr Asn Ile Asn Leu Asn
1               5                   10

<210> SEQ ID NO 47
<211> LENGTH: 7
<212> TYPE: PRT
<213> ORGANISM: Artificial Sequence
<220> FEATURE:
<223> OTHER INFORMATION: VL-CDR

<400> SEQUENCE: 47

Gly Ala Ser Asn Leu Glu Asp
1               5

<210> SEQ ID NO 48
<211> LENGTH: 9
<212> TYPE: PRT
<213> ORGANISM: Artificial Sequence
<220> FEATURE:
<223> OTHER INFORMATION: VL-CDR

<400> SEQUENCE: 48

Leu Gln His Ser Tyr Leu Pro Leu Thr
1               5

<210> SEQ ID NO 49
<211> LENGTH: 342
<212> TYPE: DNA
<213> ORGANISM: Artificial Sequence
<220> FEATURE:
<223> OTHER INFORMATION: 405B8H3-VH

<400> SEQUENCE: 49
caggttcaac tgcagcagtc tggggctgag ctggtgaggc ctggggcttc agtgacgctg      60
tcctgcaagg cttcgggcta cacatttact gactatgaaa tgcactgggt gaagcagaca     120
cctgtgcatg gcctggaatg gattggagcc actgatcctg aaactggtaa tagtgcctac     180
aatcagaagt tcaagggcaa ggccataatg actgcagaca atcctccag cacagcctac     240 atggagctcc gcagcctgac atctgaggac tctgccgtct attactgtat atcaactggg     300
tggaatgact ggggccaagg caccagtctc acagtctcct ca                       342

<210> SEQ ID NO 50
<211> LENGTH: 321
<212> TYPE: DNA
<213> ORGANISM: Artificial Sequence
<220> FEATURE:
<223> OTHER INFORMATION: 405B8H3-VL
```

```
<400> SEQUENCE: 50
gacatcaaga tgacccagtc tccatcttcc atgtatgcat ctctaggaga gagagtcact    60
atcacttgca aggcgagtca ggacattaat agctatttaa gctggttcca gcagaaacca   120
gggaaatctc ctaagaccct gatctatcgt gcagacagat tgttagatgg ggtcccatca   180
aggttcagtg gcagtggatc tgggcaagat tattctctca ccatcagcag cctggagtat   240
ggagatatgg gaatttatta ttgtctacag tatgatgagt ttccgtacac gttcggaggg   300
gggaccaagc tggaaataaa a                                             321

<210> SEQ ID NO 51
<211> LENGTH: 351
<212> TYPE: DNA
<213> ORGANISM: Artificial Sequence
<220> FEATURE:
<223> OTHER INFORMATION: 556F6B8-VH

<400> SEQUENCE: 51
cgggtgcagc tgaagcagtc aggacctggc ctagtgcagc cctcacagag cctgtccata    60
acctgcacag tctctggttt ctcattaatt aagtacggtg tacactgggt tcgccagtct   120
ccaggagagg gtctggagtg gctgggagtg atatggagag gtggcatcac agactacaat   180
gcagctttca tgtccagact gagcatcacc aaggacaact ccaagagcca agttttcttt   240
aaaatgaaca gtctgcaagc tgatgacact gccatatact actgtgccaa atgggacggg   300
cccctggcta tggactactg gggtcaagga acctcagtca ccgtctcctc a            351

<210> SEQ ID NO 52
<211> LENGTH: 321
<212> TYPE: DNA
<213> ORGANISM: Artificial Sequence
<220> FEATURE:
<223> OTHER INFORMATION: 556F6B8-VL

<400> SEQUENCE: 52
gacattgtga tgacccagtc tcacaaattc ttgtccacat cagtaggaga cagggtcagc    60
atcacctgca aggccagtca ggatgtgggt actactgtag cctggtatca acagaaacca   120
ggacaatctc ctaaactact gatttactgg gcatccaccc ggcacactgg agtccctgat   180
cgcttcacag gcagtggatc tgggacagat ttcactctca ccattagcaa tgtgcagtct   240
gaagacttgg cagattattt ctgtcagcaa tatagcagct atccgtacac gttcggaggg   300
gggaccaagc tagaaataaa a                                             321

<210> SEQ ID NO 53
<211> LENGTH: 345
<212> TYPE: DNA
<213> ORGANISM: Artificial Sequence
<220> FEATURE:
<223> OTHER INFORMATION: 105F1E10-VH

<400> SEQUENCE: 53
gaggtccagc tgcaacagtc tggacctgag ctggtgaagc ctggggcttc agtgaagatg    60
tcctgcaggg cttctggata cacattcact gacttcaaaa tgcactggat gaagcagagc   120
catggaaaga gccttgagtg gattggatat attgccccta acaatggtgg tactgcctac   180
aatcagaaat tcaggggcaa ggccacattg actgtaaacg agtcctccaa cacagcctac   240
```

```
atggagctcc gcagcctgac atcggaagat tctgcagtct attactgtgt ggactgggac    300
gacgttgact actggggcca aggcaccact ctcacagtct cctca                    345
```

```
<210> SEQ ID NO 54
<211> LENGTH: 321
<212> TYPE: DNA
<213> ORGANISM: Artificial Sequence
<220> FEATURE:
<223> OTHER INFORMATION: 105F1E10-VL

<400> SEQUENCE: 54
gacatcaaga tgacccagtc tccatcttcc atgtatgcat ctctaggaga gagagtcact     60
atcacttgca aggcgagtca ggacattaat agctatttaa gctggttcca gcagaaatca    120
gggaaatctc ctaagaccct gatctatcgt gcaaatagat tggtagatgg ggtcccatca    180
aggttcagtg gcagtggatc tgggcaagat tattctctca ccatcagcag cctggagtat    240
gaagatatgg gaatttatta ttgtctacag tatgttgagt ttcctctcac gttcggtgct    300
gggaccaagc tggagctgaa a                                              321
```

```
<210> SEQ ID NO 55
<211> LENGTH: 342
<212> TYPE: DNA
<213> ORGANISM: Artificial Sequence
<220> FEATURE:
<223> OTHER INFORMATION: 409B11E12-VH

<400> SEQUENCE: 55
caggttcaac tgcagcagtc tggggctgag ctggtgaggc ctggggcttc agtgacgctg     60
tcctgcaagg cttcgggcta cacatttact gactatgaaa tgcactgggt gaagcagaca    120
actgtgcatg gcctggaatg gattggagcc actgatcctg aaactagtta tagtgcctac    180
aatcagaagt tcaagggcaa ggccatactg actgcagaca atcctccag cacagcctac     240 atggagctcc gcagcctgac atctgaggac tctgccgtct attactgtat agcaactggg    300
tggaacgact ggggccaagg caccagtctc acagtctcct ca                       342
```

```
<210> SEQ ID NO 56
<211> LENGTH: 321
<212> TYPE: DNA
<213> ORGANISM: Artificial Sequence
<220> FEATURE:
<223> OTHER INFORMATION: 409B11E12-VL

<400> SEQUENCE: 56
gacctcaaga tgacccagtc tccatcttcc atgtatgcat ctctaggaga gagagtcact     60
atcacttgca aggcgagtca ggacattaat agctatttaa gttggttcca gcagaaacca    120
gggaaatctc ctaagaccct gatctatcgt gcaaacagat tgttagatgg ggtcccatca    180
aggttcagtg gcagtggatc tgggcaagat tattctctca ccatcagcag cctggagtat    240
gaagatatgg gaatttatta ttgtctacag tatgatgagt ttccgtacac attcggaggg    300
gggaccaagc tggaaataaa a                                              321
```

```
<210> SEQ ID NO 57
<211> LENGTH: 342
<212> TYPE: DNA
<213> ORGANISM: Artificial Sequence
<220> FEATURE:
<223> OTHER INFORMATION: 409D4E10-VH
```

<400> SEQUENCE: 57

| | |
|---|---|
| caggttcaac tgcagcagtc tggggctgag ctggtgaggc ctggggcttc agtgacgctg | 60 |
| tcctgcaagg cttcgggcaa cacatttact gactatgaaa tgcactgggt gaagcagaca | 120 |
| cctgtgcatg gcctggaatg gattggagcc actgatcctg aaactgataa tactgcctac | 180 |
| aatcagaagt tcaagggcaa ggccatactg actacagaca atcctccag cacagcctac | 240 |
| atggagctcc gcagcctgac atctgaggac tctgccgtct attattgcat aacaagtggg | 300 |
| tggaacgact ggggccaagg caccagtctc acagtctcct ca | 342 |

<210> SEQ ID NO 58
<211> LENGTH: 321
<212> TYPE: DNA
<213> ORGANISM: Artificial Sequence
<220> FEATURE:
<223> OTHER INFORMATION: 409D4E10-VL

<400> SEQUENCE: 58

| | |
|---|---|
| gacatcaaga tgacccagtc tccatcttcc atgtatgcat ctctaggaga gagagtcact | 60 |
| atcacttgca aggcgagtca ggacattaat agctatttaa gctggttcca gcagaaacca | 120 |
| gggaaatctc ctaagaccct gatctatcgt gcaaacagat tgttagatgg ggtcccatca | 180 |
| aggttcagtg gcagtggatc tgggcaagat tattctctca ccatcagcag cctggaatat | 240 |
| gaagatatgg gaatttatta ttgtctacag tataatgagt ttccgtacac gttcggaggg | 300 |
| gggaccaagc tggaaataaa a | 321 |

<210> SEQ ID NO 59
<211> LENGTH: 351
<212> TYPE: DNA
<213> ORGANISM: Artificial Sequence
<220> FEATURE:
<223> OTHER INFORMATION: 553G8G8-VH

<400> SEQUENCE: 59

| | |
|---|---|
| cgggtgcagc tgaagcagtc aggacctggc ctagtgcagc cctcacagag cctgtccata | 60 |
| acctgcacag tctctggttt ctcattaatt aagtacggtg tacactgggt tcgccagtct | 120 |
| ccaggagagg gtctggagtg gctgggagtg atatggagag gtggcatcac agactacaat | 180 |
| gcagctttca tgtccagact gagcatcacc aaggacaact ccaagagcca agttttcttt | 240 |
| aaaatgaaca gtctgcaagc tgatgacact gccatatact actgtgccaa atgggacggg | 300 |
| cccctggcta tggactactg gggtcaagga acctcagtca ccgtctcctc a | 351 |

<210> SEQ ID NO 60
<211> LENGTH: 321
<212> TYPE: DNA
<213> ORGANISM: Artificial Sequence
<220> FEATURE:
<223> OTHER INFORMATION: 553G8G8-VL

<400> SEQUENCE: 60

| | |
|---|---|
| gatgtccaga tgattcagtc tccatcctcc ctgtctgcat ctttgggaga catggtcacc | 60 |
| atgacttgcc aggcaagtca ggcactaac attaatttaa actggtttca gcaaaaacca | 120 |
| gggaaagctc ctaagctcct gatctatggt gcaagcaact ggaagatgg ggtcccatca | 180 |
| aggttcagtg gcagtagata tggacagat ttcactctca ccatcagcag cctggaggat | 240 |
| gaagatatgg caacgtattt cggtctacag catagttatc tcccgctcac gttcggtgct | 300 |
| gggaccaagc tggagctgaa a | 321 |

-continued

```
<210> SEQ ID NO 61
<211> LENGTH: 525
<212> TYPE: PRT
<213> ORGANISM: Artificial Sequence
<220> FEATURE:
<223> OTHER INFORMATION: human LAG-3

<400> SEQUENCE: 61
```

Met Trp Glu Ala Gln Phe Leu Gly Leu Leu Phe Leu Gln Pro Leu Trp
1               5                   10                  15

Val Ala Pro Val Lys Pro Leu Gln Pro Gly Ala Glu Val Pro Val Val
                20                  25                  30

Trp Ala Gln Glu Gly Ala Pro Ala Gln Leu Pro Cys Ser Pro Thr Ile
            35                  40                  45

Pro Leu Gln Asp Leu Ser Leu Leu Arg Arg Ala Gly Val Thr Trp Gln
        50                  55                  60

His Gln Pro Asp Ser Gly Pro Pro Ala Ala Pro Gly His Pro Leu
65                  70                  75                  80

Ala Pro Gly Pro His Pro Ala Ala Pro Ser Ser Trp Gly Pro Arg Pro
                85                  90                  95

Arg Arg Tyr Thr Val Leu Ser Val Gly Pro Gly Gly Leu Arg Ser Gly
            100                 105                 110

Arg Leu Pro Leu Gln Pro Arg Val Gln Leu Asp Glu Arg Gly Arg Gln
        115                 120                 125

Arg Gly Asp Phe Ser Leu Trp Leu Arg Pro Ala Arg Arg Ala Asp Ala
    130                 135                 140

Gly Glu Tyr Arg Ala Ala Val His Leu Arg Asp Arg Ala Leu Ser Cys
145                 150                 155                 160

Arg Leu Arg Leu Arg Leu Gly Gln Ala Ser Met Thr Ala Ser Pro Pro
                165                 170                 175

Gly Ser Leu Arg Ala Ser Asp Trp Val Ile Leu Asn Cys Ser Phe Ser
            180                 185                 190

Arg Pro Asp Arg Pro Ala Ser Val His Trp Phe Arg Asn Arg Gly Gln
        195                 200                 205

Gly Arg Val Pro Val Arg Glu Ser Pro His His Leu Ala Glu Ser
    210                 215                 220

Phe Leu Phe Leu Pro Gln Val Ser Pro Met Asp Ser Gly Pro Trp Gly
225                 230                 235                 240

Cys Ile Leu Thr Tyr Arg Asp Gly Phe Asn Val Ser Ile Met Tyr Asn
                245                 250                 255

Leu Thr Val Leu Gly Leu Glu Pro Pro Thr Pro Leu Thr Val Tyr Ala
            260                 265                 270

Gly Ala Gly Ser Arg Val Gly Leu Pro Cys Arg Leu Pro Ala Gly Val
        275                 280                 285

Gly Thr Arg Ser Phe Leu Thr Ala Lys Trp Thr Pro Pro Gly Gly Gly
    290                 295                 300

Pro Asp Leu Leu Val Thr Gly Asp Asn Gly Asp Phe Thr Leu Arg Leu
305                 310                 315                 320

Glu Asp Val Ser Gln Ala Gln Ala Gly Thr Tyr Thr Cys His Ile His
                325                 330                 335

Leu Gln Glu Gln Gln Leu Asn Ala Thr Val Thr Leu Ala Ile Ile Thr
            340                 345                 350

Val Thr Pro Lys Ser Phe Gly Ser Pro Gly Ser Leu Gly Lys Leu Leu
        355                 360                 365

```
Cys Glu Val Thr Pro Val Ser Gly Gln Glu Arg Phe Val Trp Ser Ser
        370                 375                 380
Leu Asp Thr Pro Ser Gln Arg Ser Phe Ser Gly Pro Trp Leu Glu Ala
385                 390                 395                 400
Gln Glu Ala Gln Leu Leu Ser Gln Pro Trp Gln Cys Gln Leu Tyr Gln
                405                 410                 415
Gly Glu Arg Leu Leu Gly Ala Ala Val Tyr Phe Thr Glu Leu Ser Ser
                420                 425                 430
Pro Gly Ala Gln Arg Ser Gly Arg Ala Pro Gly Ala Leu Pro Ala Gly
                435                 440                 445
His Leu Leu Phe Leu Ile Leu Gly Val Leu Ser Leu Leu Leu Leu Leu
        450                 455                 460
Val Thr Gly Ala Phe Gly Phe His Leu Trp Arg Arg Gln Trp Arg Pro
465                 470                 475                 480
Arg Arg Phe Ser Ala Leu Glu Gln Gly Ile His Pro Pro Gln Ala Gln
                485                 490                 495
Ser Lys Ile Glu Glu Leu Glu Gln Glu Pro Glu Pro Glu Pro Glu Pro
                500                 505                 510
Glu Pro Glu Pro Glu Pro Glu Pro Glu Gln Leu
                515                 520                 525

<210> SEQ ID NO 62
<211> LENGTH: 533
<212> TYPE: PRT
<213> ORGANISM: Artificial Sequence
<220> FEATURE:
<223> OTHER INFORMATION: monkey LAG-3

<400> SEQUENCE: 62

Met Trp Glu Ala Gln Phe Leu Gly Leu Leu Phe Leu Gln Pro Leu Trp
1               5                   10                  15
Val Ala Pro Val Lys Pro Pro Gln Pro Gly Ala Glu Ile Ser Val Val
                20                  25                  30
Trp Ala Gln Glu Gly Ala Pro Ala Gln Leu Pro Cys Ser Pro Thr Ile
            35                  40                  45
Pro Leu Gln Asp Leu Ser Leu Leu Arg Arg Ala Gly Val Thr Trp Gln
    50                  55                  60
His Gln Pro Asp Ser Gly Pro Pro Ala Pro Ala Pro Gly His Pro Pro
65                  70                  75                  80
Ala Pro Gly His Arg Pro Ala Ala Pro Tyr Ser Trp Gly Pro Arg Pro
                85                  90                  95
Arg Arg Tyr Thr Val Leu Ser Val Gly Pro Gly Gly Leu Arg Ser Gly
                100                 105                 110
Arg Leu Pro Leu Gln Pro Arg Val Gln Leu Asp Glu Arg Gly Arg Gln
            115                 120                 125
Arg Gly Asp Phe Ser Leu Trp Leu Arg Pro Ala Arg Arg Ala Asp Ala
    130                 135                 140
Gly Glu Tyr Arg Ala Thr Val His Leu Arg Asp Arg Ala Leu Ser Cys
145                 150                 155                 160
Arg Leu Arg Leu Arg Val Gly Gln Ala Ser Met Thr Ala Ser Pro Pro
                165                 170                 175
Gly Ser Leu Arg Thr Ser Asp Trp Val Ile Leu Asn Cys Ser Phe Ser
                180                 185                 190
Arg Pro Asp Arg Pro Ala Ser Val His Trp Phe Arg Ser Arg Gly Gln
            195                 200                 205
```

-continued

Gly Arg Val Pro Val Gln Gly Ser Pro His His Leu Ala Glu Ser
        210                 215                 220

Phe Leu Phe Leu Pro His Val Gly Pro Met Asp Ser Gly Leu Trp Gly
225                 230                 235                 240

Cys Ile Leu Thr Tyr Arg Asp Gly Phe Asn Val Ser Ile Met Tyr Asn
                245                 250                 255

Leu Thr Val Leu Gly Leu Glu Pro Ala Thr Pro Leu Thr Val Tyr Ala
            260                 265                 270

Gly Ala Gly Ser Arg Val Glu Leu Pro Cys Arg Leu Pro Pro Ala Val
        275                 280                 285

Gly Thr Gln Ser Phe Leu Thr Ala Lys Trp Ala Pro Pro Gly Gly Gly
    290                 295                 300

Pro Asp Leu Leu Val Ala Gly Asp Asn Gly Asp Phe Thr Leu Arg Leu
305                 310                 315                 320

Glu Asp Val Ser Gln Ala Gln Ala Gly Thr Tyr Ile Cys His Ile Arg
                325                 330                 335

Leu Gln Gly Gln Gln Leu Asn Ala Thr Val Thr Leu Ala Ile Ile Thr
            340                 345                 350

Val Thr Pro Lys Ser Phe Gly Ser Pro Gly Ser Leu Gly Lys Leu Leu
        355                 360                 365

Cys Glu Val Thr Pro Ala Ser Gly Gln Glu His Phe Val Trp Ser Pro
370                 375                 380

Leu Asn Thr Pro Ser Gln Arg Ser Phe Ser Gly Pro Trp Leu Glu Ala
385                 390                 395                 400

Gln Glu Ala Gln Leu Leu Ser Gln Pro Trp Gln Cys Gln Leu His Gln
                405                 410                 415

Gly Glu Arg Leu Leu Gly Ala Ala Val Tyr Phe Thr Glu Leu Ser Ser
            420                 425                 430

Pro Gly Ala Gln Arg Ser Gly Arg Ala Pro Gly Ala Leu Arg Ala Gly
        435                 440                 445

His Leu Pro Leu Phe Leu Ile Leu Gly Val Leu Phe Leu Leu Leu Leu
    450                 455                 460

Val Thr Gly Ala Phe Gly Phe His Leu Trp Arg Arg Gln Trp Arg Pro
465                 470                 475                 480

Arg Arg Phe Ser Ala Leu Glu Gln Gly Ile His Pro Pro Gln Ala Gln
                485                 490                 495

Ser Lys Ile Glu Glu Leu Glu Gln Glu Pro Glu Leu Glu Pro Glu Pro
            500                 505                 510

Glu Leu Glu Arg Glu Leu Gly Pro Glu Pro Glu Pro Gly Pro Glu Pro
        515                 520                 525

Glu Pro Glu Gln Leu
    530

<210> SEQ ID NO 63
<211> LENGTH: 521
<212> TYPE: PRT
<213> ORGANISM: Artificial Sequence
<220> FEATURE:
<223> OTHER INFORMATION: mouse LAG-3

<400> SEQUENCE: 63

Met Arg Glu Asp Leu Leu Leu Gly Phe Leu Leu Leu Gly Leu Leu Trp
1               5                   10                  15

Glu Ala Pro Val Val Ser Ser Gly Pro Gly Lys Glu Leu Pro Val Val
            20                  25                  30

-continued

```
Trp Ala Gln Glu Gly Ala Pro Val His Leu Pro Cys Ser Leu Lys Ser
     35                  40                  45

Pro Asn Leu Asp Pro Asn Phe Leu Arg Arg Gly Val Ile Trp Gln
 50                  55                  60

His Gln Pro Asp Ser Gly Gln Pro Thr Pro Ile Pro Ala Leu Asp Leu
 65                  70                  75                  80

His Gln Gly Met Pro Ser Pro Arg Gln Pro Ala Pro Gly Arg Tyr Thr
                 85                  90                  95

Val Leu Ser Val Ala Pro Gly Gly Leu Arg Ser Gly Arg Gln Pro Leu
                100                 105                 110

His Pro His Val Gln Leu Glu Arg Gly Leu Gln Arg Gly Asp Phe
            115                 120                 125

Ser Leu Trp Leu Arg Pro Ala Leu Arg Thr Asp Ala Gly Glu Tyr His
130                 135                 140

Ala Thr Val Arg Leu Pro Asn Arg Ala Leu Ser Cys Ser Leu Arg Leu
145                 150                 155                 160

Arg Val Gly Gln Ala Ser Met Ile Ala Ser Pro Ser Gly Val Leu Lys
                165                 170                 175

Leu Ser Asp Trp Val Leu Leu Asn Cys Ser Phe Ser Arg Pro Asp Arg
            180                 185                 190

Pro Val Ser Val His Trp Phe Gln Gly Gln Asn Arg Val Pro Val Tyr
            195                 200                 205

Asn Ser Pro Arg His Phe Leu Ala Glu Thr Phe Leu Leu Leu Pro Gln
210                 215                 220

Val Ser Pro Leu Asp Ser Gly Thr Trp Gly Cys Val Leu Thr Tyr Arg
225                 230                 235                 240

Asp Gly Phe Asn Val Ser Ile Thr Tyr Asn Leu Lys Val Leu Gly Leu
                245                 250                 255

Glu Pro Val Ala Pro Leu Thr Val Tyr Ala Ala Glu Gly Ser Arg Val
            260                 265                 270

Glu Leu Pro Cys His Leu Pro Pro Gly Val Gly Thr Pro Ser Leu Leu
            275                 280                 285

Ile Ala Lys Trp Thr Pro Pro Gly Gly Gly Pro Glu Leu Pro Val Ala
290                 295                 300

Gly Lys Ser Gly Asn Phe Thr Leu His Leu Glu Ala Val Gly Leu Ala
305                 310                 315                 320

Gln Ala Gly Thr Tyr Thr Cys Ser Ile His Leu Gln Gly Gln Gln Leu
                325                 330                 335

Asn Ala Thr Val Thr Leu Ala Val Ile Thr Val Thr Pro Lys Ser Phe
            340                 345                 350

Gly Leu Pro Gly Ser Arg Gly Lys Leu Leu Cys Glu Val Thr Pro Ala
            355                 360                 365

Ser Gly Lys Glu Arg Phe Val Trp Arg Pro Leu Asn Asn Leu Ser Arg
370                 375                 380

Ser Cys Pro Gly Pro Val Leu Glu Ile Gln Glu Ala Arg Leu Leu Ala
385                 390                 395                 400

Glu Arg Trp Gln Cys Gln Leu Tyr Glu Gly Gln Arg Leu Leu Gly Ala
                405                 410                 415

Thr Val Tyr Ala Ala Glu Ser Ser Gly Ala His Ser Ala Arg Arg
            420                 425                 430

Ile Ser Gly Asp Leu Lys Gly Gly His Leu Val Leu Val Leu Ile Leu
435                 440                 445
```

```
Gly Ala Leu Ser Leu Phe Leu Leu Val Ala Gly Ala Phe Gly Phe His
            450             455                 460

Trp Trp Arg Lys Gln Leu Leu Arg Arg Phe Ser Ala Leu Glu His
465             470                 475                 480

Gly Ile Gln Pro Phe Pro Ala Gln Arg Lys Ile Glu Glu Leu Glu Arg
                485                 490                 495

Glu Leu Glu Thr Glu Met Gly Gln Glu Pro Glu Pro Glu Pro
            500                 505                 510

Gln Leu Glu Pro Glu Pro Arg Gln Leu
            515                 520

<210> SEQ ID NO 64
<211> LENGTH: 114
<212> TYPE: PRT
<213> ORGANISM: Artificial Sequence
<220> FEATURE:
<223> OTHER INFORMATION: humanized VH1

<400> SEQUENCE: 64

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Met
        35                  40                  45

Gly Ala Thr Asp Pro Glu Thr Gly Asn Ser Ala Tyr Asn Gln Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ile Ser Thr Gly Trp Asn Asp Trp Gly Gln Gly Thr Thr Val Thr Val
            100                 105                 110

Ser Ser

<210> SEQ ID NO 65
<211> LENGTH: 342
<212> TYPE: DNA
<213> ORGANISM: Artificial Sequence
<220> FEATURE:
<223> OTHER INFORMATION: humanized VH1

<400> SEQUENCE: 65
caggtgcagc tggtgcagag cggcgctgaa gtgaagaagc cggcgccag cgtgaaggtg      60 agctgcaagg ccagcggcta caccttcacc gactacgaga tgcactgggt gagacaggct    120
cctggccagg gcctggagtg gatgggagcc accgatcccg agaccggcaa cagcgcctat    180
aaccagaagt tcaagggcag ggtgaccatg accaggaca ccagcaccag caccgtgtac     240
atggagctga gcagcctgag gagcgaggac accgccgtgt actactgcat cagcaccggc    300
tggaacgact ggggacaggg caccaccgtg accgtgagca gc                       342

<210> SEQ ID NO 66
<211> LENGTH: 114
<212> TYPE: PRT
<213> ORGANISM: Artificial Sequence
<220> FEATURE:
<223> OTHER INFORMATION: humanized VH2
```

<400> SEQUENCE: 66

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Met
        35                  40                  45

Gly Ala Thr Asp Pro Glu Thr Gly Asn Ser Ala Tyr Asn Gln Lys Phe
    50                  55                  60

Lys Gly Arg Val Thr Met Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ile Ser Thr Gly Trp Asn Asp Trp Gly Gln Gly Thr Thr Val Thr Val
            100                 105                 110

Ser Ser

<210> SEQ ID NO 67
<211> LENGTH: 342
<212> TYPE: DNA
<213> ORGANISM: Artificial Sequence
<220> FEATURE:
<223> OTHER INFORMATION: humanized VH2

<400> SEQUENCE: 67
caggtgcagc tggtgcagag cggcgctgaa gtgaagaagc ccggcgccag cgtgaaggtg      60
agctgcaagg ccagcggcta caccttcacc gactacgaga tgcactgggt gagacaggct     120
cctggccagg gctggagtg atgggagcc accgatccg agaccggcaa cagcgcctat     180
aaccagaagt tcaagggcag ggtgaccatg accgccgaca gagcaccag caccgtgtac     240 atggagctga gcagcctgag gagcgaggac accgccgtgt actactgcat cagcaccggc     300
tggaacgact ggggacaggg caccaccgtg accgtgagca gc                        342

<210> SEQ ID NO 68
<211> LENGTH: 114
<212> TYPE: PRT
<213> ORGANISM: Artificial Sequence
<220> FEATURE:
<223> OTHER INFORMATION: humanized VH3

<400> SEQUENCE: 68

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Ile
        35                  40                  45

Gly Ala Thr Asp Pro Glu Thr Gly Asn Ser Ala Tyr Asn Gln Lys Phe
    50                  55                  60

Lys Gly Arg Ala Thr Met Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ile Ser Thr Gly Trp Asn Asp Trp Gly Gln Gly Thr Thr Val Thr Val
                100                 105                 110

Ser Ser

<210> SEQ ID NO 69
<211> LENGTH: 342
<212> TYPE: DNA
<213> ORGANISM: Artificial Sequence
<220> FEATURE:
<223> OTHER INFORMATION: humanized VH3

<400> SEQUENCE: 69
caggtgcagc tggtgcagag cggcgccgaa gtgaagaagc tggcgccag cgtgaaggtg      60 tcctgcaagg ccagcggcta caccttcacc gactacgaga tgcactggg gaggcaggct     120 cctggacagg gcctggagtg gattggcgcc acagaccccg agaccggcaa tagcgcctac    180
aaccagaagt tcaagggcag ggccacaatg accgccgaca gagcaccag caccgcctac    240 atggagctga gcagcctgag gagcgaggac accgccgtgt actactgcat ctccaccggc    300
tggaacgact ggggacaggg caccaccgtg accgtgagca gc                       342

<210> SEQ ID NO 70
<211> LENGTH: 117
<212> TYPE: PRT
<213> ORGANISM: Artificial Sequence
<220> FEATURE:
<223> OTHER INFORMATION: humanized VH4

<400> SEQUENCE: 70

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ile Lys Tyr
                20                  25                  30

Gly Val His Trp Ile Arg Gln Pro Pro Gly Lys Gly Leu Glu Trp Ile
            35                  40                  45

Gly Val Ile Trp Arg Gly Gly Ile Thr Asp Tyr Asn Ala Ala Phe Met
        50                  55                  60

Ser Arg Val Thr Ile Ser Lys Asp Thr Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Arg Trp Glu Gly Pro Leu Ala Met Asp Tyr Trp Gly Gln Gly Thr Thr
            100                 105                 110

Val Thr Val Ser Ser
        115

<210> SEQ ID NO 71
<211> LENGTH: 351
<212> TYPE: DNA
<213> ORGANISM: Artificial Sequence
<220> FEATURE:
<223> OTHER INFORMATION: humanized VH4

<400> SEQUENCE: 71
caggtgcagc tgcaggagtc cggacctggc ctggtgaagc ccagcgagac cctgagcctg     60
acctgcaccg tgagcggctt cagcctgatc aagtacggcg tgcactggat caggcagcct   120
cccgaaaagg gcctggagtg gatcggcgtc atctggaggg gcggcatcac cgactacaac    180
gccgccttca tgagcagggt gaccatcagc aaggacacca gcaagagcca ggtgagcctg    240

```
aagctgagca gcgtgacagc cgccgacaca gccgtgtact actgtgccag gtgggaaggc    300
cccctggcca tggattactg ggccagggc accacagtga ccgtgagcag c              351
```

<210> SEQ ID NO 72
<211> LENGTH: 117
<212> TYPE: PRT
<213> ORGANISM: Artificial Sequence
<220> FEATURE:
<223> OTHER INFORMATION: humanized VH5

<400> SEQUENCE: 72

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ile Lys Tyr
            20                  25                  30

Gly Val His Trp Ile Arg Gln Pro Pro Gly Lys Gly Leu Glu Trp Ile
        35                  40                  45

Gly Val Ile Trp Arg Gly Gly Ile Thr Asp Tyr Asn Ala Ala Phe Met
    50                  55                  60

Ser Arg Val Thr Ile Ser Lys Asp Thr Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Arg Trp Asp Gly Pro Leu Ala Met Asp Tyr Trp Gly Gln Gly Thr Thr
            100                 105                 110

Val Thr Val Ser Ser
        115
```

<210> SEQ ID NO 73
<211> LENGTH: 351
<212> TYPE: DNA
<213> ORGANISM: Artificial Sequence
<220> FEATURE:
<223> OTHER INFORMATION: humanized VH5

<400> SEQUENCE: 73

```
caggtgcagc tgcaggagtc cggacctggc ctggtgaagc ccagcgagac cctgagcctg    60
acctgcaccg tgagcggctt cagcctgatc aagtacggcg tgcactggat caggcagcct    120
cccggaaagg gcctggagtg gatcggcgtc atctggaggg gcggcatcac cgactacaac    180
gccgccttca tgagcagggt gaccatcagc aaggacacca gcaagagcca ggtgagcctg    240
aagctgagca gcgtgacagc cgccgacaca gccgtgtact actgtgccag gtgggatggc    300
cccctggcca tggattactg ggccagggc accacagtga ccgtgagcag c              351
```

<210> SEQ ID NO 74
<211> LENGTH: 107
<212> TYPE: PRT
<213> ORGANISM: Artificial Sequence
<220> FEATURE:
<223> OTHER INFORMATION: humanized VL1

<400> SEQUENCE: 74

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45
```

```
Tyr Arg Ala Asp Arg Leu Leu Glu Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Leu Glu Ile Lys
            100                 105

<210> SEQ ID NO 75
<211> LENGTH: 321
<212> TYPE: DNA
<213> ORGANISM: Artificial Sequence
<220> FEATURE:
<223> OTHER INFORMATION: humanized VL1

<400> SEQUENCE: 75
gacatccaga tgacccagag ccctagcagc ctgagcgcta gcgtgggcga cagagtgacc       60
atcacctgca aggccagcca ggacatcaac agctacctga gctggttcca gcagaagccc      120
ggcaaggccc ctaagagcct gatctacagg gccgacagac tgctggaagg cgtgcctagc      180
aggtttagcg gcagcggcag cggcaccgat ttcaccctga ccatcagcag cctgcagccc      240
gaggacttcg ccacctacta ctgcctgcag tacgacgagt tcccctacac cttcggccag      300
ggcaccaagc tggagatcaa g                                                321

<210> SEQ ID NO 76
<211> LENGTH: 107
<212> TYPE: PRT
<213> ORGANISM: Artificial Sequence
<220> FEATURE:
<223> OTHER INFORMATION: humanized VL2

<400> SEQUENCE: 76

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asp Ile Asn Ser Tyr
                20                  25                  30

Leu Ser Trp Phe Gln Gln Lys Pro Gly Lys Ala Pro Lys Ser Leu Ile
            35                  40                  45

Tyr Arg Ala Asp Arg Leu Leu Asp Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Leu Glu Ile Lys
            100                 105

<210> SEQ ID NO 77
<211> LENGTH: 321
<212> TYPE: DNA
<213> ORGANISM: Artificial Sequence
<220> FEATURE:
<223> OTHER INFORMATION: humanized VL2

<400> SEQUENCE: 77
gacatccaga tgacccagag ccctagcagc ctgagcgcta gcgtgggcga cagagtgacc       60
atcacctgca aggccagcca ggacatcaac agctacctga gctggttcca gcagaagccc      120
```

```
ggcaaggccc ctaagagcct gatctacagg gccgacagac tgctggacgg cgtgcctagc      180
aggtttagcg gcagcggcag cggcaccgat tcaccctga ccatcagcag cctgcagccc      240
gaggacttcg ccacctacta ctgcctgcag tacgacgagt tccccctacac cttcggccag     300 ggcaccaagc tggagatcaa g                                                321
```

```
<210> SEQ ID NO 78
<211> LENGTH: 107
<212> TYPE: PRT
<213> ORGANISM: Artificial Sequence
<220> FEATURE:
<223> OTHER INFORMATION: humanized VL3

<400> SEQUENCE: 78
```

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asp Arg Leu Leu Asp Gly Val Pro Ser Arg Phe Ser Gly
    50                  55                  60

Ser Gly Ser Gly Gln Asp Tyr Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Leu Glu Ile Lys
            100                 105

```
<210> SEQ ID NO 79
<211> LENGTH: 321
<212> TYPE: DNA
<213> ORGANISM: Artificial Sequence
<220> FEATURE:
<223> OTHER INFORMATION: humanized VL3

<400> SEQUENCE: 79
gacatccaga tgacccagag ccctagcagc ctgagcgcta gcgtgggcga cagagtgacc      60
atcacctgca aggccagcca ggacatcaac agctacctga ctggttcca gcagaagccc      120 ggcaaggccc ctaagagcct gatctacagg gccgacagac tgctggacgg cgtgcctagc     180
aggtttagcg gcagcggcag cggccaggat tacaccctga ccatcagcag cctgcagccc     240
gaggacttcg ccacctacta ctgcctgcag tacgacgagt tccccctacac cttcggccag    300 ggcaccaagc tggagatcaa g                                                321
```

```
<210> SEQ ID NO 80
<211> LENGTH: 107
<212> TYPE: PRT
<213> ORGANISM: Artificial Sequence
<220> FEATURE:
<223> OTHER INFORMATION: humanized VL4

<400> SEQUENCE: 80
```

Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asp Val Gly Thr Thr
            20                  25                  30

```
Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Ser Ser Tyr Pro Tyr
                85                  90                  95

Thr Phe Gly Gln Gly Thr Lys Leu Glu Ile Lys
            100                 105

<210> SEQ ID NO 81
<211> LENGTH: 321
<212> TYPE: DNA
<213> ORGANISM: Artificial Sequence
<220> FEATURE:
<223> OTHER INFORMATION: humanized VL4

<400> SEQUENCE: 81
gacatccagc tgacccagag ccccagcttt ctgagcgcca gcgtgggcga cagggtgacc      60
atcacctgca aggccagcca ggacgtgggc accacagtgg cctggtacca gcagaagccc     120
ggcaaggccc ccaagctgct gatctactgg gccagcacca gcatacagg cgtgcccagc      180 agattcagcg gcagcggaag cggcaccgag ttcaccctga ccatcagcag cctgcagccc     240
gaggacttcg ccacctacta ctgccagcag tacagctcct accectacac cttcggccag     300 ggcaccaagc tggagatcaa g                                               321

<210> SEQ ID NO 82
<211> LENGTH: 107
<212> TYPE: PRT
<213> ORGANISM: Artificial Sequence
<220> FEATURE:
<223> OTHER INFORMATION: humanized VL5

<400> SEQUENCE: 82

Asp Ile Val Leu Thr Gln Ser Pro Ser Phe Leu Ser Ala Ser Val Gly
1               5                   10                  15

Asp Arg Val Thr Ile Thr Cys Lys Ala Ser Gln Asp Val Gly Thr Thr
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Ser Ser Tyr Pro Tyr
                85                  90                  95

Thr Phe Gly Gln Gly Thr Lys Leu Glu Ile Lys
            100                 105

<210> SEQ ID NO 83
<211> LENGTH: 321
<212> TYPE: DNA
<213> ORGANISM: Artificial Sequence
<220> FEATURE:
<223> OTHER INFORMATION: humanized VL5
```

<400> SEQUENCE: 83

```
gacatcgtgc tgacccagag ccccagcttt ctgagcgcca gcgtgggcga cagggtgacc    60
atcacctgca aggccagcca ggacgtgggc accacagtgg cctggtacca gcagaagccc   120
ggcaaggccc ccaagctgct gatctactgg gccagcacca gcatacagg cgtgcccagc    180 agattcagcg gcagcggaag cggcaccgag ttcaccctga ccatcagcag cctgcagccc   240
gaggacttcg ccacctacta ctgccagcag tacagctcct accccacac cttcggccag    300 ggcaccaagc tggagatcaa g                                             321
```

<210> SEQ ID NO 84
<211> LENGTH: 7
<212> TYPE: PRT
<213> ORGANISM: Artificial Sequence
<220> FEATURE:
<223> OTHER INFORMATION: VL-CDR2

<400> SEQUENCE: 84

```
Arg Ala Asp Arg Leu Leu Glu
1               5
```

<210> SEQ ID NO 85
<211> LENGTH: 9
<212> TYPE: PRT
<213> ORGANISM: Artificial Sequence
<220> FEATURE:
<223> OTHER INFORMATION: VH-CDR3

<400> SEQUENCE: 85

```
Trp Glu Gly Pro Leu Ala Met Asp Tyr
1               5
```

<210> SEQ ID NO 86
<211> LENGTH: 114
<212> TYPE: PRT
<213> ORGANISM: Artificial Sequence
<220> FEATURE:
<223> OTHER INFORMATION: JH6b

<400> SEQUENCE: 86

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ile Ser Thr Gly Met Asp Val Trp Gly Gln Gly Thr Thr Val Thr Val
            100                 105                 110

Ser Ser
```

<210> SEQ ID NO 87
<211> LENGTH: 114
<212> TYPE: PRT
<213> ORGANISM: Artificial Sequence

```
<220> FEATURE:
<223> OTHER INFORMATION: VH_g3

<400> SEQUENCE: 87
```

| | | | | | | | | | | | | | | | |
|---|---|---|---|---|---|---|---|---|---|---|---|---|---|---|---|
|Gln|Val|Gln|Leu|Val|Gln|Ser|Gly|Ala|Glu|Val|Lys|Lys|Pro|Gly|Ala|
|1| | | |5| | | | |10| | | | |15| |

| | | | | | | | | | | | | |
|---|---|---|---|---|---|---|---|---|---|---|---|---|
|Ser|Val|Lys|Val|Ser|Cys|Lys|Ala|Ser|Gly|Tyr|Thr|Phe|Thr|Asp|Tyr|
| | | | |20| | | | |25| | | | |30| |

|Glu|Met|His|Trp|Val|Lys|Gln|Ala|Pro|Gly|Gln|Gly|Leu|Glu|Trp|Ile|
| | | | |35| | | | |40| | | | |45| |

|Gly|Ala|Thr|Asp|Pro|Glu|Thr|Gly|Asn|Ser|Ala|Tyr|Asn|Gln|Lys|Phe|
| |50| | | | |55| | | | |60| | | | |

|Lys|Gly|Lys|Ala|Thr|Met|Thr|Ala|Asp|Lys|Ser|Ser|Thr|Ala|Tyr|
|65| | | | |70| | | | |75| | | | |80|

|Met|Glu|Leu|Ser|Ser|Leu|Arg|Ser|Glu|Asp|Thr|Ala|Val|Tyr|Tyr|Cys|
| | | | |85| | | | |90| | | | |95| |

|Ile|Ser|Thr|Gly|Trp|Asn|Asp|Trp|Gly|Gln|Gly|Thr|Thr|Val|Thr|Val|
| | | |100| | | | |105| | | | |110| | |

Ser Ser

```
<210> SEQ ID NO 88
<211> LENGTH: 107
<212> TYPE: PRT
<213> ORGANISM: Artificial Sequence
<220> FEATURE:
<223> OTHER INFORMATION: JK2

<400> SEQUENCE: 88
```

|Asp|Ile|Gln|Met|Thr|Gln|Ser|Pro|Ser|Ser|Leu|Ser|Ala|Ser|Val|Gly|
|---|---|---|---|---|---|---|---|---|---|---|---|---|---|---|---|
|1| | | |5| | | | |10| | | | |15| |

|Asp|Arg|Val|Thr|Ile|Thr|Cys|Arg|Ala|Ser|Gln|Gly|Ile|Ser|Asn|Tyr|
| | | | |20| | | | |25| | | | |30| |

|Leu|Ala|Trp|Phe|Gln|Gln|Lys|Pro|Gly|Lys|Ala|Pro|Lys|Ser|Leu|Ile|
| | | | |35| | | | |40| | | | |45| |

|Tyr|Ala|Ala|Ser|Ser|Leu|Gln|Ser|Gly|Val|Pro|Ser|Arg|Phe|Ser|Gly|
| |50| | | | |55| | | | |60| | | | |

|Ser|Gly|Ser|Gly|Thr|Asp|Phe|Thr|Leu|Thr|Ile|Ser|Ser|Leu|Gln|Pro|
|65| | | | |70| | | | |75| | | | |80|

|Glu|Asp|Phe|Ala|Thr|Tyr|Tyr|Cys|Gln|Gln|Tyr|Asn|Ser|Tyr|Pro|Tyr|
| | | | |85| | | | |90| | | | |95| |

|Thr|Phe|Gly|Gln|Gly|Thr|Lys|Leu|Glu|Ile|Lys|
| | | |100| | | | |105| | |

```
<210> SEQ ID NO 89
<211> LENGTH: 107
<212> TYPE: PRT
<213> ORGANISM: Artificial Sequence
<220> FEATURE:
<223> OTHER INFORMATION: VL_g2

<400> SEQUENCE: 89
```

|Asp|Ile|Lys|Met|Thr|Gln|Ser|Pro|Ser|Ser|Leu|Ser|Ala|Ser|Val|Gly|
|---|---|---|---|---|---|---|---|---|---|---|---|---|---|---|---|
|1| | | |5| | | | |10| | | | |15| |

|Asp|Arg|Val|Thr|Ile|Thr|Cys|Lys|Ala|Ser|Gln|Asp|Ile|Asn|Ser|Tyr|
| | | | |20| | | | |25| | | | |30| |

|Leu|Ser|Trp|Phe|Gln|Gln|Lys|Pro|Gly|Lys|Ser|Pro|Lys|Ser|Leu|Ile|
| | | | |35| | | | |40| | | | |45| |

```
Tyr Arg Ala Asp Arg Leu Leu Asp Gly Val Pro Ser Arg Phe Ser Gly
    50                  55                  60

Ser Gly Ser Gly Gln Asp Tyr Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Leu Glu Ile Lys
            100                 105

<210> SEQ ID NO 90
<211> LENGTH: 117
<212> TYPE: PRT
<213> ORGANISM: Artificial Sequence
<220> FEATURE:
<223> OTHER INFORMATION: JH6b

<400> SEQUENCE: 90

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
                20                  25                  30

Tyr Trp Ser Trp Ile Arg Gln Pro Pro Gly Lys Gly Leu Glu Trp Ile
            35                  40                  45

Gly Tyr Ile Tyr Tyr Ser Gly Ser Thr Asn Tyr Asn Pro Ser Leu Lys
        50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Trp Phe Gly Glu Leu Leu Met Asp Val Trp Gly Gln Gly Thr Thr
            100                 105                 110

Val Thr Val Ser Ser
        115

<210> SEQ ID NO 91
<211> LENGTH: 117
<212> TYPE: PRT
<213> ORGANISM: Artificial Sequence
<220> FEATURE:
<223> OTHER INFORMATION: VH_g0

<400> SEQUENCE: 91

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Lys Tyr
                20                  25                  30

Gly Val His Trp Ile Arg Gln Pro Pro Gly Lys Gly Leu Glu Trp Ile
            35                  40                  45

Gly Val Ile Trp Arg Gly Gly Ile Thr Asp Tyr Asn Ala Ala Phe Met
        50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95
```

Arg Trp Asp Gly Pro Leu Ala Met Asp Tyr Trp Gly Gln Gly Thr Thr
            100                 105                 110

Val Thr Val Ser Ser
        115

<210> SEQ ID NO 92
<211> LENGTH: 117
<212> TYPE: PRT
<213> ORGANISM: Artificial Sequence
<220> FEATURE:
<223> OTHER INFORMATION: VH_g1

<400> SEQUENCE: 92

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Ile Ile Lys Tyr
            20                  25                  30

Gly Val His Trp Ile Arg Gln Pro Pro Gly Lys Gly Leu Glu Trp Ile
        35                  40                  45

Gly Val Ile Trp Arg Gly Gly Ile Thr Asp Tyr Asn Ala Ala Phe Met
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Trp Asp Gly Pro Leu Ala Met Asp Tyr Trp Gly Gln Gly Thr Thr
            100                 105                 110

Val Thr Val Ser Ser
        115

<210> SEQ ID NO 93
<211> LENGTH: 117
<212> TYPE: PRT
<213> ORGANISM: Artificial Sequence
<220> FEATURE:
<223> OTHER INFORMATION: VH_g3

<400> SEQUENCE: 93

Arg Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ile Lys Tyr
            20                  25                  30

Gly Val His Trp Ile Arg Gln Pro Pro Gly Lys Gly Leu Glu Trp Ile
        35                  40                  45

Gly Val Ile Trp Arg Gly Gly Ile Thr Asp Tyr Asn Ala Ala Phe Met
    50                  55                  60

Ser Arg Val Thr Ile Ser Lys Asp Thr Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Trp Asp Gly Pro Leu Ala Met Asp Tyr Trp Gly Gln Gly Thr Thr
            100                 105                 110

Val Thr Val Ser Ser
        115

<210> SEQ ID NO 94
<211> LENGTH: 107
<212> TYPE: PRT

<213> ORGANISM: Artificial Sequence
<220> FEATURE:
<223> OTHER INFORMATION: JK2

<400> SEQUENCE: 94

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Tyr
                85                  90                  95

Thr Phe Gly Gln Gly Thr Lys Leu Glu Ile Lys
            100                 105

<210> SEQ ID NO 95
<211> LENGTH: 107
<212> TYPE: PRT
<213> ORGANISM: Artificial Sequence
<220> FEATURE:
<223> OTHER INFORMATION: VL_g2

<400> SEQUENCE: 95

Asp Ile Val Leu Thr Gln Ser Pro Ser Phe Leu Ser Ala Ser Val Gly
1               5                   10                  15

Asp Arg Val Thr Ile Thr Cys Lys Ala Ser Gln Asp Val Gly Thr Thr
            20                  25                  30

Val Ala Trp Tyr Gln Gln Lys Pro Gly Lys Ser Pro Lys Leu Leu Ile
        35                  40                  45

Tyr Trp Ala Ser Thr Arg His Thr Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Ser Ser Tyr Pro Tyr
                85                  90                  95

Thr Phe Gly Gln Gly Thr Lys Leu Glu Ile Lys
            100                 105

<210> SEQ ID NO 96
<211> LENGTH: 13
<212> TYPE: PRT
<213> ORGANISM: Artificial Sequence
<220> FEATURE:
<223> OTHER INFORMATION: LAG-3 Extra cyclic peptide
<220> FEATURE:
<221> NAME/KEY: MISC_FEATURE
<222> LOCATION: (13)..(13)
<223> OTHER INFORMATION: coupled to biotin

<400> SEQUENCE: 96

Leu Ala Pro Gly Pro His Pro Ala Ala Pro Ser Ser Lys
1               5                   10

<210> SEQ ID NO 97
<211> LENGTH: 13
<212> TYPE: PRT

```
<213> ORGANISM: Artificial Sequence
<220> FEATURE:
<223> OTHER INFORMATION: LAG-3 Extra cyclic peptide
<220> FEATURE:
<221> NAME/KEY: MISC_FEATURE
<222> LOCATION: (13)..(13)
<223> OTHER INFORMATION: coupled to biotin

<400> SEQUENCE: 97

Ala Pro Gly Pro His Pro Ala Ala Pro Ser Ser Trp Lys
1               5                   10

<210> SEQ ID NO 98
<211> LENGTH: 13
<212> TYPE: PRT
<213> ORGANISM: Artificial Sequence
<220> FEATURE:
<223> OTHER INFORMATION: LAG-3 Extra cyclic peptide
<220> FEATURE:
<221> NAME/KEY: MISC_FEATURE
<222> LOCATION: (13)..(13)
<223> OTHER INFORMATION: coupled to biotin

<400> SEQUENCE: 98

Pro Gly Pro His Pro Ala Ala Pro Ser Ser Trp Gly Lys
1               5                   10

<210> SEQ ID NO 99
<211> LENGTH: 13
<212> TYPE: PRT
<213> ORGANISM: Artificial Sequence
<220> FEATURE:
<223> OTHER INFORMATION: LAG-3 Extra cyclic peptide
<220> FEATURE:
<221> NAME/KEY: MISC_FEATURE
<222> LOCATION: (13)..(13)
<223> OTHER INFORMATION: coupled to biotin

<400> SEQUENCE: 99

Gly Pro His Pro Ala Ala Pro Ser Ser Trp Gly Pro Lys
1               5                   10

<210> SEQ ID NO 100
<211> LENGTH: 13
<212> TYPE: PRT
<213> ORGANISM: Artificial Sequence
<220> FEATURE:
<223> OTHER INFORMATION: LAG-3 Extra cyclic peptide
<220> FEATURE:
<221> NAME/KEY: MISC_FEATURE
<222> LOCATION: (13)..(13)
<223> OTHER INFORMATION: coupled to biotin

<400> SEQUENCE: 100

Pro His Pro Ala Ala Pro Ser Ser Trp Gly Pro Arg Lys
1               5                   10

<210> SEQ ID NO 101
<211> LENGTH: 13
<212> TYPE: PRT
<213> ORGANISM: Artificial Sequence
<220> FEATURE:
<223> OTHER INFORMATION: LAG-3 Extra cyclic peptide
<220> FEATURE:
<221> NAME/KEY: MISC_FEATURE
<222> LOCATION: (13)..(13)
<223> OTHER INFORMATION: coupled to biotin
```

<400> SEQUENCE: 101

His Pro Ala Ala Pro Ser Ser Trp Gly Pro Arg Pro Lys
1               5                   10

<210> SEQ ID NO 102
<211> LENGTH: 13
<212> TYPE: PRT
<213> ORGANISM: Artificial Sequence
<220> FEATURE:
<223> OTHER INFORMATION: LAG-3 Extra cyclic peptide
<220> FEATURE:
<221> NAME/KEY: MISC_FEATURE
<222> LOCATION: (13)..(13)
<223> OTHER INFORMATION: coupled to biotin

<400> SEQUENCE: 102

Pro Ala Ala Pro Ser Ser Trp Gly Pro Arg Pro Arg Lys
1               5                   10

<210> SEQ ID NO 103
<211> LENGTH: 13
<212> TYPE: PRT
<213> ORGANISM: Artificial Sequence
<220> FEATURE:
<223> OTHER INFORMATION: LAG-3 Extra cyclic peptide
<220> FEATURE:
<221> NAME/KEY: MISC_FEATURE
<222> LOCATION: (13)..(13)
<223> OTHER INFORMATION: coupled to biotin

<400> SEQUENCE: 103

Ala Ala Pro Ser Ser Trp Gly Pro Arg Pro Arg Arg Lys
1               5                   10

<210> SEQ ID NO 104
<211> LENGTH: 13
<212> TYPE: PRT
<213> ORGANISM: Artificial Sequence
<220> FEATURE:
<223> OTHER INFORMATION: LAG-3 Extra cyclic peptide
<220> FEATURE:
<221> NAME/KEY: MISC_FEATURE
<222> LOCATION: (13)..(13)
<223> OTHER INFORMATION: coupled to biotin

<400> SEQUENCE: 104

Ala Pro Ser Ser Trp Gly Pro Arg Pro Arg Arg Tyr Lys
1               5                   10

<210> SEQ ID NO 105
<211> LENGTH: 13
<212> TYPE: PRT
<213> ORGANISM: Artificial Sequence
<220> FEATURE:
<223> OTHER INFORMATION: LAG-3 Extra cyclic peptide
<220> FEATURE:
<221> NAME/KEY: MISC_FEATURE
<222> LOCATION: (13)..(13)
<223> OTHER INFORMATION: coupled to biotin

<400> SEQUENCE: 105

Pro Ser Ser Trp Gly Pro Arg Pro Arg Arg Tyr Thr Lys
1               5                   10

<210> SEQ ID NO 106
<211> LENGTH: 13
<212> TYPE: PRT
<213> ORGANISM: Artificial Sequence

```
<220> FEATURE:
<223> OTHER INFORMATION: LAG-3 Extra cyclic peptide
<220> FEATURE:
<221> NAME/KEY: MISC_FEATURE
<222> LOCATION: (13)..(13)
<223> OTHER INFORMATION: coupled to biotin

<400> SEQUENCE: 106

Ser Ser Trp Gly Pro Arg Pro Arg Arg Tyr Thr Val Lys
1               5                   10

<210> SEQ ID NO 107
<211> LENGTH: 13
<212> TYPE: PRT
<213> ORGANISM: Artificial Sequence
<220> FEATURE:
<223> OTHER INFORMATION: LAG-3 Extra cyclic peptide
<220> FEATURE:
<221> NAME/KEY: MISC_FEATURE
<222> LOCATION: (13)..(13)
<223> OTHER INFORMATION: coupled to biotin

<400> SEQUENCE: 107

Ser Trp Gly Pro Arg Pro Arg Arg Tyr Thr Val Leu Lys
1               5                   10

<210> SEQ ID NO 108
<211> LENGTH: 13
<212> TYPE: PRT
<213> ORGANISM: Artificial Sequence
<220> FEATURE:
<223> OTHER INFORMATION: LAG-3 Extra cyclic peptide
<220> FEATURE:
<221> NAME/KEY: MISC_FEATURE
<222> LOCATION: (13)..(13)
<223> OTHER INFORMATION: coupled to biotin

<400> SEQUENCE: 108

Trp Gly Pro Arg Pro Arg Arg Tyr Thr Val Leu Ser Lys
1               5                   10

<210> SEQ ID NO 109
<211> LENGTH: 13
<212> TYPE: PRT
<213> ORGANISM: Artificial Sequence
<220> FEATURE:
<223> OTHER INFORMATION: LAG-3 Extra cyclic peptide
<220> FEATURE:
<221> NAME/KEY: MISC_FEATURE
<222> LOCATION: (13)..(13)
<223> OTHER INFORMATION: coupled to biotin

<400> SEQUENCE: 109

Gly Pro Arg Pro Arg Arg Tyr Thr Val Leu Ser Val Lys
1               5                   10

<210> SEQ ID NO 110
<211> LENGTH: 31
<212> TYPE: PRT
<213> ORGANISM: Artificial Sequence
<220> FEATURE:
<223> OTHER INFORMATION: exposed outer loop of extracellular region of
      the human LAG-3 protein
<220> FEATURE:
<221> NAME/KEY: MISC_FEATURE
<222> LOCATION: (31)..(31)
<223> OTHER INFORMATION: coupled to biotin
```

```
<400> SEQUENCE: 110

Gly Pro Pro Ala Ala Ala Pro Gly His Pro Leu Ala Pro Gly Pro His
1               5                   10                  15

Pro Ala Ala Pro Ser Ser Trp Gly Pro Arg Pro Arg Arg Tyr Lys
            20                  25                  30
```